United States Patent [19]

Levitt

[11] 4,394,506

[45] Jul. 19, 1983

[54] AGRICULTURAL SULFONAMIDES

[75] Inventor: George Levitt, Wilmington, Del.

[73] Assignee: E. I. Du Pont de Nemours and Company, Wilmington, Del.

[21] Appl. No.: 98,781

[22] Filed: Nov. 30, 1979

Related U.S. Application Data

[63] Continuation-in-part of Ser. No. 29,281, Apr. 13, 1979, abandoned, which is a continuation-in-part of Ser. No. 15,341, Mar. 1, 1979, abandoned, which is a continuation-in-part of Ser. No. 965,070, Nov. 30, 1978, abandoned, which is a continuation-in-part of Ser. No. 910,965, May 30, 1978, abandoned.

[51] Int. Cl.[3] .................... C07D 239/28; C07D 239/30

[52] U.S. Cl. ........................................ 544/321; 71/88; 71/90; 71/92; 71/93; 544/112; 544/113; 544/114; 544/182; 544/211; 544/326; 544/327; 544/328; 544/329; 544/331; 544/332

[58] Field of Search ................................ 544/332, 321

[56] References Cited

U.S. PATENT DOCUMENTS 3,639,474 2/1972 Harrington et al. ................ 424/321

FOREIGN PATENT DOCUMENTS 174510 5/1963 Argentina .
853374 10/1977 Belgium .
1468747 2/1967 France .

OTHER PUBLICATIONS

Logemann et al., Chem. Abst., vol. 58, (1959) 18052g.
Wojclechowski, J. Acta. Polon. Pharm., vol. 19 (1962) pp. 121-125.

*Primary Examiner*—Catherine L. Mills

[57] ABSTRACT

N-(heterocyclicaminocarbonyl)arylsulfonamides in which the aryl radical is substituted in the 2-position by a carboxy radical, ester, thioester, or amide thereof; e.g. N-[(4,6-dimethylpyrimidin-2-yl)aminocarbonyl]-2-methoxycarbonylbenzenesulfonamide or N-[(4,6-dimethoxy-1,3,5-triazin-2-yl)aminocarbonyl]-2-methoxycarbonylbenzenesulfonamide; are useful for the regulation of plant growth and as pre-emergence and post-emergence herbicides.

8 Claims, No Drawings

AGRICULTURAL SULFONAMIDES

RELATED APPLICATIONS

This application is a continuation-in-part of my copending application Ser. No. 029,281, filed Apr. 13, 1979, which is a continuation-in-part of my copending application Ser. No. 015,341, filed Mar. 1, 1979, which is a continuation-in-part of my copending application Ser. No. 965,070 filed Nov. 30, 1978, which is a continuation-in-part of my copending application Ser. No. 910,965, filed May 30, 1978, now all abandoned.

BACKGROUND OF THE INVENTION

This invention relates to novel N-(heterocyclicaminocarbonyl)arylsulfonamides in which the aryl radical is substituted by a carboxyl radical, ester, thioester or amide thereof. The compounds of this invention and their agriculturally suitable salts, are useful as agricultural chemicals, e.g. plant growth regulants and herbicides. P Netherlands Pat. No. 121,788, published Sept. 15, 1966, discloses the preparation of compounds of the following Formula and their use as general or selective herbicides:

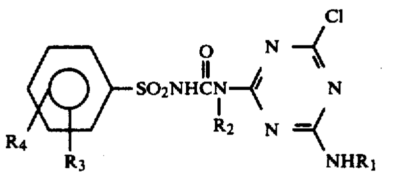

wherein $R_1$ and $R_2$ may independently be alkyl of 1–4 carbon atoms; and $R_3$ and $R_4$ may independently be hydrogen, chlorine or alkyl of 1–4 carbon atoms.

U.S. Pat. No. 3,637,366 discloses compounds having the formula:

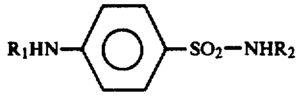

wherein $R_1$ is hydrogen or lower saturated aliphatic acyl and $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

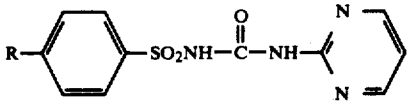

wherein R=H, halogen, $CF_3$ or alkyl.

Logemann et al. Chem Ab., 53, 18052 g (1959), disclose a number of sulfonamides, including uracil derivatives and those having the formula:

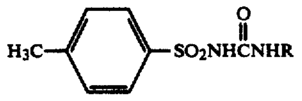

wherein

R is butyl, phenyl, or

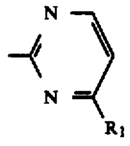

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

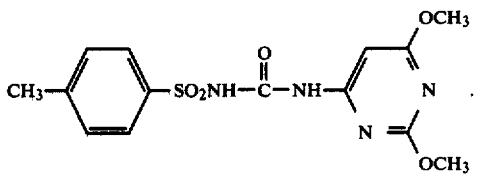

Based upon similarity to a known compound, the author speculated that the foregoing compound might have a hypoglycemic activity.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959]:

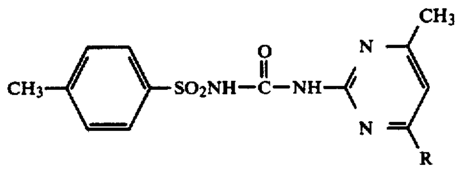

wherein R=H or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. The need still exists however, for more effective herbicides.

SUMMARY OF THE INVENTION

According to this invention, there are provided novel compounds of Formula I and their agriculturally suitable salts, e.g. Na, K, alkyl ammonium, trichloroacetic acid, suitable agricultural compositions containing them and methods of using them as general or selective preemergence and post-emergence herbicides and as plant growth regulants:

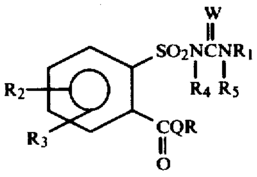

(I)

wherein Q is O, S

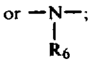

when Q is O or S then R is $C_1$–$C_{12}$ alkyl; $C_3$–$C_{10}$ alkenyl; $C_3$–$C_{10}$ alkynyl; $C_2$–$C_6$ alkyl substituted with one to four substituents selected from 0–3 atoms of F, Cl, Br, 0–2 methoxy groups and 0–1 cyano groups; $-CH_2CN$;

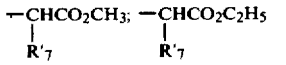

where $R_7'$ is H or $CH_3$; $C_3$–$C_6$ alkenyl substituted with 1–3 atoms of F, Cl, Br; $C_3$–$C_6$ alkynyl substituted with one of F, Cl or Br; $C_5$–$C_8$ cycloalkyl; $C_5$–$C_8$ cycloalkenyl; $C_5$–$C_6$ cycloalkyl substituted with $OCH_3$, alkyl of $C_2$–$C_4$, F, Cl or Br or one to four methyl groups; $C_4$–$C_{10}$ cycloalkylalkyl; $C_4$–$C_8$ cycloalkylalkyl with 1–2 $CH_3$; $C_7$–$C_{10}$ bicycloalkyl; $C_7$–$C_{10}$ bicycloalkenyl; $C_{10}$ tricycloalkyl, $C_{10}$ tricycloalkenyl;

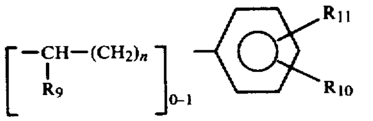

where $R_9$ is $C_1$–$C_3$ alkyl or hydrogen, $R_{10}$ and $R_{11}$ are independently hydrogen, $C_1$–$C_3$ alkyl, Cl, Br, $-OCH_3$, $-OC_2H_5$ or $R_{10}$ and $R_{11}$ may be taken together to form a 5 or 6 member ring;

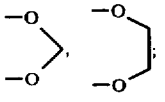

and n is 0, 1, 2 or 3 provided the total number of carbon atoms is $\leq 12$;

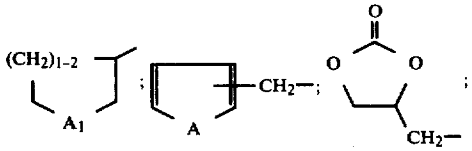

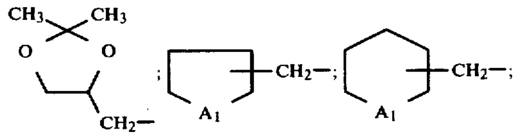

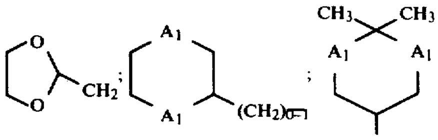

A is O, S; $A_1$ is O, S, $SO_2$; when Q is O, then R is H, M, $-CH_2CH_2OR_7$; $-CH_2CH_2CH_2OR_7$,

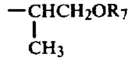

where $R_7$ is $-CH_2CH_3$, $-CH(CH_3)_2$, phenyl, $-CH_2CH_2Cl$, $-CH_2CCl_3$; $CH_2OR_8'$ where $R_8'$ is $-CH_3$, $-CH_3CH_2$, $-CH(CH_3)_2$, $-CH_2CH_2Cl$, $-CH_2CCl_3$, phenyl,

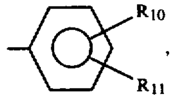

$-CH_2CH_2OCH_3$, $-CH_2CH_2OCH_2CH_3$; $-CH_2CH_2O)_{n'}R_8$,

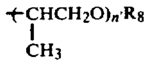

where $R_8$ is $-CH_3$, $-CH_2CH_3$, $-CH(CH_3)_2$, phenyl, $-CH_2CH_2Cl$, $-CH_2CCl_3$ and n' is 2 or 3;

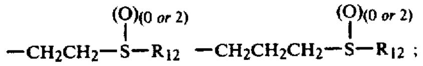

where $R_{12}$ is $-CH_3$, $-CH_2CH_3$, $-CH(CH_3)_2$, or phenyl; and provided R has a total number of carbon atoms $\leq 13$; when Q is

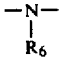

then R is hydrogen; $C_1$–$C_{12}$ alkyl; $-(CH_2CH_2-)_{n'''}R_{12}$; $-CH_2CH_2CH_2OR_{12}$ where $R_{12}$ is as defined above and n''' is 1–3; $C_3$–$C_{10}$ alkenyl; $C_3$–$C_6$ alkynyl; $C_3$–$C_8$ cycloalkyl; $C_5$–$C_6$ cycloalkenyl; $C_5$–$C_8$ cycloalkyl substituted with 1 to 3 substituents selected from 0–2 $-OCH_3$, 0–3 $-CH_3$ or $-C_2H_5$; trifluoromethylcyclohexyl; $C_4$–$C_{10}$ cycloalkylalkyl; $C_4$–$C_8$ cycloalkylalkyl substituted with 1–2 $-CH_3$; $-CH_2CN$; $-CH_2CH_2CN$;

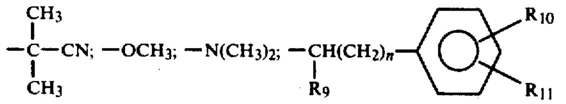

where n, $R_9$, $R_{10}$ and $R_{11}$ are as defined above;

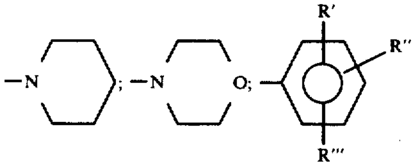

where R' is hydrogen, $C_1$-$C_4$ alkyl, —$OCH_3$, F, Br, Cl, —$CF_3$, CN, $NO_2$, —$SO_2CH_3$, —$SCH_3$, —$N(CH_3)_2$; R'' is hydrogen, $C_1$-$C_4$ alkyl, —$OCH_3$, F, Br, Cl; R''' is hydrogen, —$CH_3$, Cl, F or Br; $R_6$ is hydrogen, $C_1$-$C_6$ alkyl, allyl, —$CH_2CN$; or —$CH_2CH_2CN$; or $R_6$ and R can be taken together to form —$(CH_2)_4$—, —$(CH_2)_5$—, —$(CH_2)_6$—, —$CH_2CH_2OCH_2CH_2$—; or

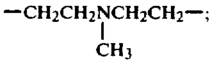

with the proviso that when R is —$OCH_3$ then $R_6$ is —$CH_3$; when $R_6$ is —$CH_2CH_2CN$ or —$CH_2CN$ then R is —$CH_2CH_2CN$ or $CH_2CN$; and R and $R_6$ have a total number of carbon atoms $\leq 13$;

$R_1$ is 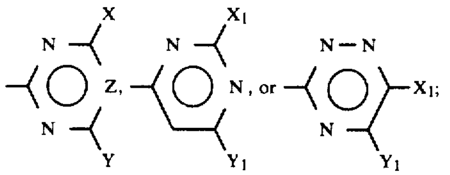

$R_2$ is H, Cl, Br, F, $C_1$-$C_3$ alkyl, —$NO_2$, —$SO_2CH_3$, —$OCH_3$, —$SCH_3$, —$CF_3$, —$N(CH_3)_2$, —$NH_2$, or —CN; $R_3$ is H, Cl, Br, F or $CH_3$; $R_4$ is H, or —$CH_3$; $R_5$ is H, —$CH_3$, or —$OCH_3$; M is an alkali metal; W is oxygen or sulfur; X is H, Cl, —$CH_3$, —$OCH_3$, —$OCH_2CH_3$ or —$OCH_2CH_2OCH_3$; Y is H; F; Cl; Br; $C_1$-$C_4$ alkyl;

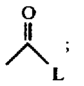

$C_1$-$C_4$ alkyl substituted with —$OCH_3$, —$OC_2H_5$, —CN,

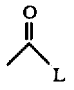

or 1 to 3 atoms of F, Cl, Br; $C_3$-$C_4$ alkenyl; —$CH_2C{\equiv}CR_{13}$ where $R_{13}$ is H, —$CH_3$, —$CH_2Cl$; —A—$(CH_2)_{n'}$—$A_1$ —($C_1$-$C_3$ alkyl), and n', A and $A_1$ are as previously defined;

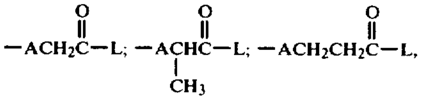

where L is —$NH_2$, OH,

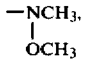

—NH($C_1$-$C_4$ alkyl), —N($C_1$-$C_4$ alkyl)$_2$, $C_1$-$C_6$ alkoxy; SCN; —$N_3$; $NR_{16}R_{17}$ where $R_{16}$ is H or $CH_3$ and $R_{17}$ is H, —$OCH_3$, $C_1$-$C_6$ alkyl, $C_1$-$C_4$ alkyl substituted with —CN,

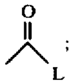

$C_3$-$C_4$ alkenyl; $C_3$-$C_6$ cycloalkyl; or $C_2$-$C_3$ alkyl substituted with —$OCH_3$, $OC_2H_5$; or $R_{16}$ and $R_{17}$ can be taken together to form —$CH_2CH_2CH_2CH_2$—, —$CH_2CH_2OCH_2CH_2$—; —O—$R_{14}$ where $R_{14}$ is $C_1$-$C_4$ alkyl; $C_2$-$C_4$ alkyl substituted with 1-3 atoms of F, Cl or Br; $C_1$-$C_4$ alkyl substituted with cyano; $C_3$-$C_4$ alkenyl, —$CH_2C{\equiv}CR_{13}$; where $R_{13}$ is as previously defined;

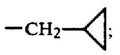

—$SR_{15}$ where $R_{15}$ is $C_1$-$C_4$ alkyl, $C_1$-$C_2$ alkyl substituted with CN, allyl, propargyl; with the provision that when Y is $\geq 4$ carbon atoms, R is $\leq 4$ carbon atoms, when X is Cl, then Y is Cl, and when X and Y are both H, then R is $\leq 4$ carbon atoms. Z is N or CH; $Y_1$ is H, —$OCH_3$, —$CH_3$ or $OCH_2CH_3$; $X_1$ is H, Cl, —$OCH_3$, —$OCH_2CH_3$, —$CH_3$; providing that $X_1$ and $Y_1$ are not both simultaneously hydrogen and when $R_1$ is

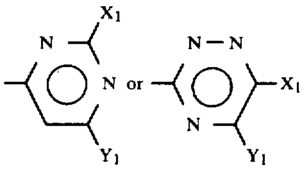

then $R_4$ and $R_5$ are both H and R is $\leq 5$ carbon atoms.

More preferred for higher activity and/or ease of synthesis are the following:

More preferred are the following

1. A compound of the generic scope where $R_4$ and $R_5$ are H, W is O, and the carbon of R bonded to Q is also bonded to at least one H.

2. A compound of the preferred (1)-where $R_2$ is H, Cl, Br, F, $C_1$-$C_3$ alkyl, —$NO_2$, —$OCH_3$, —$SCH_3$, —$SO_2CH_3$, —$CF_3$, —$N(CH_3)_2$, —$NH_2$, —CN and $R_3$ is H and is para to the sulfonyl group.

3. A compound of preferred (2) where Q is O or S and R is $C_1$-$C_6$ alkyl, $C_3$-$C_6$ alkenyl, $C_3$-$C_6$ alkynyl; $C_3$-$C_6$ alkynyl substituted with one of F, Cl, Br; $C_2$-$C_4$ alkyl substituted with one to four substituents selected from 0-3 F, Cl, 0-2 $OCH_3$, 0-1 CN; $CH_2CN$; $C_3$-$C_4$ alkenyl substituted with 1-3 Cl; $C_5$-$C_6$ cycloalkyl; $C_5$-$C_6$ cycloalkenyl; $C_5$-$C_6$ cycloalkyl substituted with methoxy, $C_2H_5$, chloro or up to four methyl groups; $C_4$-$C_7$ cycloalkylalkyl.

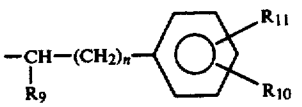

where $R_9$ is H, $—CH_3$ n is 0, 1, $R_{10}$ and $R_{11}$ are independently H, $—CH_3$, Cl, $—OCH_3$;

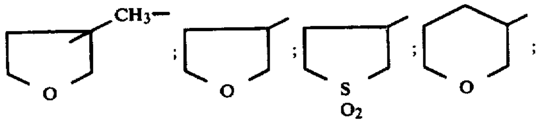

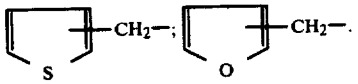

4. Compounds of Preferred (2) where Q is O and R is H, M, $—CH_2CH_2OR_7$,

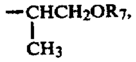

$—CH_2CH_2CH_2OR_7$ where $R_7$ is as previously defined, $—(CH_2CH_2O)_2R_8$,

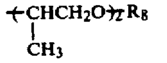

where $R_8$ is $C_1$-$C_3$ alkyl, $CH_2CH_2Cl$.

5. Compounds of preferred (2) where Q is $—NR_6—$ and R is H; $C_1$-$C_6$ alkyl; $—CH_2CH_2OR_{12}$; $—CH_2CH_2CH_2OR_{12}$, where $R_{12}$ is defined as above; $C_3$-$C_6$ alkenyl; $C_3$-$C_6$ alkynyl; $C_3$-$C_6$ cycloalkyl; $C_5$-$C_6$ cycloalkenyl; $C_6$ cycloalkyl substituted with any one of 1-2 $—OCH_3$, 1-3 $CH_3$ or $—C_2H_5$; trifluoromethylcyclohexyl; $C_4$-$C_7$ cycloalkylalkyl; $—CH_2CN$; $—CH_2CH_2CN$;

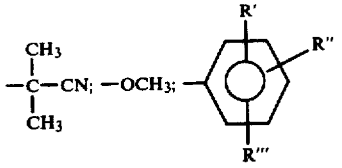

where R' is H, R'' is H, $C_1$-$C_4$ alkyl, $—OCH_3$, F, Br, Cl; R''' is H, $—CH_3$, Cl, F, Br;

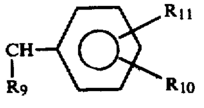

where $R_9$ is H, $CH_3$ and $R_{10}$ and $R_{11}$ may independently be H, $CH_3$, Cl, $OCH_3$; $R_6$ is H, $C_1$-$C_3$ alkyl, $—CH_2CN$, $—CH_2CH_2CN$, $—CH_2CH{=}CH_2$ and $R_6$ and R may be taken together to form $—CH_2CH_2CH_2CH_2—$, $—CH_2CH_2CH_2CH_2CH_2—$, $—CH_2CH_2OCH_2CH_2—$.

6. Compounds of preferred (2) where X is $CH_3$, $OCH_3$, $OC_2H_5$ and Y is H, $C_1$-$C_4$ alkyl, $C_1$-$C_2$ alkyl substituted with $—OCH_3$, $—OC_2H_5$, $—CN$, $—CO_2CH_3$, $—CO_2C_2H_5$, 1 to 3 atoms of F, Cl; $C_3$-$C_4$ alkenyl; $—OCH_2CO_2$(H, $C_1$-$C_4$ alkyl);

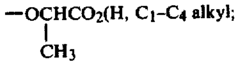

$—OCH_2CH_2CO_2$(H, $C_1$-$C_4$ alkyl); $—OCH_2CH_2O(C_1$-$C_3$ alkyl); $—OCH_2CH_2CH_2O(C_1$-$C_3$ alkyl); $OR_{14}$ where $R_{14}$ is $C_1$-$C_4$ alkyl, $C_2$-$C_3$ alkyl substituted with 1-3 F or Cl, $C_1$-$C_3$ alkyl substituted with CN, $C_3$-$C_4$ alkenyl; $—SCH_3$; $—SC_2H_5$; $NR_{16}R_{17}$ where $R_{16}$ is H, $CH_3$ and $R_{17}$ is $C_1$-$C_4$ alkyl, $C_1$-$C_4$ alkyl substituted with $—CN$, $C_2$-$C_3$ alkyl substituted with $—OCH_3$ or $—OC_2H_5$, $C_3$-$C_4$ alkenyl; and $X_1$ and $Y_1$ are as previously defined.

7. Compounds of preferred (6) where —QR is as defined in preferred (3).

8. Compounds of preferred (6) where —QR is as defined in preferred (4).

9. Compounds of preferred (6) where —QR is as defined in preferred (5).

10. Compounds of preferred (7, 8 or 9) where $R_2$ is H, Cl, $—CH_3$.

11. Compounds of preferred (10) where Q is O, S and R is $C_1$-$C_4$ alkyl; $C_3$-$C_4$ alkenyl; $C_3$-$C_4$ alkynyl; $C_2$-$C_3$ alkyl substituted with $—OCH_3$, Cl, or CN; $CH_2CN$; $C_3$-alkenyl substituted with 1-3 Cl; $CH_2—C{\equiv}C—CH_2Cl$; $C_5$-$C_6$ cycloalkyl; cyclohexenyl, cyclohexyl substituted with 1-3 $—CH_3$,

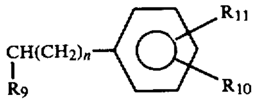

where $R_9$ is H, $CH_3$, n is 0, 1, $R_{10}$ and $R_{11}$ are independently H, $—CH_3$, $OCH_3$, Cl.

12. Compounds of preferred (10) where Q and O and R is H, M, $—CH_2CH_2OR_7$ where $R_7$ is $—C_2H_5$, $—CH(CH_3)_2$, phenyl, $—CH_2CH_2Cl$; and

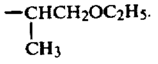

13. Compounds of preferred (10) where Q is $—NR_6—$, $R_6$ is H, $—CH_3$, $—C_2H_5$, and R is $C_1$-$C_4$ alkyl, $—CH_2CH_2OCH_3$, $—CH_2CH_2OC_2H_5$, $C_3$-$C_4$ alkenyl, $C_5$-$C_6$ cycloalkyl, cyclohexyl substituted with 1-3—$CH_3$,

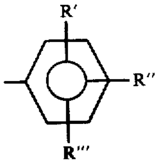

where R' is H, R'' is H, $—CH_3$, Cl, R''' is H, $—CH_3$, Cl;

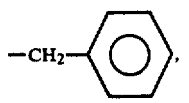

and R and $R_6$ can be taken together to form $-CH_2CH_2CH_2CH_2-$, $-CH_2CH_2OCH_2CH_2-$.

14. Compounds of preferred (10) where $R_1$ is

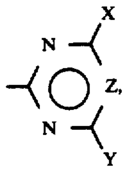

X is $CH_3$, $-OCH_3$, $-OC_2H_5$, and Y is H, $C_1$–$C_3$ alkyl, $-CH_2OCH_3$, $-CH_2OC_2H_5$, $$-OCH_2CO_2(H,\ C_1\text{–}C_2\text{ alkyl})\quad -\underset{CH_3}{OCH}-CO_2(H,\ C_1\text{–}C_2\text{ alkyl}),$$

$-O(C_1$–$C_3$ alkyl), $-O(C_3$–$C_4$ alkenyl), and $NR_{16}R_{17}$ where $R_{16}$ is H, $-CH_3$ and $R_{17}$ is $C_1$–$C_3$ alkyl and Z is CH or N.

15. Compounds of preferred (14) where QR is as defined in preferred (11).

16. Compounds of preferred (14) where QR is as defined in preferred (12).

17. Compounds of preferred (14) where QR is as defined in preferred (13).

18. Compounds of preferred (15, 16 or 17) where $R_2$ and $R_3$ are both hydrogen.

19. Compounds of preferred (18) where Q is O and R is $C_1$–$C_4$ alkyl, $C_3$–$C_4$ alkenyl, $C_2$–$C_3$ alkyl substituted with Cl;

$$-CH_2CH_2O-(CH_3,\ C_2H_5)\quad -\underset{CH_3}{CH}CH_2O-(CH_3,C_2H_5)-,$$

$-CH_2CH_2CH_2O(CH_3,C_2H_5)$.

20. Compounds of preferred (18) where Q is S and R is $C_1$–$C_4$ alkyl or $C_3$–$C_4$ alkenyl.

21. Compounds of preferred (18) where Q is $-NR_6-$ and R is $C_1$–$C_4$ alkyl, $C_3$–$C_4$ alkenyl, $-CH_2CH_2O-(CH_3,C_2H_5)$ or $-CH_2CH_2CH_2O-(CH_3, C_2H_5)$ and $R_6$ *L is H or CH3*, and R and $R_6$ taken together are $-CH_2-_4$ or $-CH_2CH_2OCH_2CH_2-$.

22. Compounds of preferred (18) where X is $CH_3$, $-OCH_3$ or $-OC_2H_5$ and Y is $C_1$–$C_3$ alkyl, $-OCH_3$, $-OC_2H_5$, $-OCH_2CO_2-(CH_3, C_2H_5)$, $$-\underset{CH_3}{OCH}CH_2CO_2-(CH_3,C_2H_5),$$

$CH_2OCH_3$

23. Compounds of preferred (22) where —QR is as defined in preferred 19.

24. Compounds of preferred (22) where QR is as defined in preferred (20).

25. Compounds of preferred (22) where QR is as defined in preferred (21).

Specifically preferred for higher activity and/or greatest ease of synthesis are:

N-[(4,6-dimethylpyrimidin-2-yl)aminocarbonyl]-2-methoxycarbonylbenzenesulfonamide;
N-[(4,6-dimethyl-1,3,5-triazin-2-yl)aminocarbonyl]-2-methoxycarbonylbenzenesulfonamide;
N-[(4-methoxy-6-methylpyrimidin-2-yl)aminocarbonyl]-2-methoxycarbonylbenzenesulfonamide;
N-[(4-methoxy-6-methyl-1,3,5-triazin-2-yl)aminocarbonyl]-2-methoxycarbonylbenzenesulfonamide;
N-[(4,6-dimethoxypyrimidin-2-yl)aminocarbonyl]-2-methoxycarbonylbenzenesulfonamide;
N-[(4,6-dimethoxy-1,3,5-triazin-2-yl)aminocarbonyl]-2-methoxycarbonylbenzenesulfonamide;
N-[(4,6-dimethoxy-1,3,5-triazin-2-yl)aminocarbonyl]-2-(isopropoxycarbonyl)benzenesulfonamide;
N-[(4-methoxy-6-methyl-1,3,5-triazin-2-yl)aminocarbonyl]-2-(isopropoxycarbonyl)benzenesulfonamide;
N-[(4,6-dimethoxy-1,3,5-triazin-2-yl)aminocarbonyl]-2-(2-chloroethoxycarbonyl)benzenesulfonamide;
N-[(4-methoxy-6-methyl-1,3,5-triazin-2-yl)aminocarbonyl]-2-(2-chloroethoxycarbonyl)benzenesulfonamide;
N-[(4-methoxy-6-methyl-1,3,5-triazin-2-yl)aminocarbonyl]-2-propoxycarbonylbenzenesulfonamide;
N-[(4-methoxy-6-methylpyrimidin-2-yl)aminocarbonyl]-2-(2-chloroethoxycarbonyl)benzenesulfonamide;
N-[(4-methoxy-6-methyl-1,3,5-traizin-2-yl)aminocarbonyl]-2-(2-phenyl-1-methylethoxycarbonyl)benzenesulfonamide;
N-[(4-methoxy-6-methyl-1,3,5-triazin-2-yl)aminocarbonyl]-2-[(2-(2-chloroethoxy)ethoxycarbonyl]benzenesulfonamide;
N-[(4-methoxy-6-methyl-1,3,5-triazin-2-yl)aminocarbonyl]-2-(2-ethoxyethoxycarbonyl)benzenesulfonamide;
N-[(4-methoxy-6-methyl-1,3,5-triazin-2-yl)aminocarbonyl]-2-allyloxycarbonylbenzenesulfonamide;
N-[(4-methoxy-6-methylpyrimidin-2-yl)aminocarbonyl]-2-dimethylcarbamoylbenzenesulfonamide;
N-[[[4-methyl-6-(1-methoxycarbonylethoxy)pyrimidin-2-yl]aminocarbonyl]]-2-methoxycarbonylbenzenesulfonamide;
N-[[[4-methyl-6-(1-methoxycabonylethoxy)-1,3,5-triazin-2-yl]aminocarbonyl]]-2-methoxycarbonylbenzenesulfonamide;
N-[(4-methoxy-6-methyl-1,3,5-triazin-2-yl)aminocarbonyl]-2-methylthiocarbonylbenzenesulfonamide;
N-[(4-methoxy-6-methyl-1,3,5-triazin-2-yl)aminocarbonyl]-2-isopropylthiocarbonylbenzenesulfonamide;
N-[(4-methoxy-6-methylpyrimidin-2-yl)aminocarbonyl]-2-isopropylthiocarbonylbenzenesulfonamide;
N-[(4-methoxy-6-methyl-1,3,5-triazin-2-yl)aminocarbonyl]-2-(2-methylpropoxycarbonyl)benzenesulfonamide.
N-[(4-methoxy-6-methylpyrimidin-2-yl)aminocarbonyl]-2-(4-morpholinylaminocarbonyl)benzenesulfonamide;
N-[(4,6-dimethoxypyrimidin-2-yl)aminocarbonyl]-2-(1-pyrrolidinylcarbonyl)benzenesulfonamide;
N-[(4,6-dimethoxypyrimidin-2-yl)aminocarbonyl]-2-(allyloxycarbonyl)benzenesulfonamide;
methyl 2-[[[4-(1-carboxyethoxy)-6-methyl-1,3,5-triazin-2-yl]aminocarbonyl]aminosulfonyl]benzoate; methyl 2-[[(4-ethoxy-6-methyl-1,3,5-triazin-2-yl)aminocarbonyl]aminosulfonyl]benzoate;

2-[[(4,6-dimethoxypyrimidin-2-yl)aminocarbonyl]-aminosulfonyl]-N,N-dimethylbenzamide.

Synthesis

Many of the compounds of Formula I are prepared as shown in Equation 3 by the reaction of an appropriately substituted o-carbonylbenzenesulfonyl isocyanate or isothiocyanate with an appropriate aminopyrimidine or aminotriazine. These compounds of Formula I can be converted to other compounds of Formula I as will be shown in subsequent equations. Thus, o-carbonylbenzenesulfonyl isocyanates and sulfonyl isothiocyanates are important intermediates for the preparation of the compounds of this invention. Therefore, the synthesis of these is described in Equations 1 and 2.

Equation 1

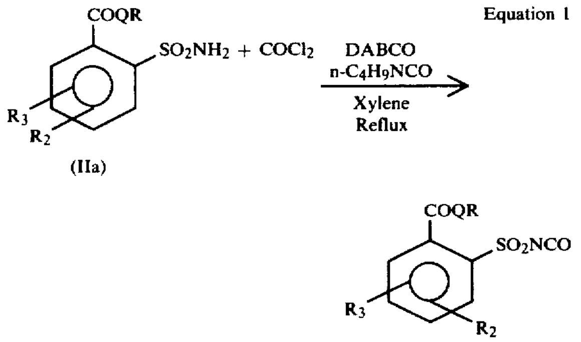

(IIa)

II

A mixture of the appropriate sulfonamide, e.g. an o-alkoxycarbonyl benzenesulfonamide IIa such as the methyl ester, which is known in the art, an alkyl isocyanate such as butyl isocyanate and a catalytic amount of 1,4-diaza[2,2,2]bicyclooctane (DABCO) in xylene or other inert solvent of sufficiently high boiling point (e.g. >135°) is heated to approximately 135°. Phosgene is added to the mixture until an excess of phosgene is present as indicated by a drop in the boiling point. (The mixture is heated further to drive off the excess phosgene). After the mixture is cooled and filtered to remove a small amount of insoluble by-products, the solvent and alkyl isocyanate are distilled off in-vacuo leaving a residue which is the crude sulfonyl isocyanate II. In Equation 1

Q is O

R is $C_1$–$C_{12}$ alkyl; $C_3$–$C_{10}$ alkenyl; $C_2$–$C_6$ alkyl substituted with one to four substituents selected from 0–3 atoms of F, Cl, Br, 0–2 methoxy groups; $C_3$–$C_6$ alkenyl substituted with 1–3 atoms of F, Cl, Br; $C_5$–$C_8$ cycloalkyl; $C_5$–$C_8$ cycloalkenyl; $C_5$–$C_6$ cycloalkyl substituted with any of one to four methyl groups, methoxy, alkyl substituents of $C_2$–$C_4$, F, Cl or Br; $C_4$–$C_{10}$ cycloalkylalkyl; $C_4$–$C_8$ cycloalkylalkyl with 1–2 $CH_3$; $—CH_2CH_2OR_7$; $CH_2CH_2CH_2OR_7$;

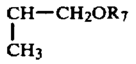

where $R_7$ is $—CH_2CH_3$, $CH(CH_3)_2$, phenyl, $—CH_2CH_2Cl$, $—CH_2CCl_3$; $-(CH_2CH_2O)_{n'}R_8$;

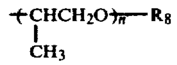

where $R_8$ is $CH_3$, $—CH_2CH_3—CH(CH_3)_2$, phenyl, $—CH_2CH_2Cl$, $—CH_2CCl_3$, and n' is 2 or 3; $R_2$ is H, Cl, Br, F, $C_1$–$C_3$ alkyl, $—NO_2$, $—OCH_3$, $—SCH_3$, $CF_3$, $SO_2CH_3$, $N(CH_3)_2$, CN; $R_3$ is H, Cl, Br or $CH_3$ Where W=S in Formula I the useful sulfonylisothiocyanate intermediates are prepared according to Equations 2 and 2'.

Equation 2

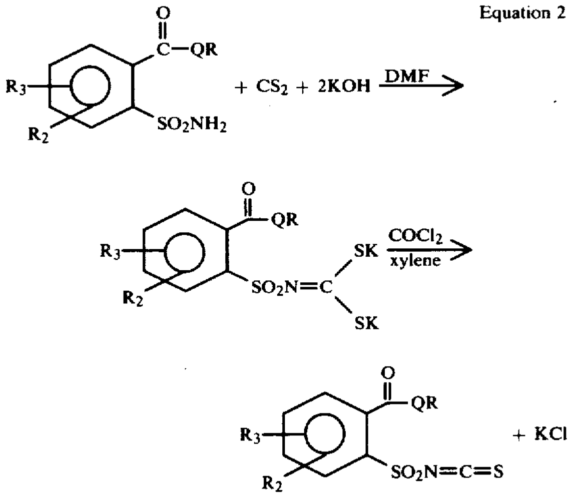

The o-carbonyl substituted sulfonamide is dissolved in dimethylformamide (DMF) with an equivalent amount of carbon disulfide and two equivalents of potassium hydroxide are added portionwise at room temperature. The mixture is stirred for 1–8 hours and diluted with ethylacetate, ethyl ether or similar aprotic solvent to cause the dipotassium salt of the dithiocarbamic acid to precipitate. The salt is isolated, dried and suspended in an inert solvent such as xylene, benzene, carbon tetrachloride or methylene chloride. Phosgene is added to the stirred suspension at below room temperature and the mixture stirred for 1–3 hours. In place of phosgene, a chloroformic ester (e.g. methyl chloroformate), phosphoruspentachloride sulfuryl chloride or thionyl chloride can be used.

The sulfonylisothiocyanate which is formed is usually soluble in the solvent and is isolated by filtering off the inorganic potassium chloride and concentrating the filtrate. These isothiocyanates tend to be unstable and dimerize readily, (Equation 2') however, the dimers can be used Equation 2'

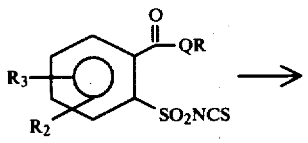

-continued

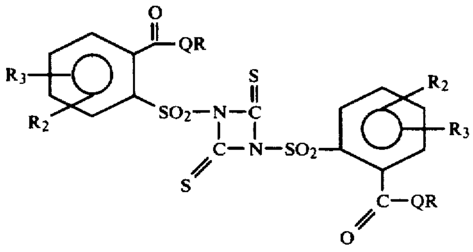

in the same manner as the parent isothiocyanates for the purposes of this invention.

The synthetic method chosen for the preparation of compounds of Formula I depends largely on the substituents R and $R_4$. As shown in Equation 3, compounds of Formula I, wherein Q, R, $R_2$ and $R_3$ are as defined for Equation 1, are conveniently prepared by reacting an appropriately substituted carbonylbenzenesulfonyl isocyanate or isothiocyanate of Formula IIb with an appropriately substituted aminopyrimidine or aminotriazine of Formula III:

Equation 3

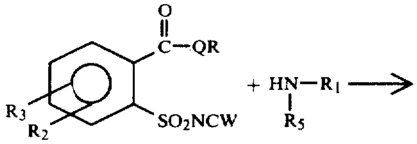

(IIb) (III)

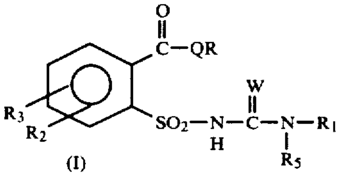

(I)

The reaction of Equation 3 is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of amine III. Since such isocyanates and isothiocyanates are liquids, low melting solids or are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction medium are isolated by evaporation of the solvent, trituration of the solid residue with solvents such as 1-chlorobutane or ethyl ether, and filtration.

As shown in Equation 3A compounds of Formula Ia, wherein R is not H or M, W is S and $R_5$ is H, are alternatively prepared by the reaction of an appropriately substituted o-carbonylbenzenesulfonamide with the appropriate triazine or pyrimidine isothiocyanate of formula IIIA.

Equation 3A

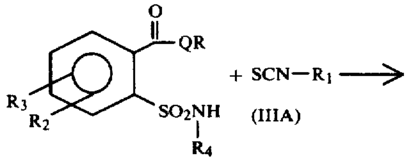

(IIIA)

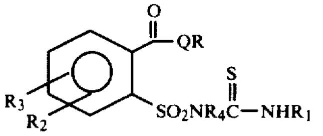

(Ia.)

The reaction of Equation 3A is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 3A are prepared, for example, according to the method of Japan patent Application Pub: Kokai No. 51-143686, June 5, 1976, or that of W. Abraham and G. Barnikow Tetrahedron 29, 691-7 (1973).

As shown in Equation 4, compounds of Formula I, wherein Q is O, S or

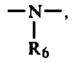

and R is as defined for Equation 1 $R_4$ is methyl and W is O, can be prepared by methylation of salts IV wherein M is an alkali metal cation such as sodium (derived from compounds of Formula I wherein $R_4$ is hydrogen):

Equation 4

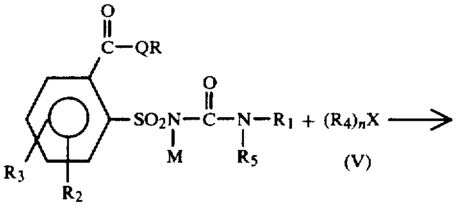

(IV) (V)

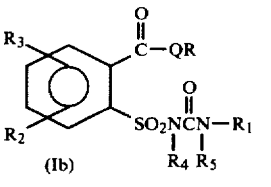

(Ib)

X being an incipient anion and n being an integer corresponding to the valence of X.

The reaction of Equation 4 is best carried out in aprotic organic solvents such as tetrahydrofuran, dimethylformamide, or dimethylacetamide, at ambient pressure and temperature. Methylating agents V, such as dimethyl sulfate or methyl iodide, can be employed. The desired product can be isolated by pouring the reaction mixture into water and filtering off the precipitated solid.

As shown in Equation 5, compounds of Formula Ic, wherein Q is O, S or

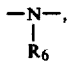

R and $R_4$ are as defined for Equation 4, can also be prepared by the reaction of an appropriately substituted sulfonyl-N-methylcarbamyl chloride or sulfonyl-N-methylthiocarbamyl chloride of Formula VI with an appropirate aminopyrimidine or aminotriazine of Formula III:

Equation 5

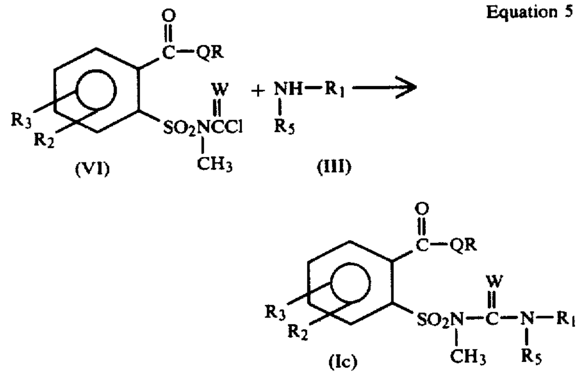

(VI) (III)

(Ic)

The preparation of ureas and thioureas, like those of Formula Ic, from amines and carbamyl chlorides and thiocarbamyl chlorides is well known to the art. The reaction can best be carried out by adding equivalent amounts of the chloride VI and amine III to an inert organic solvent, such as tetrahydrofuran, xylene, or methylene chloride, in the presence of an acid acceptor, such as triethylamine, pyridine, or sodium carbonate employing temperatures from 20°-130°. Soluble products can be isolated by filtering off the precipitated salts and concentration of the filtrate. Insoluble products can be filtered off and washed free of salts with water.

The chlorides of Formula VI can be prepared by phosgenation or thiophosgenation of N-alkylsulfonamide salts. The sulfonamide salt is added to an excess of phosgene or thiophosgene in an inert organic solvent, such as tetrahydrofuran, toluene, or xylene, whereupon, after removal of the excess phosgene, the chloride VI can be isolated or reacted in situ with the amine III.

Compounds of Formula Ie, wherein R is -H, can be prepared by hydrolysis of esters of Formula Id wherein R is $C_1$-$C_{12}$ alkyl. As shown in Equation 6, alkali metal base catalyzed hydrolysis in aqueous methanol produces the alkali metal carboxylate from which the carboxylic acid is obtained by treatment with mineral acids such as HCl:

Equation 6

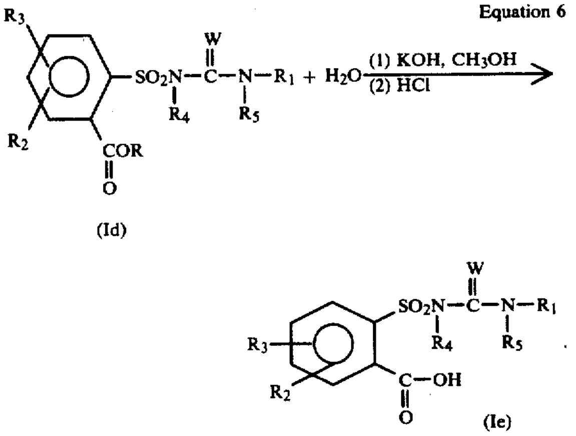

(Id)

(Ie)

The reaction of Equation 6 is best carried out in a solution containing the compound being hydrolyzed, 2 to 10 parts of methanol, 10-50 parts of water and 2-10 equivalents of a base such as sodium or potassium hydroxide maintaining the temperature at 30°-90° C. for 3-24 hours. The reaction yields the soluble alkali metal salt of the carboxylic acid, which is suitable for the purposes of this invention. Conversion of these salts to the acid form is easily carried out by addition to the reaction medium of strong mineral acids, such as hydrochloric or sulfuric acid, causing the desired carboxylic acids to precipitate from solution.

Compounds wherein W and Q are O and R is H can be converted to compounds of this invention where R is a higher alkyl or substituted hydrocarbyl group, as already disclosed herein, by the reaction of salts of the parent acid (R=H) with R-Halogen as shown in Equation 6A.

Equation 6A

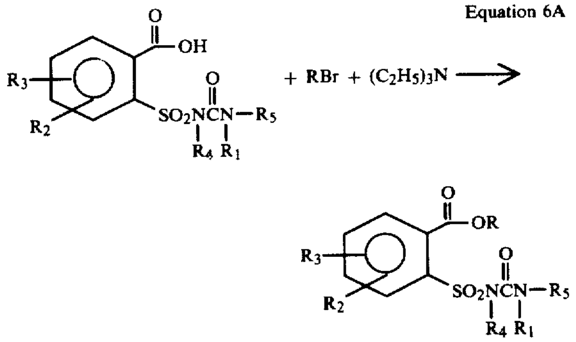

The reaction of Example 6A is of use where the intermediate compound R-Halogen contains a readily replaceable halogen as is the case for substituted or unsubstituted allylic or benzylic halides, α-halonitriles, or α-halocarbonyl compounds.

The procedure of Equation 6A is best carried out in inert polar solvents such as tetrahydrofuran, acetonitrile or acetone by combining the appropriately substituted carboxylic acid and base such as triethylamine or 1,4-diaza—2,2,2]bicyclooctane adding the appropriate halide and heating the mixture to reflux with stirring for 1 to 6 hours. The reaction mixture can be evaporated to dryness and the residue triturated with water, filtered and washed with water to separate the desired product from the water soluble salt.

Certain compounds of Formula I, wherein Q is oxygen, are move conveniently prepared by reaction of the silver salt of the carboxylic acid and the appropriate R group containing a suitable leaving group such as iodide. Thus, a substituted iodobenzene is reacted with the silver carboxylate as in Equation 6B.

Equation 6B

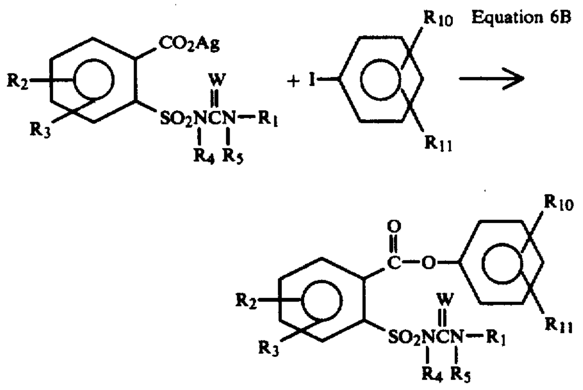

in a suitable solvent such as acetonitrile between 0° and 80° for 1-6 hours.

Esters where R is $C_3$-$C_9$ alkynyl are also conveniently prepared by this method.

The silver salt is prepared by adding an excess of silver nitrate to an aqueous solution of the sodium carboxylate and filtering the precipitate and washing with water.

Compounds of Formula I wherein Y of group $R_1$ contains

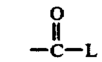

and L is OH can be prepared according to the procedure of Equation 6C wherein R, $R_2$, $R_3$, Q, $R_4$, W, X and $R_5$ are as previously defined.

Equation 6C

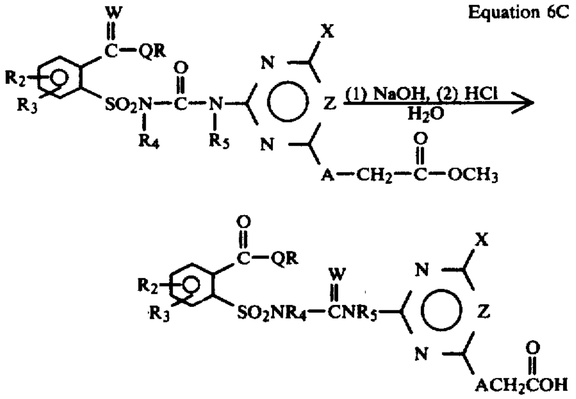

The reaction of Equation 6C is best carried out by suspending the compound being hydrolyzed in 10 to 100 parts of water with enough of a base such as sodium hydroxide or potassium hydroxide to obtain a pH of 10 to 14, ideally, a pH of 12, heating until a clear solution is obtained and then adjusting the pH to 1-3, preferably 3. The product is then caused to precipitate in some instances and can be removed by filtration or it can be extracted into a polar organic solvent such as methylene chloride and isolated by evaporation of the solvent.

When Q is $NR_6$, the compounds can be prepared from the esters of this invention where R is $C_1$-$C_4$ (preferably $C_1$) by the reaction of the esters with dialkylaluminum-N-alkylamide derivatives according to Equation 7, R, $R_1$, $R_2$, $R_3$ and $R_6$ being as previously defined.

Equation 7

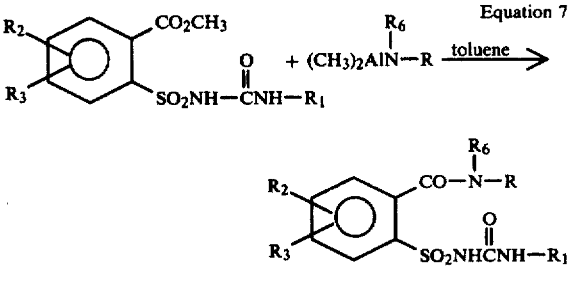

(If)

The intermediate alkylaminoaluminum compounds prepared according to A. Basha, M. Lipton and S. W. Weinreb, *Tetrahedron Letters* 4171 (1977), are co-mingled with a suspension of the esters in toluene or similar inert solvent and the mixture is refluxed for one to six hours. The product can be isolated by evaporation of the solvent toluene, adding methylene chloride and aqueous hydrochloric acid to decompose the residual reaction mass and extracting the desired product into methylene chloride. Evaporation of the methylene chloride yields the desired product in sufficiently pure form for the purpose of this invention.

Compounds of formula IId, wherein Q is $NR_6$ and $R_1$, $R_2$, $R_3$ and $R_4$ are as previously defined in the general formula, which are useful as intermediates in Equation 3A, are prepared as shown in Equation 7A.

Equation 7A

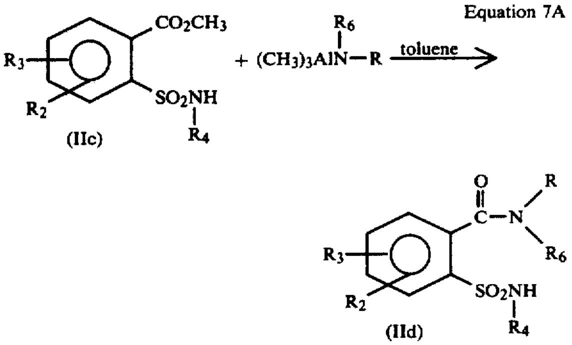

The conditions described for Equation 7 are suitable for the conversion of the esters of formula IIc to the amides IId as shown in Equation 7A.

The products of Equation 7A are especially useful for the preparation of compounds of formula Ia wherein Y has an ester substituent $CO_2(C_1$-$C_6)$, by the route described in Equation 3A.

When Q is S, these compounds can be prepared from the esters of this invention wherein QR is $C_1$-$C_4$ alkoxy (preferably $C_1$) by the reaction of the esters with the appropriate dialkylaluminum alkylthiolate according to Equation 8.

Equation 8

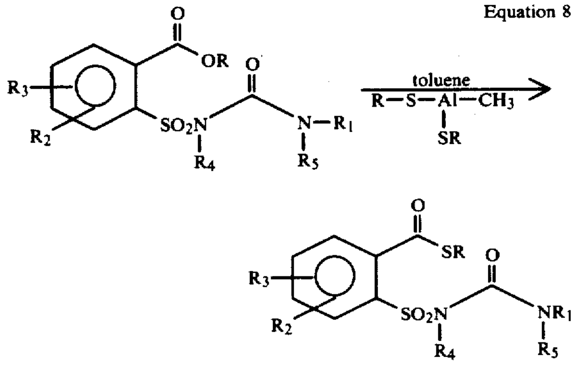

The intermediate aluminum thiolates can be prepared according to R. P. Hatch and S. W. Weinreb, *Journal Of Organic Chemistry*, Vol. 42, 3960 (1977). The reaction of the thiolate with the ester of this invention is best carried out in a neutral solvent such as toluene or xylene at reflux for one to three hours. Best results are obtained when the aluminum thiolate compound is present in excess of the stoichiometric amount required.

Sulfonamides of formula IIb are also converted from carboxylic acid esters to the thiolesters as shown in Equation 8A according to the method of R. P. Hatch and S. W. Weinreb as described for Equation 8 wherein R, $R_2$, $R_3$ and $R_4$ are as previously defined.

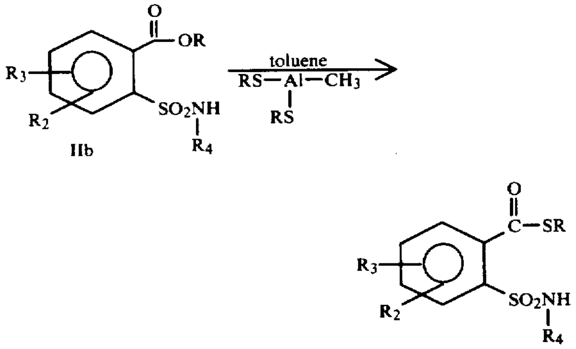

The conditions described for Equation 8 are suitable for the conversion of the sulfonamides of formula IIb as shown in Equation 8A.

The product of Equation 8A are especially useful for the preparation of compounds of formula Ia, wherein Y has a substituent ($CO_2C_1$-$C_6$) by the route described for Equation 3A.

An alternate route to prepare compounds where R is bonded to Q (Q=O) at a secondary carbon involves the reaction of the appropriate dialkylaluminum alcoholate and an ester of this invention wherein R is a lower primary alkyl group, preferably methyl, according to Equation 9.

Equation 9

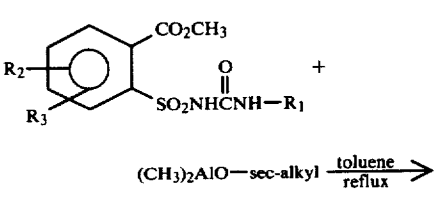

-continued

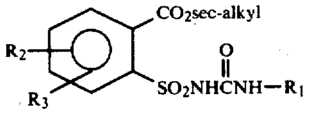

The reaction is carried out in a neutral solvent such as toluene with a boiling point sufficiently high to bring about the desired reaction during reflux. The dialkylaluminum alcoholate being present in greater than an equivalent amount to the ester for best yields. After refluxing for 1-15 hours, the reaction mixture is decomposed with dilute hydrochloric acid and the product extracted into methylene chloride. Evaporation of the methylene chloride yields the desired compound sufficiently pure for the purposes of this invention. The product can be triturated with a solvent, e.g. 1-chlorobutane to remove impurities.

The synthesis of heterocyclic amines has been reviewed in "The Chemistry of Heterocyclic Compounds" a series published by Interscience Publ., New York and London. 2-Aminopyrimidines are described by D. J. Brown in The Pyrimidines, Vol. XVI of this series. The 2-amino-1,3,5-triazines are reviewed by K. R. Huffman and in The Triazines of this same series. The synthesis of triazines are also described by F. C. Schaefer, U.S. Pat. No. 3,154,547 and by K. R. Huffman and F. C. Schaeffer, J. Org. Chem. 28, 1816-1821 (1963).

The preparation of agriculturally suitable salts of the compounds of Formula I, as well as starting materials and intermediates for said compounds, not otherwise described herein, is disclosed in my applications Ser. No. 824,805 filed Aug. 15, 1977 and Ser. No. 840,389 filed Oct. 6, 1977, the contents of which are incorporated herein by reference.

The compounds of this invention and their preparation are further illustrated by the following examples wherein temperatures are given in degrees centigrade and parts by weight unless otherwise indicated.

EXAMPLE 1

Methyl 2-(isocyanatosulfonyl)benzoate

A stirred mixture containing 157 g of methyl 2-sulfamoylbenzoate, 73 g of butyl isocyanate 0.3 g of 1,4-diazabicyclo[2,2,2]octane and 1.0 l of xylene was heated to reflux for one half hour. Phosgene gas was then passed into the system under a dry ice reflux condenser allowing the reaction temperature to drop to 120°. This addition was continued until the reflux temperature remained at 120° without further phosgene addition. The temperature of the reaction mixture was then raised to 136° (by removal of the dry ice reflux condenser) after which it was cooled to room temperature and filtered. Evaporation of the filtrate yielded the desired crude sulfonyl isocyanate which could be purified by distillation at 132°-138° C. under 1.0 to 1.1 mm of mercury pressure. The product is extremely reactive with water so contact with moisture should be scrupulously avoided.

EXAMPLE 2

Isopropyl 2-(isocyanatosulfonyl)benzoate

To 60.7 g (0.25 mole) of isopropyl 2-sulfamoylbenzoate in 300 ml dry (molecular sieves) xylenes was added 25.0 g (0.25 mole) N-butyl isocyanate and 0.1 g 1,4-diazabicyclo[2,2,2]octane. The mixture was heated to reflux temperature and phosgene was slowly bubbled through the solution for 2 hours.

An infrared spectrum of the reaction mixture indicated formation of the desired sulfonylisocyanate (2250 $cm^{-1}$). The resulting cloudy solution was cooled to room temperature and decanted from a small amount of solid impurity. Evaporation of the resulting clear solution yielded the desired crude sulfonyl isocyanate, which was used in subsequent steps without further purification.

EXAMPLE 3

N-[(4,6-Dimethylpyrimidin-2-yl)aminocarbonyl]-2-methoxycarbonylbenzenesulfonamide To 37 g. of 2-amino-4,6-dimethylpyrimidine in 500 ml of anhydrous acetonitrile was added 67 g of 2-methoxycarbonylbenzenesulfonylisocyanate with stirring at ambient temperatures. The resulting mixture was thereafter stirred for sixteen hours and then filtered to remove the desired product which had precipitated as a white solid, m.p. 198°-202°. It showed infrared absorption peaks at 1750, 1700, 1600 and 1550 $cm^{-1}$, consistent for the desired compound.

EXAMPLE 4

N-[(Pyrimidin-2-yl)aminocarbonyl]-2-methoxycarbonylbenzenesulfonamide

With stirring at ambient temperature, 1.0 g of 2-aminopyrimidine in 25 ml of anhydrous acetonitrile was added to 2.4 g of 2-methoxycarbonylbenzenesulfonylisocyanate. After stirring that mixture for 24 hours, the resultant precipitate was filtered off to yield 2.2 g of the desired compound which melted at 188°-192°. Its showing infrared absorption peaks at 1700, 1680 and 1580 $cm^{-1}$ is consistent for N-[(pyrimidin-2-yl)aminocarbonyl]-2-methoxycarbonylbenzenesulfonamide.

EXAMPLE 5

N-[(4-Methoxy-6-methylpyrimidin-2-yl)aminocarbonyl]-2-methoxycarbonylbenzenesulfonamide To a stirred suspension of 1.4 g of 2-amino-4-methoxy-6-methylpyrimidine in 30 ml of anhydrous methylene chloride was added at ambient temperature 2.4 g of 2-methoxycarbonylbenzenesulfonylisocyanate. After stirring for 16 hours, the foregoing mixture was filtered to remove unreacted amine, and the filtrate evaporated at temperatures up to 40° and reduced pressure. The resultant residue was stirred in 25 ml of water, the pH adjusted to 10 by the addition of 50% sodium hydroxide and the solution filtered. Acidification of the filtrate to pH 3 with hydrochloric acid caused precipitation of the desired product which was removed by filtration and dried to yield 0.8 g of product melting at 173°-179°. It showed infrared absorption peaks at 1720, 1680, 1630 and 1550 $cm^{-1}$, consistent for N-[(4-methoxy-6-methylpyrimidin-2-yl)aminocarbonyl]-2-methoxycarbonylbenzenesulfonamide.

EXAMPLE 6

N-[(4,6-Dimethoxypyrimidin-2-yl)aminocarbonyl]-2-methoxycarbonylbenzenesulfonamide A mixture containing 1.6 g of 2-amino-4,6-dimethoxypyrimidine, 30 ml of anhydrous methylene chloride and 2.4 g of 2-methoxycarbonylbenzenesulfonylisocyanate was stirred at ambient temperature and pressure for 16 hours. It was then filtered to remove unreacted amine and the filtrate evaporated at temperatures up to 40° and reduced pressure. The residue thus obtained was stirred in 25 ml of water, the pH adjusted to 10 by the addition of 50% aqueous sodium hydroxide and the solution filtered. Acidification of the filtrate to pH 3 caused the formation of a precipitate. Filtration and drying the precipitate yielded 1.7 g of the desired product, melting at 185°-190°. Its infrared absorption peaks at 1700 and 1710 $cm^{-1}$ are consistent for the desired structure and the nuclear magnetic resonance absorption peaks at 3.8 and 3.85 are consistent for the two different types of methoxy groups brought together in this product.

EXAMPLE 7

2-(Benzyloxycarbonyl)-N-[(4,6-dimethylpyrimidin-2-yl)aminocarbonyl]benzenesulfonamide To 1.75 g of 2-(4,6-dimethylpyrimidin-2-ylaminocarbonylsulfamoyl) benzoic acid was added 0.51 g of triethylamine in 10 ml tetrahydrofuran and 0.88 g of benzyl bromide in 10 ml of tetrahydrofuran. The mixture was heated to reflux for 1.5 hours, filtered and the tetrahydrofuran evaporated in-vacuo. The residue was extracted with hot 1-chlorobutane, diluted with ethyl acetate, washed with water and saturated aqueous sodium bicarbonate. The organic phase was dried over magnesium sulfate, filtered and the solvents evaporated in-vacuo. The resultant residue was crystallized from 1-chlorobutane to a melting point of 157°. This product showed absorption peaks in the infrared region at 1720, 1600, 1560 $cm^{-1}$ consistent for the desired ester and absorption by nuclear magnetic resonance at 2.45δ, singlet, for $CH_3$; 5.3δ singlet, $CH_2$ on benzyl; 6.65δ singlet CH of pyrimidine and aryl peaks at 7-8δ.

By using the procedures of Examples 3-6 with equivalent amounts of 2-aminopyrimidines and appropriately substituted sulfonylisocyanates or isothiocyanates, the compounds of Table I can be prepared.

Alternatively, compounds of Table I wherein R is a group which forms an organohalide with a labile halogen can be prepared by the procedure of Example 7 using equivalent amounts of appropriately substituted benzoic acid derivatives and organohalides.

Compounds of this invention can also be used as intermediates for the preparation of other compounds by methods known to those skilled in the art. For example, nitro substituents can be converted to amino groups by catalytic hydrogenation in the presence of palladium on carbon.

TABLE I

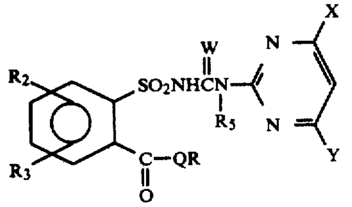

| QR | $R_2$ | $R_3$ | W | $R_5$ | X | Y | m.p. (°C.) |
|---|---|---|---|---|---|---|---|
| $OCH_3$ | H | H | O | H | $CH_3$ | H | |
| $OCH_3$ | 5-F | H | O | H | H | Cl | |
| $OCH_3$ | 5-Cl | H | O | H | $OCH_3$ | $OCH_3$ | 196–198° |
| $OCH_3$ | 5-Br | H | O | H | $CH_3$ | $OCH_3$ | |
| $OCH_3$ | 5-$NO_2$ | H | O | H | $CH_3$ | $OCH_3$ | |
| $OCH_3$ | 5-$OCH_3$ | H | O | H | $CH_3$ | $OCH_3$ | |
| $OCH_3$ | 5-$CH_3$ | H | O | H | $CH_3$ | $CH_3$ | |
| $OCH_3$ | 5-i-$C_3H_7$ | H | O | H | $CH_3$ | $OC_2H_5$ | |
| $OCH_3$ | 5-$SCH_3$ | H | O | H | $CH_3$ | $OCH_3$ | |
| $OCH_3$ | 5-Cl | 3-Cl | O | H | $CH_3$ | $OCH_3$ | |
| $OCH_3$ | 5-Cl | 3-$CH_3$ | O | H | $CH_3$ | $OCH_3$ | |
| $OCH_3$ | 5-F | 3-Cl | O | H | $CH_3$ | $OCH_3$ | |
| $OCH_3$ | 5-$NO_2$ | 3-Cl | O | H | $CH_3$ | $OCH_3$ | |
| $OCH_3$ | 5-Br | 3-Br | O | H | $CH_3$ | $OCH_3$ | |
| $OC_2H_5$ | 6-Cl | H | S | H | $CH_3$ | $CH_2OCH_3$ | |
| $OC_2H_5$ | H | H | O | H | $CH_3$ | $OCH_2CH_2OC_2H_5$ | |
| $OCH_3$ | H | H | O | H | $CH_3$ | $OCH_2CH_2CH_2OCH_3$ | 108–110° |
| $OC_2H_5$ | H | H | O | H | $CH_3$ | $OCH(CH_3)CO_2CH_3$ | |
| $OC_2H_5$ | H | H | O | H | $CH_3$ | $OCH_2CH_2CO_2CH_3$ | |
| $OC_2H_5$ | H | H | O | H | $CH_3$ | $OCH_2CO_2C_2H_5$ | |
| $OCH_3$ | H | H | O | $CH_3$ | $OCH_3$ | $OCH_3$ | |
| $OC_2H_5$ | H | H | O | $CH_3$ | $OCH_3$ | $OCH_3$ | |
| $OCH_3$ | 5-Cl | H | O | $CH_3$ | $OCH_3$ | $CH_3$ | 196–198° |
| $OCH_3$ | 6-Cl | H | O | $CH_3$ | $OCH_3$ | $OC_2H_5$ | |
| $OCH_3$ | 3-$CH_3$ | H | O | $CH_3$ | $OCH_3$ | $OCH_3$ | |
| $OCH_3$ | H | H | O | H | $CH_3$ | $SCH_2COOCH_3$ | |
| $OCH_3$ | H | H | O | H | $CH_3$ | $S(CH_2)_2OC_2H_5$ | 152.5–160° |
| $OCH_3$ | H | H | O | H | $CH_3$ | $S(CH_2)_2COOC_2H_5$ | |
| O—n-$C_3H_7$ | H | H | O | H | $OCH_3$ | $CH_3$ | 177–179° |
| O—n-$C_3H_7$ | H | H | O | H | $OCH_3$ | $OCH_3$ | 160–165° |
| O—$C_2H_5$ | H | H | O | H | $OCH_3$ | $CH_3$ | 168–170° |
| O—$CHCH_2CH_3$<br>\|<br>$CH_3$ | H | H | O | H | $OCH_3$ | $CH_3$ | 120–124° |
| O—CH—$CH_2CH_3$<br>\|<br>$CH_3$ | H | H | O | H | $OCH_3$ | $OCH_3$ | 152–155° |
| $OCH_2CH_2Cl$ | H | H | O | H | $OCH_3$ | $CH_3$ | 150–154° |
| $OCH_2CH_2Cl$ | H | H | O | H | $OCH_3$ | $OCH_3$ | 157–160° |
| $O(CH_2)_9CH_3$ | H | H | O | H | $OCH_3$ | $CH_3$ | 98–101° |
| $O(CH_2)_9CH_3$ | H | H | O | H | $OCH_3$ | $OCH_3$ | 87–90° |
| O— 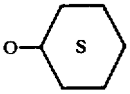 | H | H | O | H | $OCH_3$ | $OCH_3$ | 170–172° |
| $OCH_3$ | 4-Cl | H | O | H | $OCH_3$ | $CH_3$ | 166–168° |
| $OCH_3$ | 4-Cl | H | O | H | $OCH_3$ | $OCH_3$ | 158–160° |
| O—i-$C_3H_7$ | H | H | O | H | $OCH_3$ | $CH_3$ | 175–179° |
| O—i-$C_3H_7$ | H | H | O | H | $OCH_3$ | $OCH_3$ | 189–190° |
| O—n-$C_4H_9$ | H | H | O | H | $OCH_3$ | $CH_3$ | 124–126° |
| O—n-$C_4H_9$ | H | H | O | H | $OCH_3$ | $OCH_3$ | 140–149° |
| $OC_2H_5$ | H | H | O | H | $OCH_3$ | $OCH_3$ | 149–153° |
| $O(CH_2)_9CH_3$ | H | H | O | H | $CH_3$ | $OCH_2CF_3$ | |
| $OCH(CH_2)_4CH_3$<br>\|<br>$CH_2CH_3$ | H | H | O | H | $CH_3$ | $CH_3$ | |
| $OCH_2CH_2Cl$ | H | H | O | H | $CH_3$ | $OCH_2CO_2CH_3$ | |
| $OCH_2CH_2CH_2Cl$ | H | H | O | H | $OCH_3$ | $CH_3$ | |

TABLE I-continued

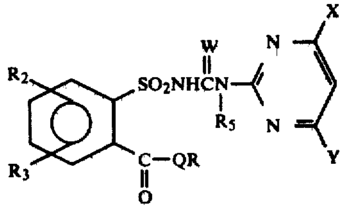

| QR | $R_2$ | $R_3$ | W | $R_5$ | X | Y | m.p. (°C.) |
|---|---|---|---|---|---|---|---|
| $O-CHCH_2Cl$<br>$CH_3$ | H | H | O | H | $OCH_3$ | $CH_3$ | 100–104° |
| $OCH_2CH_2CH_2CH_2Cl$ | H | H | O | H | $CH_3$ | $CH_3$ | |
| $OCH_2(CH_2)_4CH_2Cl$ | H | H | O | H | $CH_3$ | $CH_3$ | |
| $OCH_2CH=CH_2$<br>$Cl$ | H | H | O | H | $CH_3$ | $CH_3$ | |
| $O-CHCH_2Cl$<br>$CH_2Cl$ | H | H | O | H | $CH_3$ | $CH_3$ | |
| $OCH_2CCl_3$ | H | H | O | H | $OCH_3$ | $CH_3$ | |
| $OCH_2CF_3$ | H | H | O | H | $CH_3$ | $CH_3$ | |
| $OCH_2CH_2Br$ | H | H | O | H | $CH_3$ | $CH_3$ | |
| $OCH_2CH_2CH_2OCH_3$ | H | H | O | H | $OCH_3$ | $CH_3$ | |
| $O(CH_2CH_2O)_2C_2H_5$ | H | H | O | H | $OCH_3$ | $CH_3$ | |
| $OCH_2CH=CH_2$ | H | H | O | H | $CH_3$ | $CH_3$ | |
| $O(CH_2)_4CH=CH_2$ | H | H | O | H | $OCH_3$ | $CH_3$ | |
| $OCH(CH_2)_2CH=CH_2$<br>$CH_3$ | H | H | O | H | $CH_3$ | $CH_3$ | |
| $OCH_3$ | 4-Cl | 5-Cl | O | H | $OCH_3$ | $CH_3$ | 193–194° |
| $OCH_3$ | 4-Cl | 5-Cl | O | H | $OCH_3$ | $OCH_3$ | 202–204° |
| $OCH_3$ | 4-F | H | O | H | $OCH_3$ | $CH_3$ | 201–203° |
| $OCH_3$ | 4-Br | H | O | H | $OCH_3$ | $CH_3$ | |
| $O-CH_2CH(CH_3)_2$ | H | H | O | H | $OCH_3$ | $CH_3$ | 108–111° |
| $O-CH_2CH(CH_3)_2$ | H | H | O | H | $OCH_3$ | $OCH_3$ | 166–168° |
| $O(CH_2)_4CH_3$ | H | H | O | H | $OCH_3$ | $CH_3$ | 87–89° |
| $OCHCH_2CH_3$<br>$CH_3$ | H | H | O | H | $OCH_3$ | $CH_3$ | 130–132° |
| $OCHCH_2CH_3$<br>$CH_2CH_3$ | H | H | O | H | $CH_3$ | $OCH_3$ | 153–155° |
| $OCH_2CHCH_2CH_3$<br>$CH_3$ | H | H | O | H | $OCH_3$ | $CH_3$ | |
| $OCH\ CHCH_3$<br>$CH_3CH_3$ | H | H | O | H | $CH_3$ | $CH_3$ | |
| $OCH_2CBr_3$ | H | H | O | H | $CH_3$ | $CH_3$ | |
| $OCHCH_2Cl$<br>$CH_2F$ | H | H | O | H | $CH_3$ | $CH_3$ | |
| $OCH_3$ | H | H | O | H | $CH_3$ | O $CH_3$<br>$OCH_2CN$<br>H | |
| $OCH_3$ | H | H | O | H | $CH_3$ | O $CH_3$<br>$OCH_2-CN$<br>$CH_3$ | |

TABLE I-continued

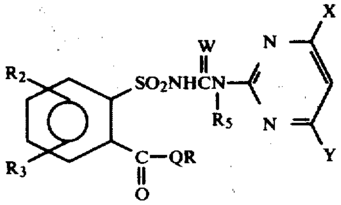

| QR | $R_2$ | $R_3$ | W | $R_5$ | X | Y | m.p. (°C.) |
|---|---|---|---|---|---|---|---|
| $OCH_3$ | H | H | O | H | $CH_3$ | 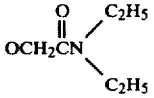 | |
| $OCH_3$ | H | H | O | H | $CH_3$ | 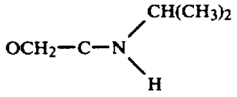 | |
| $OCH_3$ | H | H | O | H | $CH_3$ | 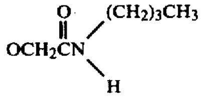 | |
| $OCH_3$ | H | H | O | H | $OCH_3$ | 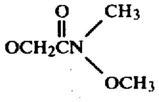 | |
| $OCH_3$ | H | H | O | H | $CH_3$ | 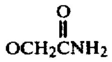 | |
| 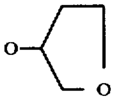 | H | H | O | H | $OCH_3$ | $CH_3$ | 105-110° |
| 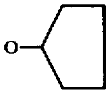 | H | H | O | H | $OCH_3$ | $CH_3$ | |
| $OCH_2CH_2OCH_2CH_3$ | H | H | O | H | $OCH_3$ | $CH_3$ | 130-134° |
| $OCH_2CH_2OCH_2CH_3$ | H | H | O | H | $OCH_3$ | $OCH_3$ | 163-166° |
| O—i-$C_3H_7$ | H | H | O | H | $CH_3$ | $CH_3$ | 194-196° |
| $OCH_3$ | 4-F | H | O | H | $OCH_3$ | $OCH_3$ | 200-202° |
| $OCH_2CH_2CH(CH_3)_2$ | H | H | O | H | $OCH_3$ | $CH_3$ | 121-124° |
| $OCH_2CH_2CH(CH_3)_2$ | H | H | O | H | $OCH_3$ | $OCH_3$ | 151-153° |
| $OCH_2CH_2CH(CH_3)_2$ | H | H | O | H | $CH_3$ | $CH_3$ | 90-93° |
| $OCH_2CH_2OCH_2CH_3$ | H | H | O | H | Cl | Cl | 122-126° |
| o-i-$C_3H_7$ | H | H | O | H | $CH_3$ | $OCH_2CH_2OCH_3$ | oil |
| $OCH_3$ | H | H | O | H | $CH_3$ | $OCH_2CF_3$ | 156-160° |
| $OCH_3$ | H | H | O | H | $CH_3$ | 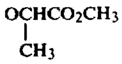 | 143-155° |
| $OCH_3$ | H | H | O | H | $CH_3$ | $OCH_2CO_2CH_3$ | 174-180° |
| $OCH_3$ | H | H | O | H | $CH_3$ | $CH_2OCH_3$ | 154-156° |
| $OCH_3$ | H | H | O | $CH_3$ | $CH_3$ | $CH_3$ | 159-174° |
| $OCH_2(CH_2)_3CH_3$ | H | H | O | H | $CH_3$ | Cl | 61-64° |
| $OCH_2(CH_2)_3CH_3$ | H | H | O | H | $CH_3$ | $CH_2OCH_3$ | oil $n_D^{25}$1.5408 |
| $OCH_3$ | H | H | O | H | $CH_3$ | $OCH_2CH_2OCH_3$ | 118-120° |
| $O(CH_2)_{11}CH_3$ | H | H | O | H | $CH_3$ | $OCH_3$ | |
| 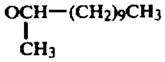 | H | H | O | H | $CH_3$ | $OCH_3$ | |
| 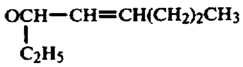 | H | H | O | H | $CH_3$ | $OCH_3$ | |

TABLE I-continued

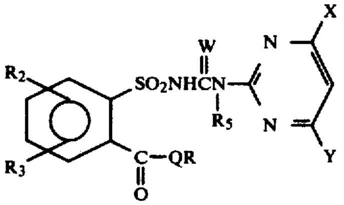

| QR | $R_2$ | $R_3$ | W | $R_5$ | X | Y | m.p. (°C.) |
|---|---|---|---|---|---|---|---|
| $OCH(CH_2)_7CH_3$<br>\|<br>$CH_2CH_2CH_3$ | H | H | O | H | $CH_3$ | $OCH_3$ | |
| $OCH_2C{=}CHCH(CH_3)_2$<br>\|<br>Cl | H | H | O | H | $CH_3$ | $OCH_3$ | |
| $OCH_2CH{=}CCl_2$ | H | H | O | H | $CH_3$ | $OCH_3$ | |
| $OCHCH{=}CF_2$<br>\|<br>$CH_3$ | H | H | O | H | $CH_3$ | $OCH_3$ | |
| $OCHCH{=}CBr_2$<br>\|<br>$CH_3$ | H | H | O | H | $CH_3$ | $OCH_3$ | |
| $O(CH_2)_4CH_3$ | H | H | O | H | $OCH_3$ | $OCH_3$ | 132–134° |
| $O(CH_2)_5CH_3$ | H | H | O | H | $OCH_3$ | $OCH_3$ | 134–136° |
| 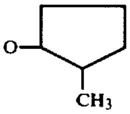 | H | H | O | H | $CH_3$ | $CH_3$ | |
| 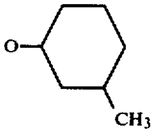 | H | H | O | H | $CH_3$ | $OCH_3$ | |
| 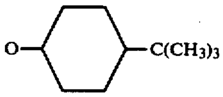 | H | H | O | H | $CH_3$ | $OCH_3$ | |
| 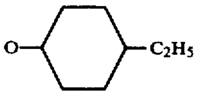 | H | H | O | H | $CH_3$ | $OCH_3$ | |
| 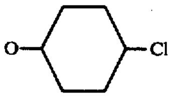 | H | H | O | H | $CH_3$ | $OCH_3$ | |
| O—cyclo $C_8H_{15}$ | H | H | O | H | $CH_3$ | $CH_3$ | |
| 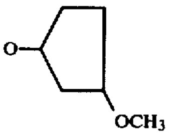 | H | H | O | H | $CH_3$ | $CH_3$ | |

TABLE I-continued
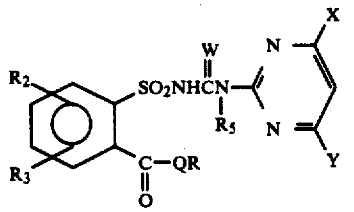
| QR | $R_2$ | $R_3$ | W | $R_5$ | X | Y | m.p. (°C.) |
|---|---|---|---|---|---|---|---|
| 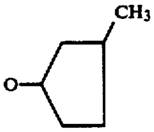 | H | H | O | H | $CH_3$ | $CH_3$ | |
| 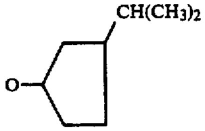 | H | H | O | H | $CH_3$ | $CH_3$ | |
| 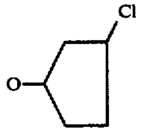 | H | H | O | H | $CH_3$ | $CH_3O$ | |
| 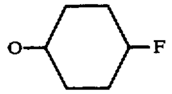 | H | H | O | H | $CH_3$ | $CH_3$ | |
| $OCH_3$ | H | H | O | H | $CH_3$ | $N_3$ | 173-176° |
| 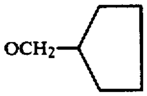 | H | H | O | H | $CH_3$ | $CH_3O$ | |
| 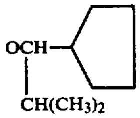 | H | H | O | H | $CH_3$ | $CH_3$ | |
| 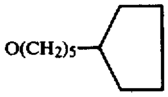 | H | H | O | H | $CH_3$ | $CH_3O$ | |
| 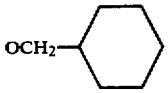 | H | H | O | H | $CH_3$ | $OCH_3$ | |
| 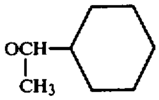 | H | H | O | H | $CH_3$ | $CH_3$ | |
| 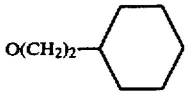 | H | H | O | H | $OCH_3$ | $OCH_3$ | |

TABLE I-continued

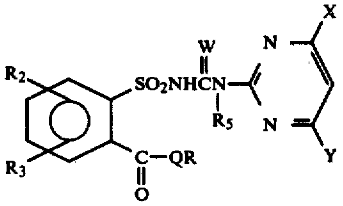

| QR | R₂ | R₃ | W | R₅ | X | Y | m.p. (°C.) |
|---|---|---|---|---|---|---|---|
| 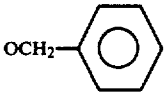 | H | H | O | H | $CH_3$ | $OCH_3$ | |
| 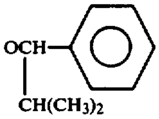 | H | H | O | H | $CH_3$ | $OCH_3$ | |
| 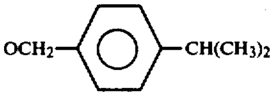 | H | H | O | H | $CH_3$ | $OCH_3$ | |
| 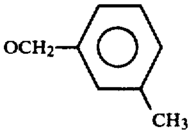 | H | H | O | H | $CH_3$ | $OCH_3$ | |
| 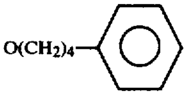 | H | H | O | H | $CH_3$ | $OCH_3$ | |
| 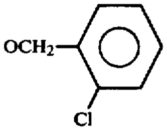 | H | H | O | H | $CH_3$ | $OCH_3$ | |
| $O(CH_2CH_2O)_4CH_3$ | H | H | O | H | $CH_3$ | $OCH_3$ | |
| $O(CH_2CH_2O)_2C_2H_4Cl$ | H | H | O | H | $CH_3$ | $OCH_3$ | $n_D^{25}1.5458$ |
| $OCH_2CH_2CH_2OCH(CH_3)_2$ | H | H | O | H | $CH_3$ | $CH_3$ | |
| $OCH_2CH_2SCH_3$ | H | H | O | H | $CH_3$ | $CH_3$ | |
| $O(CH_2)_3SC_2H_5$ | H | H | O | H | $CH_3$ | $CH_3$ | |
| $OCH_2CH_2SOCH_3$ | H | H | O | H | $CH_3$ | $CH_3$ | |
| $OCH_2CH_2SO_2C_2H_5$ | H | H | O | H | $CH_3$ | $CH_3$ | |
| $O(CH_2)_3SO_2C_2H_5$ | H | H | O | H | $CH_3$ | $CH_3$ | |
| $OCH_2CH_2OC_2H_4Cl$ | H | H | O | H | $CH_3$ | $OCH_3$ | 124–127° |
| $O(CH_2CH_2O)_2C_2H_4Cl$ | H | H | O | H | $OCH_3$ | $OCH_3$ | $n_D^{25}1.5421$ |
| $OCH_2CH{=}CH_2$ | H | H | O | H | $OCH_3$ | $CH_3$ | 129–131° |
| $OCH_2CH{=}CH_2$ | H | H | O | H | $OCH_3$ | $OCH_3$ | 142–145° |
| 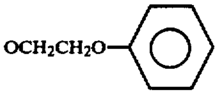 | H | H | O | H | $OCH_3$ | $OCH_3$ | 114–117° |
| 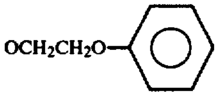 | H | H | O | H | Cl | Cl | 65–69° |

TABLE I-continued

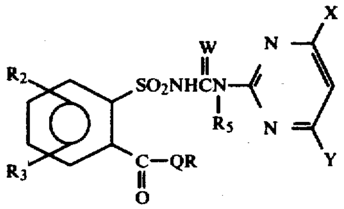

| QR | $R_2$ | $R_3$ | W | $R_5$ | X | Y | m.p. (°C.) |
|---|---|---|---|---|---|---|---|
| 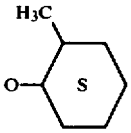 | H | H | O | H | $OCH_3$ | $CH_3$ | 153–156° |
| $OCH_3$ | 5-$CF_3$ | H | O | H | $CH_3$ | $OCH_3$ | |
| $OCH_3$ | 5-$N(CH_3)_2$ | H | O | H | $CH_3$ | $OCH_3$ | |
| $OCH_3$ | 5-$SO_2CH_3$ | H | O | H | $CH_3$ | $OCH_3$ | |
| $OCH_3$ | 5-CN | H | O | H | $CH_3$ | $OCH_3$ | |
| $OCH_3$ | 5-$NH_2$ | H | O | H | $CH_3$ | $OCH_3$ | |
| $OCH_3$ | H | H | O | H | $OCH_2CH_2OCH_3$ | $OCH_2CH_2OCH_3$ | 150–152° |
| $OCH_3$ | H | H | O | H | $-OCH_3$ | n-$C_4H_9$ | |
| $OCH_3$ | H | H | O | H | $-OCH_3$ | $-CH_2CH_2CH_2OCH_2CH_3$ | |
| $OCH_3$ | H | H | O | H | $-OCH_3$ | $-CH_2CH_2CN$ | |
| $OCH_3$ | H | H | O | H | $-OCH_3$ | $-(CH_2)_4CN$ | |
| $OCH_3$ | H | H | O | H | $-OCH_3$ | $-CH_2CO_2CH_3$ | |
| $OCH_3$ | H | H | O | H | $-OCH_3$ | $-CCl_3$ | |
| $OCH_3$ | H | H | O | H | $-OCH_3$ | $-CH-CO_2CH_3$<br>$\vert$<br>$CH_3$ | |
| $OCH_3$ | H | H | O | H | $CH_3$ | $-(CH_2)_3CH_2Cl$ | |
| $OCH_3$ | H | H | O | H | $-OCH_3$ | $-CH_2C\equiv C-CH_3$ | |
| $OCH_3$ | H | H | O | H | $-OCH_3$ | $-CH_2C\equiv C-CH_2Cl$ | |
| $OCH_3$ | H | H | O | H | $-OCH_3$ | $-NHnC_4H_9$ | |
| $OCH_3$ | H | H | O | H | $-OCH_3$ | $-N-(CH_2)_4CN$<br>$\vert$<br>$CH_3$ | |
| $OCH_3$ | H | H | O | H | $-OCH_3$ | $-NCH_2CO_2CH_3$<br>$\vert$<br>$CH_3$ | |
| $OCH_3$ | H | H | O | H | $-OCH_3$ | $-NH(CH_2)_4CO_2C_2H_5$ | |
| $OCH_3$ | H | H | O | H | $-CH_3$ | $-NCH_2CH_2CH_2OCH_2CH_3$<br>$\vert$<br>$CH_3$ | |
| $OCH_3$ | H | H | O | H | $-OCH_3$ | 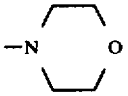 | |
| $OCH_3$ | H | H | O | H | $-CH_3$ | $-O(CH_2)_3CH_3$ | |
| $OCH_3$ | H | H | O | H | $-CH_3$ | $-OCH_2CH_2Br$ | |
| $OCH_3$ | H | H | O | H | $-CH_3$ | $-OCH_2CCl_3$ | |
| $OCH_3$ | H | H | O | H | $-CH_3$ | $-OCH_2CH_2CH_2CN$ | |
| $OCH_3$ | H | H | O | H | $-CH_3$ | $-OCH_2CH=CH_2$ | |
| $OCH_3$ | H | H | O | H | $-CH_3$ | $SCH-CO_2CH_3$<br>$\vert$<br>$CH_3$ | |
| $OCH_3$ | H | H | O | H | $-CH_3$ | $OCH_2CO_2n-C_6H_{13}$ | |
| $OCH_3$ | H | H | O | H | $-CH_3$ | $-SCH_2CH_2CO_2n-C_6H_{13}$ | |
| $OCH_3$ | H | H | O | H | $-CH_3$ | $-OCH_2CH_2OCH(CH_3)_2$ | |
| $OCH_3$ | H | H | O | H | $-CH_3$ | $-SCH_2CH_2SCH_3$ | |
| $OCH_3$ | H | H | O | H | $-CH_3$ | O<br>‖<br>$-SCH_2CH_2SCH_3$<br>‖<br>O | |

TABLE I-continued
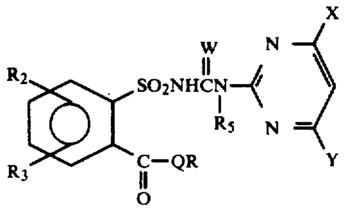
| QR | $R_2$ | $R_3$ | W | $R_5$ | X | Y | m.p. (°C.) |
|---|---|---|---|---|---|---|---|
| $OCH_3$ | H | H | O | H | $-CH_3$ | $-SCH_2CH_3$ | |
| $OCH_3$ | H | H | O | H | $-CH_3$ | $-SCH_2C{\equiv}CH$ | |
| 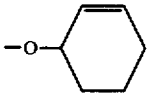 | H | H | O | H | $OCH_3$ | $CH_3$ | 158–160° |
| 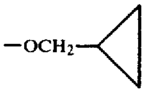 | H | H | O | H | $OCH_3$ | $CH_3$ | |
| 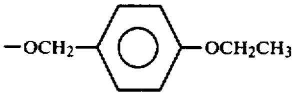 | H | H | O | H | $OCH_3$ | $CH_3$ | |
| 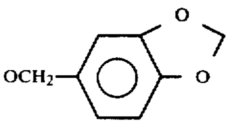 | H | H | O | H | $OCH_3$ | $CH_3$ | |
| 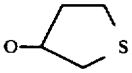 | H | H | O | H | $OCH_3$ | $CH_3$ | |
| 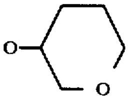 | H | H | O | H | $OCH_3$ | $CH_3$ | |
| 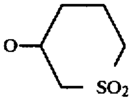 | H | H | O | H | $OCH_3$ | $OCH_3$ | |
| 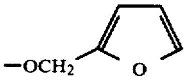 | H | H | O | H | $OCH_3$ | $CH_3$ | |
| 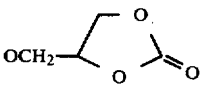 | H | H | O | H | $OCH_3$ | $CH_3$ | |
| 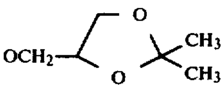 | H | H | O | H | $OCH_3$ | $OCH_3$ | |
| 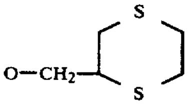 | H | H | O | H | $OCH_3$ | $CH_3$ | |

TABLE I-continued

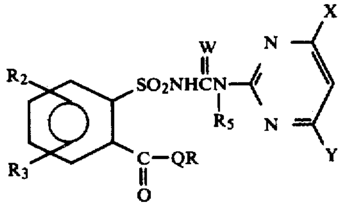

| QR | $R_2$ | $R_3$ | W | $R_5$ | X | Y | m.p. (°C.) |
|---|---|---|---|---|---|---|---|
| $OCH_2$— 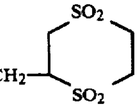 | H | H | O | H | $OCH_3$ | $CH_3$ | |
| 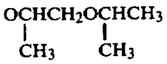 | H | H | O | H | $OCH_3$ | $CH_3$ | |
| 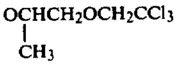 | H | H | O | H | $OCH_3$ | $CH_3$ | |
| $O(CH_2CH_2O)_2-CH(CH_3)_2$ | H | H | O | H | $OCH_3$ | $CH_3$ | |
| $O(CH_2CH_2O)_2$— 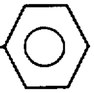 | H | H | O | H | $OCH_3$ | $CH_3$ | |
| 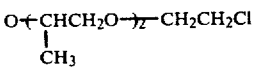 | H | H | O | H | $OCH_3$ | $CH_3$ | |
| $OCH_2CH_2S$— 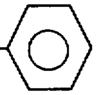 | H | H | O | H | $OCH_3$ | $CH_3$ | |
| $OCH_2CH_2CH_2O$— 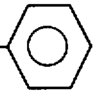 | H | H | O | H | $OCH_3$ | $CH_3$ | |
| 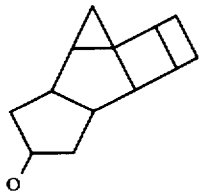 | H | H | O | H | $OCH_3$ | $CH_3$ | |
| 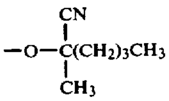 | H | H | O | H | $OCH_3$ | $CH_3$ | |
| 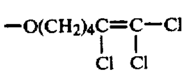 | H | H | O | H | $OCH_3$ | $CH_3$ | |
| $OCH_3$ | H | H | O | H | $CH_3$ | $CO_2CH_3$ | |
| $OCH_3$ | H | H | O | H | $CH_3$ | $CO_2H$ | |
| $OCH_3$ | 5-$NO_2$ | H | O | H | $CH_3$ | $CH_3$ | 105–110° |
| $OCH_3$ | 5-$NO_2$ | H | O | H | $CH_3$ | $OCH_3$ | 80–90° |
| $OCH_3$ | 5-$NO_2$ | H | O | H | $OCH_3$ | $OCH_3$ | 210–212° |
| $OCH_3$ | 5-$NH_2$ | H | O | H | $CH_3$ | $OCH_3$ | 130° |
| $OCH_3$ | 5-$NH_2$ | H | O | H | $OCH_3$ | $OCH_3$ | 135° |
| $OCH_2CH=CH_2$ | H | H | O | H | $CH_3$ | $CH_3$ | 178–180° |
| $OCH_3$ | 5-Cl | H | O | H | $CH_3$ | $CH_3$ | 193–196° |
| $OCH_3$ | H | H | O | H | $CH_3$ | SCN | 101–112° |
| $OCH_2CH=CH_2$ | 5-Cl | H | O | H | $OCH_3$ | $OCH_3$ | 155–157° |

TABLE I-continued

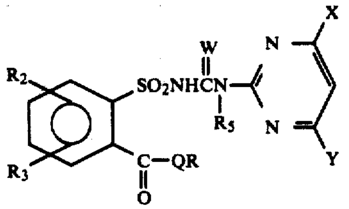

| QR | R2 | R3 | W | R5 | X | Y | m.p. (°C.) |
|---|---|---|---|---|---|---|---|
| $OCH_2CH=CH_2$ | 5-Cl | H | O | H | $OCH_3$ | $CH_3$ | 151-153° |
| $OCH_2CH=CH_2$ | 5-Cl | H | O | H | $CH_3$ | $CH_3$ | 155-157° |
| 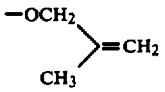 | H | H | O | H | $CH_3$ | $OCH_3$ | 137-140° |
| $OCH_2C≡C-CH_2Cl$ | H | H | O | H | $CH_3$ | $OCH_3$ | 183-185° |
| O—i-$C_3H_7$ | 5-Cl | H | O | H | $OCH_3$ | $OCH_3$ | 194-195° |
| O—i-$C_3H_7$ | 5-Cl | H | O | H | $CH_3$ | $OCH_3$ | 176-178° |
| O—i-$C_3H_7$ | 5-Cl | H | O | H | $CH_3$ | $CH_3$ | 190-192° |
| $CH_3$<br>$OCH_2-C=CH_2$ | H | H | O | H | $OCH_3$ | $OCH_3$ | 150-155° |
| $CH_3$<br>$OCH_2-C=CH_2$ | H | H | O | H | $CH_3$ | $CH_3$ | 140-144° |
| $CH_3$<br>$OCH_2-C=CH_2$ | H | H | O | H | $CH_3$ | $OCH_3$ | 139-142° |
| $OCH_3$ | H | H | O | H | $OC_2H_5$ | $OC_2H_5$ | 138-141° |
| 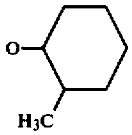 | H | H | O | H | $OCH_3$ | $OCH_3$ | 151-153° |
| 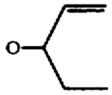 | H | H | O | H | $OCH_3$ | $OCH_3$ | 153-155° |
| 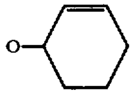 | H | H | O | H | $OCH_3$ | $OCH_3$ | 142-145° |
| $OCH_2CN$ | H | H | O | H | $OCH_3$ | $OCH_3$ | 184-187° |
| $OCH_2-C≡C-C_2H_5$ | H | H | O | H | $CH_3$ | $CH_3$ | |
| $OCH_2-C≡C(CH_2)_5H$ | H | H | O | H | $CH_3$ | $CH_3$ | |
| $OCH_2-C≡C(CH_2)_7H$ | H | H | O | H | $OCH_3$ | $CH_3$ | |
| $OCHCO_2CH_3$<br>$CH_3$ | H | H | O | H | $CH_3$ | $CH_3$ | |
| $OCH_2CO_2C_2H_5$ | H | H | O | H | $CH_3$ | $CH_3$ | |
| $OCH_2CN$ | H | H | O | H | $CH_3$ | $CH_3$ | |
| $OCH_2CH_2CH_2CN$ | H | H | O | H | $CH_3$ | $CH_3$ | |
| $O(CH_2)_5CN$ | H | H | O | H | $CH_3$ | $CH_3$ | |
| $OCH-C≡C-CH_2Cl$ | H | H | O | H | $CH_3$ | $CH_3$ | |
| $OCH-C≡C(CH_2)_2Cl$ | H | H | O | H | $CH_3$ | $CH_3$ | |
| 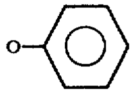 | H | H | O | H | $CH_3$ | $CH_3$ | |

TABLE I-continued

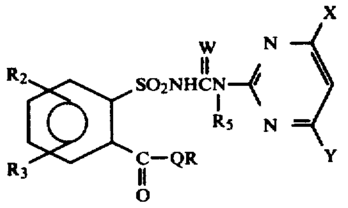

| QR | $R_2$ | $R_3$ | W | $R_5$ | X | Y | m.p. (°C.) |
|---|---|---|---|---|---|---|---|
| 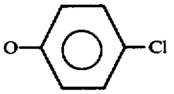 | H | H | O | H | $CH_3$ | $CH_3$ | |
| 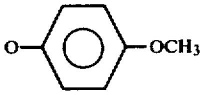 | H | H | O | H | $CH_3$ | $CH_3$ | |
| 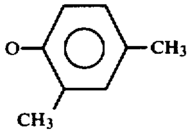 | H | H | O | H | $CH_3$ | $CH_3$ | |
| $OCH_2OCH_3$ | H | H | O | H | $CH_3$ | $CH_3$ | |
| $OCH_2OC_2H_5$ | H | H | O | H | $CH_3$ | $CH_3$ | |
| $OCH_2OCH(CH_3)_2$ | H | H | O | H | $CH_3$ | $CH_3$ | |
| $OCH_2OCH_2CH_2Cl$ | H | H | O | H | $CH_3$ | $CH_3$ | |
| $OCH_2OCH_2CCl_3$ | H | H | O | H | $CH_3$ | $CH_3$ | |
| 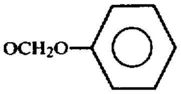 | H | H | O | H | $CH_3$ | $CH_3$ | |
| 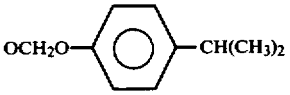 | H | H | O | H | $CH_3$ | $CH_3$ | |
| 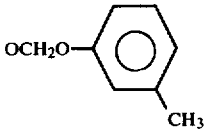 | H | H | O | H | $CH_3$ | $CH_3$ | |
| 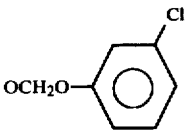 | H | H | O | H | $CH_3$ | $CH_3$ | |
| $OCH_2OCH_2CH_2OCH_3$ | H | H | O | H | $CH_3$ | $CH_3$ | |
| $OCH_2OCH_2CH_2OCH_2CH_3$ | H | H | O | H | $CH_3$ | $CH_3$ | |
| $OCH_3$ | H | H | O | H | $CH_3$ | F | |
| $OCH_3$ | H | H | O | H | $CH_3$ | Br | |
| $OCH_3$ | H | H | O | H | $CH_3$ | $CO_2CH_3$ | |
| $OCH_3$ | H | H | O | H | $OCH_3$ | $CH_2CO_2CH_3$ | |
| $OCH_3$ | H | H | O | H | $OCH_3$ | $CH_2CO_2H$ | |
| $OCH_3$ | H | H | O | H | $OCH_3$ | $CH_2CO_2$—n-$C_4H_9$ | |
| $OCH_3$ | H | H | O | H | $OCH_3$ | $(CH_2)_3CO_2$—i-$C_3H_7$ | |
| $OCH_3$ | H | H | O | H | $OCH_3$ | $CH_2CO_2$—n-$C_6H_{13}$ | |
| $OCH_3$ | H | H | O | H | $OCH_3$ | 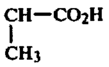 | |

TABLE I-continued

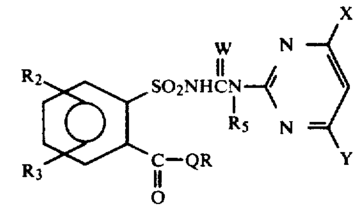

| QR | $R_2$ | $R_3$ | W | $R_5$ | X | Y | m.p. (°C.) |
|---|---|---|---|---|---|---|---|
| $OCH_3$ | H | H | O | H | $CH_3$ | 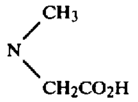 | |
| $OCH_3$ | H | H | O | H | $CH_3$ | $NH(CH_2)_2CO_2$—i-$C_3H_7$ | |
| $OCH_3$ | H | H | O | H | $CH_3$ | 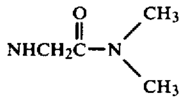 | |
| $OCH_3$ | H | H | O | H | $CH_3$ | 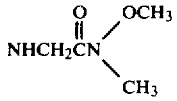 | |
| $OCH_3$ | H | H | O | H | $CH_3$ | 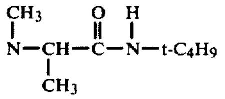 | |
| $OCH_3$ | H | H | O | H | $CH_3$ | 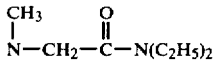 | |
| $OCH_3$ | H | H | O | H | $CH_3$ | 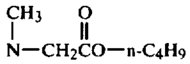 | |
| $OCH_3$ | H | H | O | H | $CH_3$ | 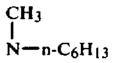 | |

EXAMPLE 8

N-[(4,6-dimethoxy-1,3,5-triazin-2-yl)aminocarbonyl]-2-(2-chloroethoxycarbonyl)benzenesulfonamide To 0.7 g of 2-amino-4,6-dimethoxy-1,3,5-triazine in 10 ml anhydrous methylene chloride solvent was added 1.45 g 2-(β-chloroethoxycarbonyl)benzenesulfonyl isocyanate. After stirring at ambient temperature for sixteen hours the solvent was removed under reduced pressure, the residue triturated with ether and the solid product filtered off, yield 1.21 g m.p. 171°-174° C. The solid showed infrared absorption peaks at 1705 and 1715 $cm^{-1}$, consistent for N-[(4,6-dimethoxy-1,3,5-triazin-2-yl)aminocarbonyl]-2-(2-chloroethoxycarbonyl)benzenesulfonamide.

EXAMPLE 9

N-[(4-methoxy-6-methyl-1,3,5-triazin-2-yl)aminocarbonyl]-2-(2-chloroethoxycarbonyl)benzenesulfonamide To 0.7 g of 2-amino-4-methoxy-6-methyl-1,3,5-triazine in 10 ml anhydrous methylene chloride solvent was added 1.45 g 2-(β-chloroethoxycarbonyl)benzenesulfonyl isocyanate with stirring at ambient temperature. The mixture was thereafter stirred for sixteen hours. The solvent was evaporated under reduced pressure and the residue triturated with hexane and filtered to yield 1.72 g of compound which melted at 167°-170° C. The solid showed infrared absorption peaks at 1700 and 1705 $cm^{-1}$, consistent for N-[(4-methoxy-6-methyl-1,3,5-triazin-2-yl)aminocarbonyl]-2-(2-chloroethoxycarbonyl)benzenesulfonamide.

EXAMPLE 10

N-[(4,6-dimethoxy-1,3,5-triazin-2-yl)aminocarbonyl]-2-(isopropoxycarbonyl)benzenesulfonamide To 0.7 g of 2-amino-4,6-dimethoxy-1,3,5-triazine suspended in 5.0 ml anhydrous methylene chloride was added 1.6 g of 2-isopropoxycarbonylbenzenesulfonyl isocyanate in 5.0 ml anhydrous methylene chloride. The resulting mixture was filtered to remove some unreacted 2-amino-4,6-dimethoxytriazine, the methylene chloride filtrate was evaporated at reduced pressure and the residue triturated with chlorobutane to yield 0.5 g of desired product melting at 192°-195° C. The solid showed infrared absorption peaks at 1705 and 1715 $cm^{-1}$ consistent for N-[(4,6-dimethoxy-1,3,5-triazin-2-yl)aminocarbonyl]-2-(isopropoxycarbonyl)benzenesulfonamide.

EXAMPLE 11

N-[(4-methoxy-6-methyl-1,3,5-triazin-2-yl)aminocarbonyl]-2-(isopropoxycarbonyl)benzenesulfonamide To 26.8 g of 2-amino-4-methoxy-6-methyl-1,3,5-triazine in 300 ml anhydrous methylene chloride was added 67.0 g of 2-isopropoxycarbonylbenzenesulfonyl isocyanate in 100 ml anhydrous methylene chloride. The resultant suspension was stirred at ambient temperature for 72 hours, and filtered to yield 40.0 g of the desired product as a white solid, m.p. 193°-196° C. The solid showed infrared absorption peaks at 1700 and 1710 cm$^{31\ 1}$ consistent for N-[(4-methoxy-6-methyl-1,3,5-triazin-2-yl)aminocarbonyl]-2-(isopropoxycarbonyl)benzenesulfonamide.

EXAMPLE 12

N-[(4,6-Dimethoxy-1,3,5-triazin-2-yl)aminocarbonyl]-2-methoxycarbonylbenzenesulfonamide A mixture of 1.6 g of 2-amino-4,6-dimethoxy-1,3,5-triazine, 25 ml of anhydrous methylene chloride and 2.4 g of 2-methoxycarbonylbenzenesulfonylisocyanate was stirred at ambient temperature for 16 hours. It was then filtered to remove unreacted amine and the filtrate evaporated at temperatures up to 40° under reduced pressure. The residue was triturated with butyl chloride and filtered to yield the desired compound which melted above 170° with decomposition.

EXAMPLE 13

N-[(4-Methoxy-6-methyl-1,3,5-triazin-2-yl)aminocarbonyl]-2-methoxycarbonylbenzenesulfonamide To an anhydrous suspension of 1.4 g of 2-amino-4-methoxy-6-methyl-1,3,5-triazine in 25 ml of methylene chloride was added with stirring at ambient temperature and pressure 2.4 g of 2-methoxycarbonylbenzenesulfonylisocyanate. The mixture was thereafter stirred for 16 hours and filtered. The filtrate was evaporated to dryness, the residue was triturated with butyl chloride and the product removed by filtration. The product thus obtained melted at 165°, and had absorption peaks in the infrared at 1550, 1600, 1680 and 1700 cm$^{-1}$ and in the NMR spectrum at 2.5, 3.65, 4.0 with an aromatic multiplet at 7.2-8 ppm.

By using the procedures of Examples 8 to 13 with equivalent amounts of appropriate 2-amino-1,3,5-triazines and appropriately substituted sulfonylisocyanates or isothiocyanates, the compounds of Table II can be prepared:

EXAMPLE 14

N-[(4-methoxy-6-methyl-1,3,5-triazin-2-yl)aminocarbonyl]-2-(1-methylpentyloxycarbonyl)benzenesulfonamide 2-Hexanol (0.61 g) in 2 ml dry toluene was slowly added at room temperature to a solution of 1.5 ml (2 M) trimethylaluminum diluted with 5.0 ml dry toluene under nitrogen. The mixture was stirred at room temperature for 15 minutes and 0.95 g of N-[(4-methoxy-6-methyl-1,3,5-triazin-2-yl)aminocarbonyl]-2-methoxycarbonylbenzenesulfonamide was added. The mixture was warmed under $N_2$ to reflux temperature for 2.5 hr. cooled to room temperature and carefully quenched with 20 ml 10% HCl. The organic phase was taken up in methylene chloride, separated, washed with water, dried over magnesium sulfate, filtered and the solvent evaporated under reduced pressure to give 0.65 g of the desired compound which melted at 125°-130° C. The infrared spectrum exhibited characteristic absorption for the product at 3300, 1725, 1730, 1585, 1555 cm$^{-1}$.

Alternatively, compounds of Tables I and II wherein the desired ester group R is a higher alkane ($C_5$-$C_{12}$) are also prepared by the procedure of Example 14 with an equivalent amount of the appropriate dialkylaluminum alcoholate and an appropriately substituted lower alkyl ester of this invention.

EXAMPLE 15

N-[(4,6-dimethoxy-1,3,5-traizin-2-yl)aminothioxomethyl]-2-methoxycarbonylbenzenesulfonamide A mixture of 4.2 g of methyl 2-sulfamoyl benzoate, 4.0 g of 4,6-dimethoxy-2-isothiocyanato-1,3,5-triazine and 2.7 g of anhydrous potassium carbonate in 70 ml of acetone was warmed to 40° with stirring. After 2 hours a thick precipitate formed and stirring was continued for three more hours at ambient temperature. The precipitate was removed by filtration, suspended in 150 ml of water, stirred and the pH adjusted to 2 by the addition of hydrochloric acid.

The desired product was removed by filtration washed with cold water and dried to yield 4.8 g of product melting at 165°-170°. It showed infrared absorption peaks at 1760, 1650 and 1600 cm$^{-1}$ and nuclear magnetic resonance peaks for the methoxy groups at 4.0 and 3.8 (singlets) and 8.0-8.7 (multiplet) consistent for the desired product.

Example 15 demonstrates a method whereby compounds of this invention can be prepared wherein W is S by using equivalent amounts of the appropriate isothiocyanato pyrimidine or triazine and an appropriately substituted benzenesulfonamide.

TABLE II

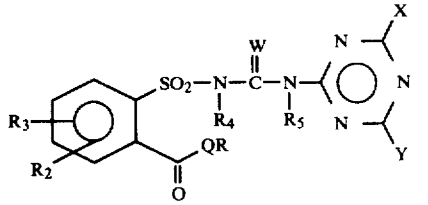

| QR | $R_2$ | $R_3$ | W | $R_4$ | $R_5$ | X | Y | m.p. °C. |
|---|---|---|---|---|---|---|---|---|
| $OCH_3$ | H | H | O | H | H | $CH_3$ | $CH_3$ | 187-189° |
| $OCH_3$ | H | H | O | H | $CH_3$ | $OCH_3$ | $OCH_3$ | |
| $OCH_3$ | H | H | O | H | H | H | H | |
| $OCH_3$ | H | H | S | H | H | $CH_3$ | $OCH_3$ | |

TABLE II-continued

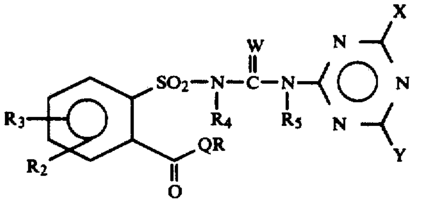

| QR | $R_2$ | $R_3$ | W | $R_4$ | $R_5$ | X | Y | m.p. °C. |
|---|---|---|---|---|---|---|---|---|
| $OCH_3$ | 3-Cl | H | O | H | H | $CH_3$ | $OCH_3$ | |
| $OCH_3$ | 3-$CH_3$ | H | O | H | H | $OCH_3$ | $OCH_3$ | |
| $OC_2H_5$ | 3-Cl | 5-Cl | O | H | H | $OC_2H_5$ | $OCH_3$ | |
| O—i-$C_3H_7$ | 5-$NO_2$ | H | O | H | H | $OC_2H_5$ | $OCH_3CH_2OCH_3$ | |
| $OCH_3$ | H | H | O | H | H | $OCH_3$ | $OCH_2CH_2CH_2OCH_3$ | |
| O—n-$C_3H_7$ | 3-Cl | 6-Cl | O | H | H | $CH_3CH_2O$ | $CH_3O$ | |
| O—n-$C_4H_9$ | H | H | O | H | H | $CH_3O$ | $CF_3$ | |
| $OCH_2CH_2OC_2H_5$ | 3-$OCH_3$ | H | S | H | H | $CH_3$ | $OC_2H_5$ | |
| $OC_2H_5$ | 5-$SCH_3$ | H | O | H | H | $CH_3$ | $O(CH_2)_2OC_2H_5$ | |
| $OCH_3$ | 5-F | H | O | H | H | $OCH_3$ | $O(CH_2)_2COOC_2H_5$ | |
| $OCH_3$ | 5-$CH_3$ | H | O | H | $CH_3$ | $OCH_3$ | $OCH_3$ | |
| $OCH_3$ | 5-F | H | O | H | $CH_3$ | $CH_3$ | $OCH_3$ | |
| $OCH_3$ | 3-Cl | H | O | H | $CH_3$ | $OCH_3$ | $N(CH_3)_2$ | |
| $OCH_3$ | 5-$CH_3$ | H | O | H | H | $CH_3$ | $OCH_3$ | |
| 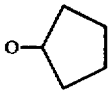 | H | H | O | H | H | $CH_3$ | $OCH_3$ | 160-162° |
| $OCH_2CH(CH_3)_2$ | H | H | O | H | H | $OCH_3$ | $OCH_3$ | 167-170° |
| $O(CH_2)_5CH_3$ | H | H | O | H | H | $OCH_3$ | $OCH_3$ | 133-135° |
| $OCH_3$ | 5-CN | H | O | H | H | $OCH_3$ | $OCH_3$ | |
| $OCH_3$ | 5-$CF_3$ | H | O | H | H | $OCH_3$ | $OCH_3$ | |
| $OCH_3$ | 5-$SO_2CH_3$ | H | O | H | H | $OCH_3$ | $OCH_3$ | |
| $OCH_3$ | 5-$N(CH_3)_2$ | H | O | H | H | $OCH_3$ | $OCH_3$ | |
| $OCH_3$ | 5-$NH_2$ | H | O | H | H | $OCH_3$ | $OCH_3$ | |
| $OCH_3$ | H | H | O | H | H | $OCH_3$ | $SCH_3$ | |
| $OCH_3$ | H | H | O | H | H | $OCH_3$ | $SCH_2COOCH_3$ | |
| $OCH_3$ | H | H | O | H | H | $OCH_3$ | $S(CH_2)_2OC_2H_5$ | |
| O—n-$C_3H_7$ | H | H | O | H | H | $OCH_3$ | $CH_3$ | 157-160° |
| O—n-$C_3H_7$ | H | H | O | H | H | $OCH_3$ | $OCH_3$ | 162-166° |
| O—n-$C_4H_9$ | H | H | O | H | H | $OCH_3$ | $OCH_3$ | 147-150° |
| O—n-$C_4H_9$ | H | H | O | H | H | $OCH_3$ | $CH_3$ | 144-145° |
| O—$C_2H_5$ | H | H | O | H | H | $OCH_3$ | $OCH_3$ | 163-165° |
| O—$C_2H_5$ | H | H | O | H | H | $OCH_3$ | $CH_3$ | 164-167° |
| $OCH_2CH_2OCH_2CH_2Cl$ | H | H | O | H | H | $OCH_3$ | $CH_3$ | 143-144° |
| $OCH_2CH_2Cl$ | H | H | O | H | H | $OCH_3$ | $OCH_3$ | 171-174° |
| $O(CH_2)_9CH_3$ | H | H | O | H | H | $OCH_3$ | $CH_3$ | 129-130° |
| $O(CH_2)_9CH_3$ | H | H | O | H | H | $OCH_3$ | $OCH_3$ | 94-97° |
| 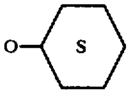 | H | H | O | H | H | $OCH_3$ | $OCH_3$ | 139-143° |
| $OCH_3$ | 4-Cl | H | O | H | H | $OCH_3$ | $OCH_3$ | 142-145° |
| $OCH_2CH{=}CH_2$ | H | H | O | H | H | $OCH_3$ | $OCH_3$ | 155-158° |
| O—i-$C_3H_7$ | H | H | O | H | H | $CH_3$ | $CH_3$ | 187-189° |
| $OCH(CH_2)_7CH_3$<br>\|<br>$CH_3$ | H | H | O | H | H | $OCH_3$ | $CH_3$ | |
| $OCH_2(CH_2)_4CH_2Cl$ | H | H | O | H | H | $CH_3$ | $CH_3$ | |
| $OCH_2CH_2Br$ | H | H | O | H | H | $OCH_3$ | $CH_3$ | |
| $O(CH_2CH_2O)_2C_2H_5$ | H | H | O | H | H | $OCH_3$ | $CH_3$ | |
| $OCH_2CH{=}CH_2$ | H | H | O | H | H | $OCH_3$ | $CH_3$ | 153-155° |
| $O(CH_2)_4CH{=}CH_2$ | H | H | O | H | H | $OCH_3$ | $CH_3$ | |
| $OCH_3$ | 4-Cl | 5-Cl | O | H | H | $OCH_3$ | $OCH_3$ | 172-175° |
| $OCH_3$ | 4-F | H | O | H | H | $OCH_3$ | $OCH_3$ | 192-194° |
| $OCH_3$ | 4-Cl | 5-Cl | O | H | H | $OCH_3$ | $CH_3$ | 159-161° |
| $OCH_3$ | 4-F | H | O | H | H | $OCH_3$ | $CH_3$ | 169-172° |
| $OCH_3$ | 4-Br | H | O | H | H | $OCH_3$ | $CH_3$ | |
| $O(CH_2)_3F$ | H | H | O | H | H | $OCH_3$ | $CH_3$ | |
| $OCH_2CH_2Cl$ | H | H | O | H | H | $CH_3$ | $CH_3$ | |

TABLE II-continued

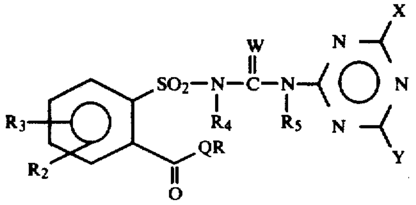

| QR | $R_2$ | $R_3$ | W | $R_4$ | $R_5$ | X | Y | m.p. °C. |
|---|---|---|---|---|---|---|---|---|
| 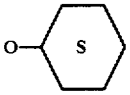 | H | H | O | H | H | $OCH_3$ | $CH_3$ | |
| $OCH_2CCl_3$ | H | H | O | H | H | $CH_3$ | $CH_3$ | |
| $OCH_2CF_3$ | H | H | O | H | H | $OCH_3$ | $CH_3$ | |
| $O-CH_2CHCH_3$<br>$CH_3$ | H | H | O | H | H | $OCH_3$ | $CH_3$ | oil |
| $O(CH_2)_4CH_3$ | H | H | O | H | H | $OCH_3$ | $CH_3$ | |
| $OCHCH_2CH_2CH_3$<br>$CH_3$ | H | H | O | H | H | $OCH_3$ | $CH_3$ | 136–138° |
| $OCH(CH_2CH_3)_2$ | H | H | O | H | H | $CH_3$ | $OCH_3$ | 120–123° |
| $OCH_2CHCH_2CH_3$<br>$CH_3$ | H | H | O | H | H | $OCH_3$ | $CH_3$ | |
| $OCHCHCH_3$<br>$CH_3$ $CH_3$ | H | H | O | H | H | $CH_3$ | $CH_3$ | |
| $OCH_2CBr_3$ | H | H | O | H | H | $CH_3$ | $CH_3$ | |
| $OCHCH_2Cl$<br>$CH_2F$ | H | H | O | H | H | $OCH_3$ | $CH_3$ | |
| 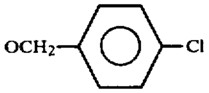 | H | H | O | H | H | $OCH_3$ | $CH_3$ | 192–194° |
| $O-CHCH_2Cl$<br>$CH_3$ | H | H | O | H | H | $OCH_3$ | $CH_3$ | 179–181° |
| $OCH(CH_2)_3CH_3$<br>$CH_3$ | H | H | O | H | H | $OCH_3$ | $CH_3$ | 125–130° |
| $O(CH_2)_4CH_3$ | H | H | O | H | H | $OCH_3$ | $OCH_3$ | 122–125° |
| $OCH_3$ | H | H | O | H | H | $CH_3$ | $N(CH_3)_2$ | 190–191° |
| $OCH_3$ | H | H | O | H | H | $OCH_3$ | $OCH_2CF_3$ | glass |
| $OCH_3$ | H | H | O | H | H | $OCH_3$ | $OCH_2CH_2OCH_3$ | glass |
| $OCH_3$ | H | H | O | H | H | $OCH_3$ | $OCH_2CH_2OCH_2CH_3$ | glass |
| $OCH_3$ | H | H | O | H | H | Cl | Cl | |
| $OCH_3$ | H | H | O | H | H | $CH_3$ | O<br>$OCH_2CNH_2$ | |
| $OCH_3$ | H | H | O | H | H | $CH_3$ | O $C_2H_5$<br>$OCH_2CN$<br>H | |
| $OCH_3$ | H | H | O | H | H | $CH_3$ | O n-$C_4H_9$<br>$OCH_2CN$<br>H | |

TABLE II-continued

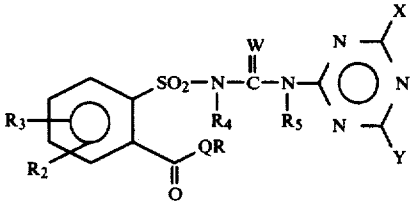

| QR | $R_2$ | $R_3$ | W | $R_4$ | $R_5$ | X | Y | m.p. °C. |
|---|---|---|---|---|---|---|---|---|
| $OCH_3$ | H | H | O | H | H | $CH_3$ | O<br>‖<br>$OCH_2CN(CH_3)_2$ | |
| $OCH_3$ | H | H | O | H | H | $CH_3$ | 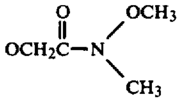 | |
| 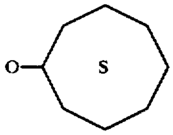 ($C_8$) | H | H | O | H | H | $OCH_3$ | $CH_3$ | 170-172° |
| O—CH—$C(CH_3)_3$<br>\|<br>$CH_3$ | H | H | O | H | H | $OCH_3$ | $CH_3$ | 120-126° |
| O—$CHCH_2CH_2CH{=}CH_2$<br>\|<br>$CH_3$ | H | H | O | H | H | $OCH_3$ | $CH_3$ | 120-124° |
| 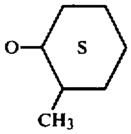 | H | H | O | H | H | $OCH_3$ | $CH_3$ | 132-136° |
| $OCHCH_2CH_3$<br>\|<br>$CH_3$ | H | H | O | H | H | $OCH_3$ | $CH_3$ | 144-146° |
| $OCH_2CH_2OCH_2CH_3$ | H | H | O | H | H | $OCH_3$ | $CH_3$ | 123-127° |
| $OCH_2CH_2OCH_2CH_3$ | H | H | O | H | H | $OCH_3$ | $OCH_3$ | 168-170° |
| $OCH_2CH_2OCH_2CH_3$ | H | H | O | H | H | $CH_3$ | $CH_3$ | |
| $OCH_2CH_2CH(CH_3)_2$ | H | H | O | H | H | $OCH_3$ | $OCH_3$ | 137-139° |
| $OCH_2CH_2CH(CH_3)_2$ | H | H | O | H | H | $OCH_3$ | $CH_3$ | 125-128° |
| 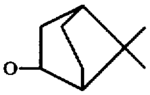 | H | H | O | H | H | $OCH_3$ | $CH_3$ | 125-130° |
| O—$CCH_2CH_2CH_3$<br>\|<br>$CH(CH_3)_2$ | H | H | O | H | H | $OCH_3$ | $CH_3$ | 130-134° |
| $O(CH_2CH_2O)_2C_2H_4Cl$ | H | H | O | H | H | $OCH_3$ | $CH_3$ | $n_D^{25}$-1.5311 |
| 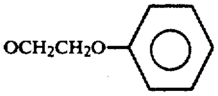 | H | H | O | H | H | $OCH_3$ | $CH_3$ | 80-84° |
| $O(CH_2)_{11}CH_3$ | H | H | O | H | H | $CH_3$ | $CH_3O$ | |
| OCH—$(CH_2)_9CH_3$<br>\|<br>$CH_3$ | H | H | O | H | H | $CH_3$ | $CH_3O$ | |
| $OCH_2C{=}CH(CH_2)_4CH_3$ | H | H | O | H | H | $CH_3$ | $CH_3O$ | |

TABLE II-continued

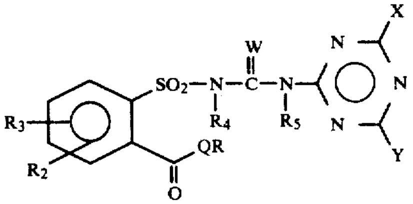

| QR | $R_2$ | $R_3$ | W | $R_4$ | $R_5$ | X | Y | m.p. °C. |
|---|---|---|---|---|---|---|---|---|
| $OCH-CH=CH(CH_2)_5CH_3$<br>$CH_3$ | H | H | O | H | H | $CH_3$ | $CH_3O$ | |
| $OCH+CH_2)_6CH_3$<br>$CH_2CH_2CH_3$ | H | H | O | H | H | $CH_3$ | $CH_3O$ | |
| $OCH_2CH_2-C=CH_2$<br>Cl | H | H | O | H | H | $CH_3$ | $CH_3O$ | |
| $OCH_2C=CHCH(CH_3)_2$<br>Cl | H | H | O | H | H | $CH_3$ | $CH_3O$ | |
| $CH_2Cl$<br>$OCH-C=CH_2$<br>$CH_3$ | H | H | O | H | H | $CH_3$ | $CH_3O$ | |
| $OCHCH=CF_2$<br>$CH_3$ | H | H | O | H | H | $CH_3$ | $CH_3O$ | |
| 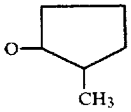 | H | H | O | H | H | $CH_3$ | $CH_3$ | |
| 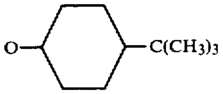 | H | H | O | H | H | $CH_3$ | $OCH_3$ | |
| 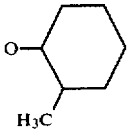 | H | H | O | H | H | $CH_3$ | $OCH_3$ | |
| 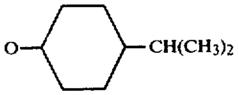 | H | H | O | H | H | $CH_3$ | $OCH_3$ | |
| 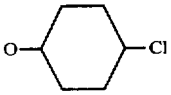 | H | H | O | H | H | $CH_3$ | $OCH_3$ | |
| O—cyclo $C_8H_{15}$ | H | H | O | H | H | $CH_3$ | $CH_3$ | |
| 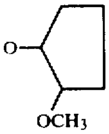 | H | H | O | H | H | $CH_3$ | $CH_3$ | |

TABLE II-continued
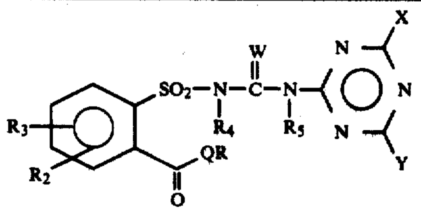
| QR | $R_2$ | $R_3$ | W | $R_4$ | $R_5$ | X | Y | m.p. °C. |
|---|---|---|---|---|---|---|---|---|
| 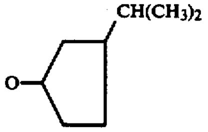 | H | H | O | H | H | $CH_3$ | $CH_3$ | |
| 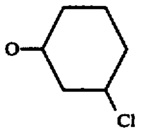 | H | H | O | H | H | $CH_3$ | $CH_3$ | |
| 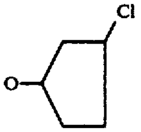 | H | H | O | H | H | $CH_3$ | $CH_3O$ | |
| 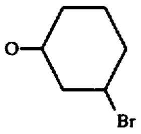 | H | H | O | H | H | $CH_3$ | $CH_3$ | |
| 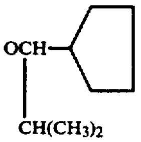 | H | H | O | H | H | $CH_3$ | $CH_3$ | |
| 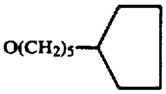 | H | H | O | H | H | $CH_3$ | $CH_3O$ | |
| 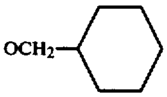 | H | H | O | H | H | $CH_3$ | $OCH_3$ | |
| 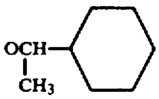 | H | H | O | H | H | $CH_3$ | $CH_3$ | |
| 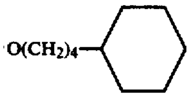 | H | H | O | H | H | $CH_3$ | $CH_3$ | |
| 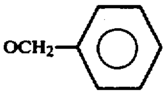 | H | H | O | H | H | $CH_3$ | $OCH_3$ | |

TABLE II-continued

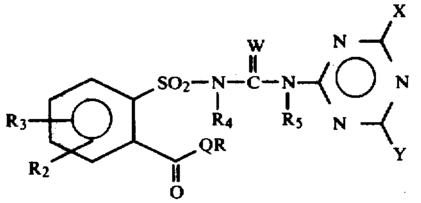

| QR | $R_2$ | $R_3$ | W | $R_4$ | $R_5$ | X | Y | m.p. °C. |
|---|---|---|---|---|---|---|---|---|
| 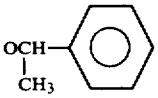 | H | H | O | H | H | $CH_3$ | $OCH_3$ | 155-158° |
| 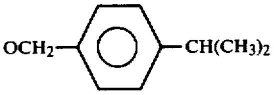 | H | H | O | H | H | $CH_3$ | $OCH_3$ | |
| 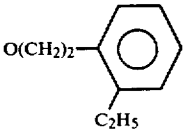 | H | H | O | H | H | $CH_3$ | $OCH_3$ | |
| 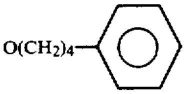 | H | H | O | H | H | $CH_3$ | $OCH_3$ | |
| 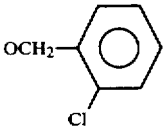 | H | H | O | H | H | $CH_3$ | $OCH_3$ | |
| 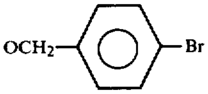 | H | H | O | H | H | $CH_3$ | $OCH_3$ | |
| $O(CH_2CH_2O)_4CH_3$ | H | H | O | H | H | $CH_3$ | $OCH_3$ | |
| $O(CH_2CH_2O)_3C_2H_5$ | H | H | O | H | H | $CH_3$ | $OCH_3$ | |
| $O(CH_2CH_2O)_2C_2H_4Cl$ | H | H | O | H | H | $CH_3$ | $OCH_3$ | |
| $OCH_2CH_2CH_2OCH(CH_3)_2$ | H | H | O | H | H | $CH_3$ | $CH_3$ | |
| $OCH_2CH_2SC_2H_5$ | H | H | O | H | H | $CH_3$ | $CH_3$ | |
| $O(CH_2)_3SC_2H_5$ | H | H | O | H | H | $CH_3$ | $CH_3$ | |
| $OCH_2CH_2SO_2C_2H_5$ | H | H | O | H | H | $CH_3$ | $CH_3$ | |
| $O(CH_2)_3SOCH_3$ | H | H | O | H | H | $CH_3$ | $CH_3$ | |
| $OCH_3$ | H | H | O | H | H | $CH_3$ | $CO_2CH_3$ | |
| $OCH_3$ | H | H | O | H | H | $CH_3$ | $CO_2H$ | |
| $O-i-C_3H_7$ | H | H | O | H | H | $-CH_3$ | $-N(CH_3)_2$ | 151-157° |
| $OCH_3$ | H | H | O | H | H | $-OCH_2CH_2OCH_3$ | $-OCH_2CH_2OCH_3$ | 142-145° |
| $OCH_3$ | H | H | O | H | H | $-OCH_3$ | $-CH_2CH_2OCH_3$ | 100-105° |
| $OCH_3$ | H | H | O | H | H | $-CH_3$ | $-CH_2CH_2OCH_3$ | glass |
| $OCH_3$ | H | H | O | H | H | $-CH_3$ | $-CH_2CH_2CH_2OCH_3$ | 126-128° |
| $OCH_3$ | H | H | O | H | H | $-CH_3$ | $-OCH_2CO_2CH_3$ | 176-178° |
| $OCH_3$ | H | H | O | H | H | $-CH_3$ | $-OCH_2CH_2OCH_3$ | 105-110° |
| $OCH_3$ | H | H | O | H | H | $-CH_3$ | $-OCH_2CF_3$ | 165-168° |
| $OCH_3$ | H | H | O | H | H | $-CH_3$ | $-OCH_2CH_2OCH_2CH_3$ | 125-135° |
| $OCH_3$ | H | H | O | H | H | $-CH_3$ | $-OCH_2CH_3$ | 170-172° |
| $OCH_3$ | H | H | O | H | H | $-CH_3$ | $-OCHCO_2CH_3$<br>\|<br>$CH_3$ | glass |
| $OCH(CH_3)_2$ | H | H | O | H | H | $-CH_3$ | $-OCHCO_2CH_3$<br>\|<br>$CH_3$ | glass |
| $OCH_3$ | H | H | O | H | H | H | $OCH_3$ | |

TABLE II-continued

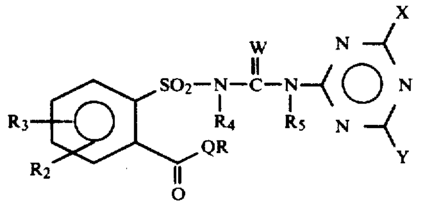

| QR | $R_2$ | $R_3$ | W | $R_4$ | $R_5$ | X | Y | m.p. °C. |
|---|---|---|---|---|---|---|---|---|
| $OCH_3$ | H | H | O | H | H | $-OCH_3$ | n-$C_4H_9$ | |
| $OCH_3$ | H | H | O | H | H | $-OCH_3$ | $-CH_2CH_2CH_2CH_2OCH_3$ | |
| $OCH_3$ | H | H | O | H | H | $-OCH_3$ | $-CH_2CN$ | |
| $OCH_3$ | H | H | O | H | H | $-OCH_3$ | $-CH_2CH_2CN$ | |
| $OCH_3$ | H | H | O | H | H | $-OCH_3$ | $-(CH_2)_3CN$ | |
| $OCH_3$ | H | H | O | H | H | $-OCH_3$ | $-(CH_2)_4CO_2CH_3$ | |
| $OCH_3$ | H | H | O | H | H | $-OCH_3$ | $-CH_2CH_2Cl$ | |
| $OCH_3$ | H | H | O | H | H | $-OCH_3$ | $-(CH_2)_3Br$ | |
| $OCH_3$ | H | H | O | H | H | $-OCH_3$ | $-CH_2CH{=}CHCH_3$ | |
| $OCH_3$ | H | H | O | H | H | $OCH_3$ | $-CH_2C{\equiv}CCH_3$ | |
| $OCH_3$ | H | H | O | H | H | $OCH_3$ | $-NHnC_4H_9$ | |
| $OCH_3$ | H | H | O | H | H | $OCH_3$ | $-N(CH_2)_4CN$<br>\|<br>$CH_3$ | |
| $OCH_3$ | H | H | O | H | H | $OCH_3$ | $-NCH_2CO_2CH_3$<br>\|<br>$CH_3$ | |
| $OCH_3$ | H | H | O | H | H | $OCH_3$ | $-NCH_2CH_2CH_2OCH_2CH_3$<br>\|<br>$CH_3$ | |
| $OCH_3$ | H | H | O | H | H | $OCH_3$ | 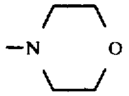 | |
| $OCH_3$ | H | H | O | H | H | $-CH_3$ | $-OCH(CH_3)_2$ | |
| $OCH_3$ | H | H | O | H | H | $-CH_3$ | $-OCH_2CH_2Cl$ | |
| $OCH_3$ | H | H | O | H | H | $-CH_3$ | $-OCH_2CCl_3$ | |
| $OCH_3$ | H | H | O | H | H | $-CH_3$ | $-OCH_2CH_2CN$ | |
| $OCH_3$ | H | H | O | H | H | $-CH_3$ | $-OCH_2CH{=}CH_2$ | |
| $OCH_3$ | H | H | O | H | H | $-CH_3$ | $-OCH_2C{\equiv}CCH_3$ | |
| $OCH_3$ | H | H | O | H | H | $-CH_3$ | $-OCH_2-$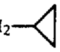 | |
| $OCH_3$ | H | H | O | H | H | $-CH_3$ | $-SCHCO_2CH_3$<br>\|<br>$CH_3$ | |
| $OCH_3$ | H | H | O | H | H | $CH_3$ | $-O(CH_2)_2OCH(CH_3)_2$ | |
| $OCH_3$ | H | H | O | H | H | $CH_3$ | $-SCH_2CH_2SCH_3$ | |
| $OCH_3$ | H | H | O | H | H | $CH_3$ | O<br>‖<br>$-SCH_2CH_2SCH_3$<br>‖<br>O | |
| $OCH_3$ | H | H | O | H | H | $CH_3$ | $-OCH_2CH_2SCH(CH_3)_2$ | |
| $OCH_3$ | H | H | O | H | H | $CH_3$ | $-OCH_2CH_2SCH_3$ | |
| $OCH_3$ | H | H | O | H | H | $CH_3$ | $-SCH_2CH_3$ | |
| $OCH_3$ | H | H | O | H | H | $CH_3$ | $-SCH_2CH_2CN$ | |
| $OCH_3$ | H | H | O | H | H | $CH_3$ | $-SCH_2CH{=}CH_2$ | |
| $-OCH_2-$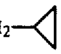 | H | H | O | H | H | $CH_3$ | $CH_3$ | |

TABLE II-continued
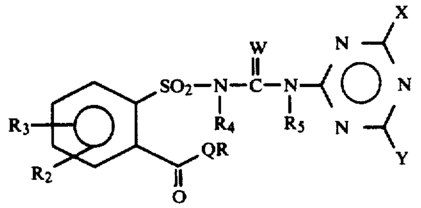
| QR | $R_2$ | $R_3$ | W | $R_4$ | $R_5$ | X | Y | m.p. °C. |
|---|---|---|---|---|---|---|---|---|
| 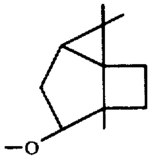 | H | H | O | H | H | $OCH_3$ | $OCH_3$ | |
| 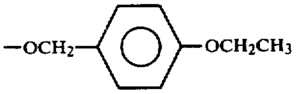 | H | H | O | H | H | $OCH_3$ | $CH_3$ | |
| 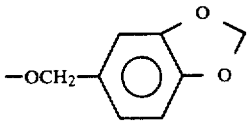 | H | H | O | H | H | $OCH_3$ | $OCH_3$ | |
| 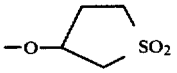 | H | H | O | H | H | $CH_3$ | $CH_3$ | |
| 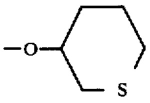 | H | H | O | H | H | $OCH_3$ | $OCH_3$ | |
| 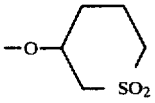 | H | H | O | H | H | $OCH_3$ | $OCH_3$ | |
| 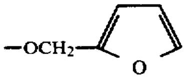 | H | H | O | H | H | $OCH_3$ | $CH_3$ | |
| 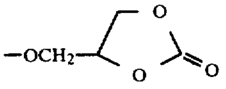 | H | H | O | H | H | $OCH_3$ | $CH_3$ | |
| 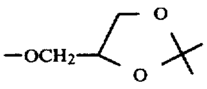 | H | H | O | H | H | $OCH_3$ | $OCH_3$ | |
| 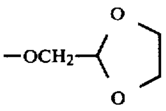 | H | H | O | H | H | $OCH_3$ | $CH_3$ | |
| 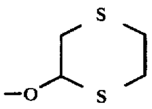 | H | H | O | H | H | $OCH_3$ | $CH_3$ | |

TABLE II-continued

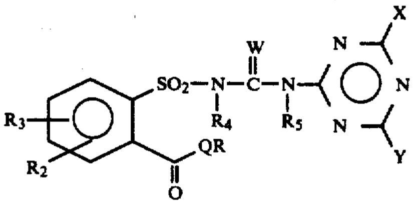

| QR | R2 | R3 | W | R4 | R5 | X | Y | m.p. °C. |
|---|---|---|---|---|---|---|---|---|
| 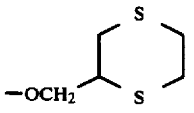 | H | H | O | H | H | $OCH_3$ | $CH_3$ | |
| 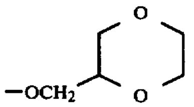 | H | H | O | H | H | $OCH_3$ | $CH_3$ | |
| $-OCHCH_2OCH-CH_3$<br>$CH_3$ $CH_3$ | H | H | O | H | H | $OCH_3$ | $CH_3$ | |
| $-OCHCH_2OCH_2CCl_3$<br>$CH_3$ | H | H | O | H | H | $OCH_3$ | $CH_3$ | |
| 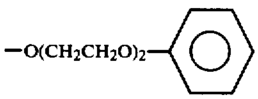 | H | H | O | H | $CH_3$ | $OCH_3$ | $CH_3$ | |
| $-O(CHCH_2O)_2CH_2CH_2Cl$<br>$CH_3$ | H | H | O | H | H | $OCH_3$ | $CH_3$ | |
| $-OCH_2CH_2SCH(CH_3)_2$ | H | H | O | H | H | $OCH_3$ | $CH_3$ | |
| 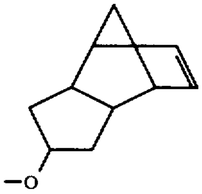 | H | H | O | H | H | $OCH_3$ | $CH_3$ | |
| $-OCH_2CN$ | H | H | O | H | H | $OCH_3$ | $CH_3$ | |
| $CH_3$<br>$-OC(CH_2)_3CH_3$<br>$CN$ | H | H | O | H | H | $OCH_3$ | $OCH_3$ | |
| $-OCH_2-C=C-Cl$<br>$Cl$ $Cl$ | H | H | O | H | H | $OCH_3$ | $CH_3$ | |
| $-O(CH_2)_4-C=CCl_2$<br>$Cl$ | H | H | O | H | H | $OCH_3$ | $CH_3$ | |

EXAMPLE 16

N-[(5,6-dimethyl-1,2,4-triazin-3-yl)aminocarbonyl]-2-methoxycarbonylbenzenesulfonamide To a stirred suspension of 1.2 g of 3-amino-5,6-dimethyl-1,2,4-triazine in 25 ml of anhydrous acetonitrile was added at ambient temperature 2.4 g of 2-methoxycarbonylbenzenesulfonylisocyanate. After stirring for 24 hours at ambient temperature, the resultant precipitate was filtered off to yield 2.5 g of the desired compound melting at 150°-151°. It showed infrared absorption peaks at 1700, 1680 and 1550 $cm^{-1}$, consistent for N-[(5,6-dimethyl-1,2,4-triazin-3-yl)aminocarbonyl]-2-methoxycarbonylbenzenesulfonamide.

By using the procedure of Example 16 with an equivalent amount of a 3-amino-1,2,4-triazine and an appropriately substituted benzenesulfonyl isocyanate or isothiocyanate the compounds of Table III can be prepared.

TABLE III

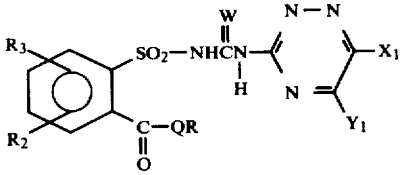

| QR | $R_2$ | $R_3$ | W | $X_1$ | $Y_1$ | m.p. °C. |
|---|---|---|---|---|---|---|
| $OCH_3$ | 5-Cl | H | O | $CH_3$ | $CH_3$ | |
| $OCH_3$ | 5-$NO_2$ | H | O | $CH_3$ | $CH_3$ | |
| $OC_2H_5$ | 5-$CH_3$ | H | O | $CH_3$ | $CH_3$ | |
| o-i-$C_3H_7$ | 5-F | H | O | $CH_3$ | $CH_3$ | |
| o-n-$C_4H_9$ | H | H | O | $CH_3$ | $CH_3$ | |
| O—sec-$C_4H_9$ | H | H | O | $CH_3$ | $CH_3$ | |
| O—tert-$C_4H_9$ | 6-Cl | H | O | $CH_3$ | $CH_3$ | |
| $OCH_2CH_2OC_2H_5$ | H | H | O | H | $CH_3$ | |
| $OCH_3$ | H | H | S | $CH_3$ | $CH_3$ | |
| $OCH_3$ | 3-Cl | 5-Cl | O | $OCH_3$ | $OCH_3$ | |
| $OCH_2CH_2Cl$ | H | H | O | $OCH_3$ | $OCH_3$ | |
| $OCH—CH_3$<br>\|<br>$CH_3$ | H | H | O | $CH_3$ | $CH_3$ | |
| $OCH_2CCl_3$ | H | H | O | $CH_3$ | $CH_3$ | |
| $OCH_2CF_3$ | H | H | O | $CH_3$ | $CH_3$ | |
| $O—CH_2CHCH_3$<br>\|<br>$CH_3$ | H | H | O | $CH_3$ | $CH_3$ | |
| $O(CH_2)_4CH_3$ | H | H | O | $CH_3$ | $CH_3$ | |
| $OCH_3$ | H | H | O | $CH_3$ | $OC_2H_5$ | |
| $OCH(CH_3)_2$ | H | H | O | $CH_3$ | $OC_2H_5$ | |
| $OCH_2CH_2CH(CH_3)_2$ | H | H | O | $CH_3$ | $CH_3$ | 124–127 |
| $OCH_2CHCH_2CH_3$<br>\|<br>$CH_3$ | H | H | O | $CH_3$ | $CH_3$ | |
| $OCHCHCH_3$<br>\| \|<br>$CH_3$ $CH_3$ | H | H | O | $CH_3$ | $CH_3$ | |
| $OCH_2CBr_3$ | H | H | O | $CH_3$ | $CH_3$ | |
| $OCHCH_2Cl$<br>\|<br>$CH_2F$ | H | H | O | $CH_3$ | $CH_3$ | |
| $OCH_3$ | 5-CN | H | O | $CH_3$ | $OCH_3$ | |
| $OCH_3$ | 5-$CF_3$ | H | O | $CH_3$ | $OCH_3$ | |
| $OCH_3$ | 5-$SO_2CH_3$ | H | O | $CH_3$ | $OCH_3$ | |
| $OCH_3$ | 5-$OCH_3$ | H | O | $CH_3$ | $OCH_3$ | |

EXAMPLE 17

N-[(2,6-dimethylpyrimidin-4-yl)aminocarbonyl]2-methoxycarbonylbenzenesulfonamide To a suspension of 1.2 g of 4-amino-2,6-dimethylpyrimidine in 30 ml of dry acetonitrile with stirring was added 2.4 g of 2-methoxycarbonylbenzenesulfonylisocyanate. The mixture was stirred for two hours at ambient temperature, allowed to stand for sixteen hours and the desired product, which had precipitated, was removed by filtration and washed with butyl chloride to yield 2.4 g, m.p. 125°-127°. The product showed absorption peaks by Nuclear Magnetic Resource at 4.0, 2.62 and 2.9 ppm; consistent for the product.

By using the procedure of Example 17 with equivalent amounts of appropriate 4-aminopyrimidines and appropriately substituted sulfonylisocyanates or isothiocyanates, the compounds of Table IV can be prepared.

TABLE IV

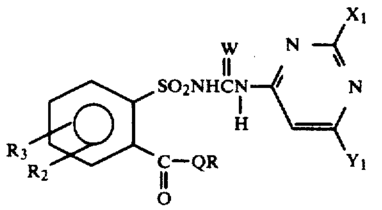

| QR | $R_2$ | $R_3$ | W | $X_1$ | $Y_1$ | m.p. °C. |
|---|---|---|---|---|---|---|
| $OCH_3$ | H | H | O | $OCH_3$ | $CH_3$ | |
| $OCH_3$ | H | H | O | $CH_3$ | $OCH_3$ | |
| $OC_2H_5$ | 6-Cl | H | O | $OCH_3$ | $OCH_3$ | |
| $OCH_3$ | 3-Cl | 5-Cl | O | $OCH_3$ | $C_2H_5$ | |
| $OCH_3$ | 5-$OCH_3$ | H | O | $OCH_3$ | $OCH_3$ | |
| $OCH_3$ | 5-$NO_2$ | 3-Cl | O | $OCH_3$ | $CH_2OCH_3$ | |
| $OC_2H_5$ | 5-Cl | H | O | $OCH_3$ | $OCH_3$ | |
| $OCH_2CH_2Cl$ | H | H | O | $OCH_3$ | $OCH_3$ | |
| $O(CH_2CH_2O)_2CH_3$ | H | H | O | $OCH_3$ | $OCH_3$ | |
| O—$CHCH_3$<br>\|<br>$CH_3$ | H | H | O | $OCH_3$ | $OCH_3$ | |
| $OCH_2CH_2Br$ | H | H | O | Cl | $OCH_3$ | |
| $OCH_2CF_3$ | H | H | O | $OCH_3$ | $OCH_3$ | |
| O—$CH_2CHCH_3$<br>\|<br>$CH_3$ | H | H | O | $OCH_3$ | $CH_3$ | |
| $O(CH_2)_4CH_3$ | H | H | O | $OCH_3$ | $OCH_3$ | |
| $OCH(CH_3)_2$ | H | H | O | $CH_3$ | $OC_2H_5$ | |
| $OCH_3$ | H | H | O | $CH_3$ | $OC_2H_5$ | |
| $OCH_3$ | 5-CN | H | O | $CH_3$ | $OCH_3$ | |
| $OCH_3$ | 5-$CF_3$ | H | O | $CH_3$ | $OCH_3$ | |
| $OCH_3$ | 5-$SO_2CH_3$ | H | O | $CH_3$ | $OCH_3$ | |
| $OCHCH_2CH_3$<br>\|<br>$CH_2CH_3$ | H | H | O | $OCH_3$ | $OCH_3$ | |
| $OCH_2CHCH_2CH_3$<br>\|<br>$CH_3$ | H | H | O | $OCH_3$ | $OCH_3$ | |
| $OCHCHCH_3$<br>/ \\<br>$CH_3$ $CH_3$ | H | H | O | $OCH_3$ | $CH_3$ | |
| $OCH_2CBr_3$ | H | H | O | $OCH_3$ | $OCH_3$ | |
| $OCHCH_2Cl$<br>\|<br>$CH_2F$ | H | H | O | $OCH_3$ | $OCH_3$ | |

By using an appropriate N-[(triazinyl)aminocarbonyl]-2-carbonylbenzenesulfonamide or N[(pyrimidinyl)aminocarbonyl]-2-carbonylbenzenesulfonamide, the compounds of Formula I set forth in Table V can be prepared. For example, the compound of Example 12 can be converted to N-[(4,6-dimethoxy-1,3,5-triazin-2-yl)aminocarbonyl]-2-methoxycarbonyl-N-methylbenzenesulfonamide by the methylation reaction set forth in Equation 2 as follows: An equivalent amount of sodium hydride (50% mineral oil dispersion) can be added to a solution of the compound of Example 12 in dimethylformamide under a nitrogen atmsophere. After hydrogen evolution has ceased, an equivalent amount of dimethylsulfate can be added. The resulting reaction mixture can be stirred for 2–18 hours and the reaction mixture can then be poured into a large volume of water to form a precipitate which can be filtered to yield the above-identified product.

TABLE V-a

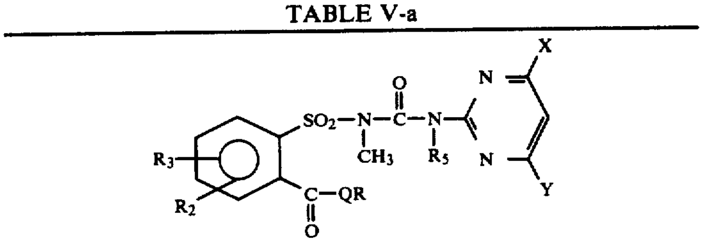

| QR | R2 | R3 | R5 | X | Y | m.p. (°C.) |
|---|---|---|---|---|---|---|
| $OCH_3$ | H | H | H | $CH_3$ | $CH_3$ | |
| $OCH_3$ | H | H | $CH_3$ | $OCH_3$ | $CH_3$ | |
| o-n-$C_3H_7$ | H | H | H | $CH_3$ | $CH_3$ | |
| o-i-$C_3H_7$ | H | H | H | $OCH_3$ | $OCH_3$ | |
| $OCH_3$ | 5-Cl | H | $CH_3$ | $CH_3$ | $OCH_2CH_2OCH_3$ | |
| $OCH_3$ | 3-Cl | 6-Cl | H | $CH_3$ | $OCH_2CH_2$ | |
| $O(CH_2CH_2O)_2CH_3$ | H | H | H | $OCH_3$ | $CH_3$ | |
| $O(CH_2)_4CH{=}CH_2$ | H | H | H | $OCH_3$ | $CH_3$ | |
| $OCH_2CF_3$ | H | H | H | $OCH_3$ | $CH_3$ | |
| $O(CH_2)_4CH_3$ | H | H | H | $CH_3$ | $CH_3$ | |
| $OCH_2CH(CH_3)CH_2CH_3$ | H | H | H | $OCH_3$ | $OCH_3$ | |
| $OCH(CH_3)CH(CH_3)CH_3$ | H | H | H | $OCH_3$ | $CH_3$ | |

TABLE V-b

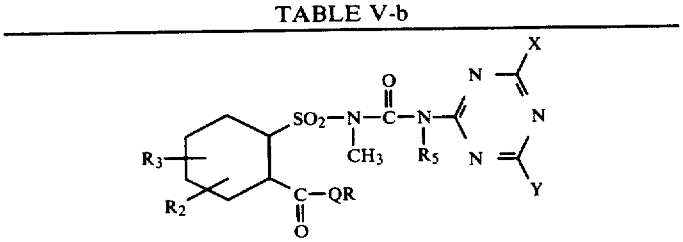

| QR | R2 | R3 | R5 | X | Y |
|---|---|---|---|---|---|
| $OCH_3$ | H | H | H | $CH_3$ | $OCH_3$ |
| $OCH_3$ | H | H | $CH_3$ | $CH_3$ | $OCH_3$ |
| $OC_2H_5$ | 5-$NO_2$ | H | $CH_3$ | H | $OCH_2CH_2CO_2CH_3$ |
| o-n-$C_4H_9$ | 6-Cl | H | H | $CH_3$ | $O-CH(CH_3)CO_2CH_3$ |
| $N(C_2H_5)_2$ | H | H | $CH_3$ | $OCH_3$ | $N(CH_3)_2$ |
| $N(CH_3)-OCH_3$ | H | H | H | $OCH_3$ | $NH(CH_3)$ |
| $O(CH_2)_9CH_3$ | H | H | H | $OCH_3$ | $CH_3$ |
| $O(CH_2CH_2O)_2C_2H_5$ | H | H | H | $OCH_3$ | $CH_3$ |
| $OCH(CH_3)CH_3$ | H | H | H | $OCH_3$ | $CH_3$ |
| $O-CH_2CH(CH_3)CH_3$ | H | H | H | $CH_3$ | $CH_3$ |
| $O(CH_2)_4CH_3$ | H | H | H | $OCH_3$ | $OCH_3$ |
| $OCH(CH_3)CH_2CH_2CH_3$ | H | H | H | $CH_3$ | $CH_3$ |
| $OCH(CH_2CH_3)CH_2CH_3$ | H | H | H | $OCH_3$ | $OCH_3$ |

TABLE V-b-continued

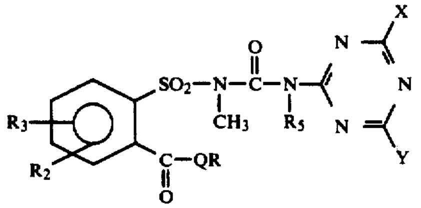

| QR | $R_2$ | $R_3$ | $R_5$ | X | Y |
|---|---|---|---|---|---|
| $OCH_2CHCH_2CH_3$<br>$CH_3$ | H | H | H | $CH_3$ | $CH_3$ |
| $OCHCHCH_3$<br>$CH_3$ $CH_3$ | H | H | H | $CH_3$ | $CH_3$ |
| $OCH_2CBr_3$ | H | H | H | $CH_3$ | $CH_3$ |
| $OCHCH_2Cl$<br>$CH_2F$ | H | H | H | $OCH_3$ | $CH_3$ |

By using an appropriately substituted benzenesulfonyl-N-methylcarbamyl chloride or thiocarbamylchloride and an appropriate aminopyrimidine or amino-traizine, the compounds of Formula I set forth in Table VI can be prepared by the procedure of Equation 5. For example, N-[N-(4-methoxy-6-methylpyrimidin-2-yl)-N-methylaminocarbonyl]-2-methoxycarbonyl-N-methylbenzenesulfonamide can be prepared by adding 3.0 g of N-[(2-methoxycarbonylphenyl)sulfonyl]-N-methylcarbamylchloride in 50 ml of tetrahydrofuran containing 1.0 g of triethyl amine to 1.5 g of 2-methylamino-4-methoxy-6-methylpyrimidine. That mixture can be stirred at reflux for several hours, the precipitated salts can be filtered off and the filtrate can be concentrated to yield the foregoing product.

TABLE VI-a

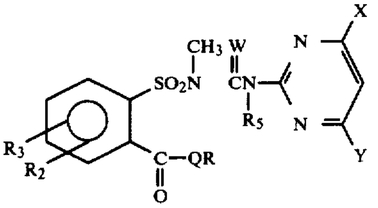

| QR | $R_2$ | $R_3$ | W | $R_5$ | X | Y |
|---|---|---|---|---|---|---|
| $OCH_3$ | H | H | S | $CH_3$ | $OCH_3$ | $OCH_3$ |
| $OCH_3$ | H | H | S | H | $CH_3$ | $CH_3$ |
| $OCH_3$ | 6-$CH_3$ | H | O | $CH_3$ | $OCH_3$ | $OCH_2CH_2CO_2CH_3$ |
| $O(CH_2)_9CH_3$ | H | H | O | H | $OCH_3$ | $OCH_3$ |
| $O(CH_2)_4CH{=}CH_2$ | H | H | O | H | $OCH_3$ | $OCH_3$ |
| $OCH_2CH_2Cl$ | H | H | O | H | $OCH_3$ | $OCH_3$ |
| $O-CH_2CHCH_3$<br>$CH_3$ | H | H | O | H | $CH_3$ | $CH_3$ |
| $O(CH_2)_4CH_3$ | H | H | O | H | $CH_3$ | $CH_3$ |
| $OCHCH_2CH_2CH_3$<br>$CH_3$ | H | H | O | H | $CH_3$ | $CH_3$ |
| $OCHCH_2CH_3$<br>$CH_2CH_3$ | H | H | O | H | $CH_3$ | $CH_3$ |
| $OCH_2CHCH_2CH_3$<br>$CH_3$ | H | H | O | H | $CH_3$ | $CH_3$ |
| $OCHCHCH_3$<br>$CH_3$ $CH_3$ | H | H | O | H | $CH_3$ | $CH_3$ |
| $OCH_2CBr_3$ | H | H | O | H | $CH_3$ | $CH_3$ |

TABLE VI-a-continued

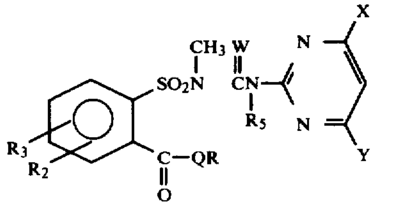

| QR | $R_2$ | $R_3$ | W | $R_5$ | X | Y |
|---|---|---|---|---|---|---|
| $OCHCH_2Cl$ (CH₂F branch: $CH_2F$) | H | H | O | H | $CH_3$ | $CH_3$ |
| $OCH_2CH_2F$ | H | H | O | H | $OCH_3$ | $OCH_3$ |
| $OCH_2CCl_3$ | H | H | O | H | $OCH_3$ | $OCH_3$ |

TABLE VI-b

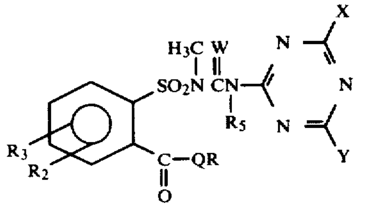

| QR | $R_2$ | $R_3$ | W | $R_5$ | X | Y |
|---|---|---|---|---|---|---|
| $OCH_3$ | H | H | S | $CH_3$ | $OCH_3$ | $OCH_3$ |
| $O-i-C_3H_7$ | 5-F | H | S | $CH_3$ | $OCH_3$ | $OC_2H_5$ |
| $O(CH_2)_9CH_3$ | H | H | O | H | $OCH_3$ | $OCH_3$ |
| $O(CH_2CH_2O)_2CH_3$ | H | H | O | H | $OCH_3$ | $OCH_3$ |
| $O(CH_2)_4CH=CH_2$ | H | H | O | H | $OCH_3$ | $OCH_3$ |
| $O-CH_2CHCH_3$ / $CH_3$ | H | H | O | H | $OCH_3$ | $OCH_3$ |
| $O(CH_2)_4CH_3$ | H | H | O | H | $OCH_3$ | $OCH_3$ |
| $OCHCH_2CH_3$ / $CH_2CH_3$ | H | H | O | H | $CH_3$ | $CH_3$ |
| $OCH_2CHCH_2CH_3$ / $CH_3$ | H | H | O | H | $OCH_3$ | $OCH_3$ |
| $OCHCHCH_3$ / $CH_3$ $CH_3$ | H | H | O | H | $OCH_3$ | $OCH_3$ |
| $OCH_2CBr_3$ | H | H | O | H | $OCH_3$ | $OCH_3$ |
| $OCHCH_2Cl$ / $CH_2F$ | H | H | O | H | $OCH_3$ | $OCH_3$ |
| $OCH_2CF_3$ | H | H | O | H | $OCH_3$ | $OCH_3$ |

EXAMPLE 18

N-[(4,6-dimethylpyrimidin-2-yl)aminocarbonyl]-2-carboxybenzenesulfonamide

A mixture of 2.0 g of N-[(4,6-dimethylpyrimidin-2-yl)aminocarbonyl]-2-methoxycarbonylbenzenesulfonamide and 11 ml. of 50% aqueous sodium hydroxide was warmed on a steam bath with shaking; 40 ml. of water was added and heating and shaking continued during the next half hour. The resulting solution was then filtered and the filtrate acidified with hydrochloric acid to pH 2 to yield a precipitate which was isolated by filtration to yield the title compound, 0.7 g melting at 160° with decomposition. The nuclear magnetic resonance spectrum showed resonance peaks for the methyl substituents on the pyrimidine ring at 2.66 ppm and the ring hydrogens at 7.2 to 8.4 ppm. The disappearance of the resonance peak at 4.0 ppm confirmed the conversion of the methyl ester to the carboxy group.

EXAMPLE 18-A

N-[(4-Methoxy-6-methylpyrimidin-2-yl)aminocarbonyl]-2-carboxybenzenesulfonamide 4.0 g of N-[(4-methoxy-6-methylpyrimidin-2-yl)aminocarbonyl]-2-methoxycarbonylbenzenesulfonamide was dissolved in a mixture of 20 ml of absolute ethanol, 2.5 ml of water and 2.5 g of potassium hydroxide. After stirring at 25° for 24 hours the mixture had become a semi-solid mass. Enough cold water was added to dissolve the solid and the solution was acidified to pH 3 with concentrated hydrochloric acid. The resultant precipitate was isolated by filtration and washed with cold water. The precipitate was dried to afford 3.7 g of the title compound, melting at 195°-200°. The nuclear magnetic resonance spectrum exhibited resonances for the methyl and methoxy substituents on the pyrimidine ring at 2.67 ppm and 4.20 ppm respectively.

Peaks for the pyrimidine ring proton and phenyl ring protons were observed at 6.73 ppm and 7.9 to 8.6 ppm respectively. The disappearance of the resonance peak at 4.10 confirmed the conversion of the methyl ester to the carboxy group.

By using an appropriate N-[(triazinyl)aminocarbonyl]-2-alkoxycarbonylbenzenesulfonamide or a N-[(pyrimidinyl)aminocarbonyl]-2-alkoxycarbonylbenzenesulfonamide or their aminothioxomethyl analogs (W=S), the compounds of Formula I set forth in Table VII-a-VII-d can be prepared by the procedure of Example 18 or 18-A.

TABLE VII-a

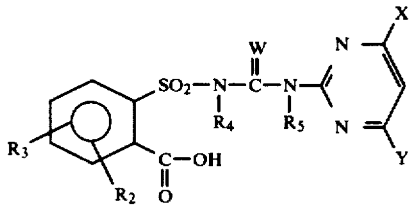

| R2 | R3 | R4 | R5 | W | X | Y |
|---|---|---|---|---|---|---|
| H | H | H | H | O | $CH_3$ | $OCH_3$ |
| 6-Cl | H | $CH_3$ | H | O | $OCH_3$ | $CH_2OCH_3$ |
| 6-Cl | H | H | H | S | $OCH_3$ | $CH_3$ |
| 3-Cl | 5-Cl | H | H | S | $OCH_3$ | $N(CH_3)_2$ |

TABLE VII-b

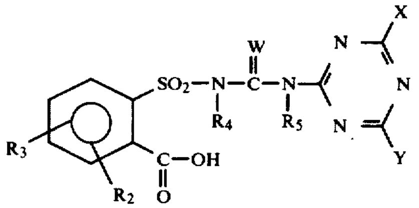

| R2 | R3 | R4 | R5 | W | X | Y |
|---|---|---|---|---|---|---|
| H | H | H | H | O | $CH_3$ | $OCH_3$ |
| H | H | H | H | S | $OCH_3$ | $OCH_3$ |
| 4-Cl | 6-Cl | H | H | O | $OCH_3$ | $OCH_2CH_3$ |

TABLE VII-c

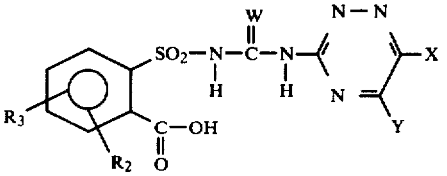

| R2 | R3 | W | X | Y |
|---|---|---|---|---|
| H | H | O | $CH_3$ | $CH_3$ |
| H | H | S | $CH_3$ | $CH_3$ |

TABLE VII-d

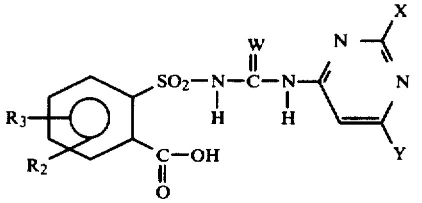

| R2 | R3 | W | X | Y |
|---|---|---|---|---|
| H | H | O | $OCH_3$ | $OCH_3$ |
| H | H | S | $OCH_3$ | $OCH_3$ |
| 3-Cl | H | O | $OCH_3$ | $CH_3$ |

EXAMPLE 18-B

Methyl 2-[[[4-(1-carboxyethoxy)-6-methyl-1,3,5-triazin-2-yl]aminocarbonyl]aminosulfonyl]benzoate Methyl 2-(isocyanatosulfonyl)benzoate (10.1 g) and 8.0 g of ethyl 2-[(4-amino-6-methyl-1,3,5-triazin-2-yl)oxy]propanoate were stirred in 80 ml of methylene chloride at ambient temperature for 18 hours. An additional 2 g of the sulfonylisocyanate was added and the reaction mixture was stirred for four more hours and then 2 g more of the sulfonylisocyanate was added. After stirring for four more hours at ambient temperature, 400 ml of water was added and the pH of this mixture was adjusted to pH 8 by the addition of 10% aqueous sodium hydroxide. The aqueous phase was separated and acidified to pH 1 with hydrochloric acid to precipitate a thick white gum. Sufficient 50% aqueous sodium hydroxide was added to achieve pH 12 and the mixture was heated on a steam bath until a clear solution resulted. The solution was again acidified with hydrochloric acid to pH 3 and the resultant cloudy solution was extracted with dichloromethane. The organic phase was dried and the solvent was removed to afford 3.7 g of the title compound as a glass.

By using an appropriate N-[(triazinyl)aminocarbonyl]-2-carbonylbenzenesulfonamide or a N-[(pyridinyl)aminocarbonyl]-2-carbonylbenzenesulfonamide or their aminothioxomethyl analogs, the compounds of Formula I wherein L=OH as shown in Table VII-e and VII-f can be prepared by the procedure of Example 18-B.

TABLE VII-e

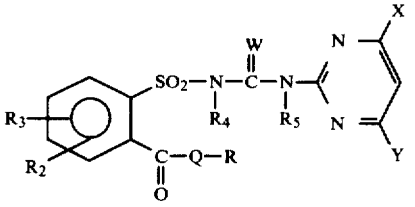

| QR | R2 | R3 | R4 | R5 | W | X | Y |
|---|---|---|---|---|---|---|---|
| $OCH_3$ | H | H | H | H | O | $OCH_3$ | $-\overset{O}{\overset{\|}{C}}-OH$ |
| $OCH_3$ | H | H | H | H | O | $OCH_3$ | $CH_2\overset{O}{\overset{\|}{C}}OH$ |
| $OCH_3$ | H | H | H | H | O | $OCH_3$ | $CH_2CH_2\overset{O}{\overset{\|}{C}}OH$ |
| $OCH_3$ | H | H | H | H | O | $OCH_3$ | $(CH_2)_4\overset{O}{\overset{\|}{C}}OH$ |
| $OCH_3$ | H | H | H | H | O | $CH_3$ | $OCH_2\overset{O}{\overset{\|}{C}}OH$ |
| $OCH_3$ | H | H | H | H | O | $CH_3$ | $O\underset{CH_3}{\underset{\|}{CH}}\overset{O}{\overset{\|}{C}}OH$ |
| $OCH_3$ | H | H | H | H | O | $CH_3$ | $O(CH_2)_3\overset{O}{\overset{\|}{C}}OH$ |
| $OCH_3$ | H | H | H | H | O | $CH_3$ | $S\underset{CH_3}{\underset{\|}{CH}}\overset{O}{\overset{\|}{C}}OH$ |
| $OCH_3$ | H | H | H | H | O | $CH_3$ | $\overset{H}{\overset{\|}{N}}-CH_2\overset{O}{\overset{\|}{C}}OH$ |

TABLE VII-e-continued

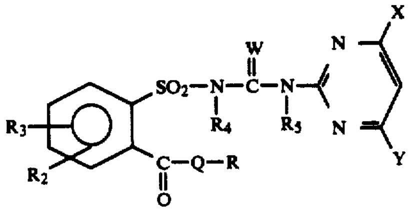

| QR | $R_2$ | $R_3$ | $R_4$ | $R_5$ | W | X | Y |
|---|---|---|---|---|---|---|---|
| $OCH_3$ | H | H | H | H | O | $CH_3$ | 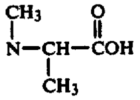 |

TABLE VII-f

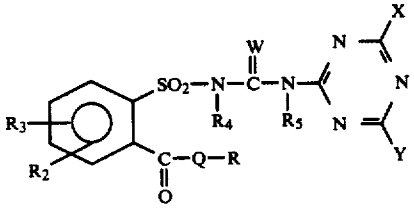

| QR | $R_2$ | $R_3$ | $R_4$ | $R_5$ | W | X | Y |
|---|---|---|---|---|---|---|---|
| $OCH_3$ | H | H | H | H | O | $OCH_3$ | 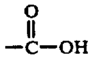 |
| $OCH_3$ | H | H | H | H | O | $OCH_3$ | 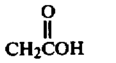 |
| $OCH_3$ | H | H | H | H | O | $OCH_3$ | 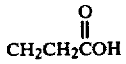 |
| $OCH_3$ | H | H | H | H | O | $OCH_3$ | 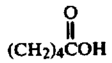 |
| $OCH_3$ | H | H | H | H | O | $CH_3$ | 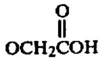 |
| $OCH_3$ | H | H | H | H | O | $CH_3$ | 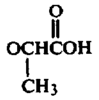 |
| $OCH_3$ | H | H | H | H | O | $CH_3$ | 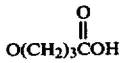 |
| $OCH_3$ | H | H | H | H | O | $CH_3$ | 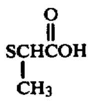 |
| $OCH_3$ | H | H | H | H | O | $CH_3$ | 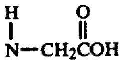 |
| $OCH_3$ | H | H | H | H | O | $CH_3$ | 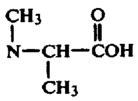 |

EXAMPLE 19

N-[(4,6-dimethylpyrimidin-2-yl)aminocarbonyl]-2-dimethylaminocarbonylbenzenesulfonamide To 4.1 g of N[(4,6-dimethylpyrimidin-2-yl)]-2-methoxycarbonylbenzenesulfonamide in 75 ml of toluene was added 37 ml of a methylene chloride and toluene solution (3:5) containing 1.25 g of dimethylaluminum dimethylamide with stirring at ambient temperature. The mixture was heated to reflux (82° C.) for two hours, cooled, 10 ml of methanol added and the solvents evaporated in vacuo. The residue was treated with a mixture of methanol, water and dilute hydrochloric acid and the precipitated product filtered off to yield 1.25 g of the desired product. Extraction of the aqueous filtrate with methylene chloride gave 1.12 g more product, m.p. 166°-8° C. The product showed NMR absorption peaks at 2.5 ppm, pyrimidinmethyl; 2.85 and 3.1 ppm, nonequivalent methyl groups of the dimethylamide; 6.8 ppm, pyrimidin H; and 7.2-8.4 ppm, aromatic hydrogens.

EXAMPLE 20

N-[(4,6-dimethoxypyrimidin-2-yl)aminocarbonyl]-2-isopropylaminocarbonylbenzenesulfonamide To 4.5 g of N-[(4,6-dimethoxypyrimidin-2-yl)aminocarbonyl]-2-methoxycarbonylbenzenesulfonamide in 75 ml methylene chloride was added with stirring at ambient temperature, 37 ml of a methylene chloride solution containing 1.44 g of dimethyaluminum isopropylamide. The mixture was heated to reflux and the methylene chloride removed by distillation while adding dry toluene until a temperature of 100° C. was reached. Refluxing was continued for two hours at 100° C. after which the mixture was cooled and 10 ml of methanol was added and the solvents evaporated in vacuo. The residue was then triturated with a mixture of methanol, water and dilute HCl and the product extracted from this aqueous slurry with methylene chloride. Evaporation of the methylene chloride extract yielded the product as a solid (4.28 g). Trituration of the product with 1-chlorobutane gave 2.0 g of pure product m.p. 148°-150° C. which showed a single spot on TLC (Silica gel, Acetone/Hexane 1:1, $R_f$=0.34) and gave absorption peaks in the NMR spectrum at 1.15, 4.0, 3.8-4.3 and 7.5-8.2 ppm.

Elem. Anal. Calcd. for $C_{17}H_{21}N_5O_6S$; Calc.: C, 48.2; H, 4.96; N, 16.5. Found: C, 48.1; H, 5.20; N, 16.0.

By using the procedure of Examples 19 and 20 with equivalent amounts of appropriately substituted dialkylaluminum-N-alkylamide and appropriately substituted esters of this invention, the compounds of Table VIII can be prepared.

TABLE VIII-a

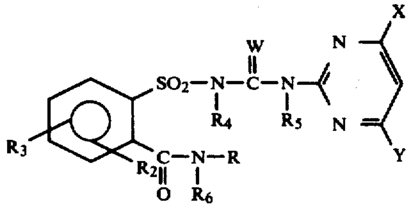

| R | $R_2$ | $R_3$ | $R_4$ | $R_5$ | $R_6$ | W | X | Y | m.p. (°C.) |
|---|---|---|---|---|---|---|---|---|---|
| $CH_3$ | H | H | H | H | H | O | $OCH_3$ | $CH_3$ | 184–185° |
| $CH_3$ | H | H | H | H | H | O | $OCH_3$ | $OCH_3$ | 168–170° |
| n-$C_3H_7$ | H | H | H | H | H | O | $OCH_3$ | $OCH_3$ | |
| i-$C_3H_7$ | 5-Cl | H | H | H | H | O | $CH_3$ | $CH_2OCH_3$ | |
| $CH_2-C_6H_5$ | H | H | H | H | H | O | $OCH_3$ | $CH_3$ | 95–102° |
| H | H | H | H | H | H | O | $CH_3$ | SCN | |
| $CH_3$ | H | H | H | H | $CH_3$ | O | $CH_3$ | $CH_3$ | 166–168° |
| i-$C_3H_7$ | H | H | H | H | H | O | $OCH_3$ | $OCH_3$ | 148–150° |
| n-$C_3H_7$ | H | H | H | H | $C_2H_5$ | O | $CH_3$ | 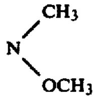 | |
| $(CH_2)_7CH_3$ | H | H | H | H | H | O | $CH_3$ | $CH_3O$ | |
| $(CH_2)_{11}CH_3$ | H | H | H | H | H | O | $CH_3$ | $CH_3O$ | 65–70° |
| i-$C_3H_7$ | H | H | H | H | H | O | $OCH_3$ | $CH_3$ | 157–158° |
| $CH_2C_6H_5$ | H | H | H | H | $CH_3$ | S | $OCH_3$ | $CH_3$ | |
| $CH_2C_6H_5$ | H | H | H | H | $C_2H_5$ | O | $CH_3$ | $CH_3$ | |
| H | H | H | H | H | H | O | $OCH_3$ | $CH_3$ | 148–150° |
| $-CH_2CH=CH_2$ | H | H | H | H | H | S | $OCH_3$ | $CH_3$ | |
| 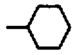 | H | H | H | H | $CH_3$ | O | $OCH_3$ | $CH_3$ | 127–130° |
| $CH_3$ | H | H | H | H | $CH_3$ | O | $CH_3$ | $OCH_3$ | 162–165° |
| $C_2H_5$ | H | H | H | H | $C_2H_5$ | S | $CH_3$ | $OCH_3$ | |
| $C_2H_5$ | H | H | H | H | $CH_3$ | O | $CH_3$ | $CH_3$ | |
| $C_2H_5$ | H | H | H | H | $CH(CH_3)_2$ | O | $CH_3$ | $CH_3$ | |
| n-$C_4H_9$ | H | H | H | H | H | S | $CH_3$ | $OCH_3$ | |
| 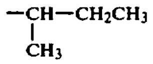 | H | H | H | H | H | O | $CH_3$ | $OCH_3$ | |
| i-$C_3H_7$ | H | H | H | H | H | O | $CH_3$ | $CH_3$ | 179° |
| 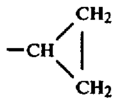 | H | H | H | H | H | O | $CH_3$ | $OCH_3$ | 122–124° |
| 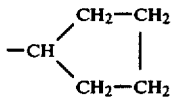 | H | H | H | H | H | O | $CH_3$ | $CH_3$ | |
| $-(CH_2)_3OCH_3$ | H | H | H | H | H | O | $OCH_3$ | $OCH_3$ | |
| $(CH_2)_2OC_2H_5$ | H | H | H | H | H | S | $OCH_3$ | $CH_3$ | |
| $-CH_2-CH_2-CH=CH_2$ | H | H | H | H | H | O | $CH_3$ | $OCH_3$ | |
| 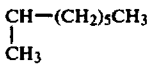 | H | H | H | H | H | O | $CH_3$ | $OCH_3$ | |
| 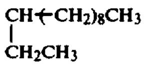 | H | H | H | H | H | S | $CH_3$ | $OCH_3$ | |
| $(CH_2)_4C_6H_5$ | H | H | H | H | H | O | $CH_3$ | $OCH_3$ | |
| 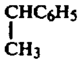 | H | H | H | H | H | O | $CH_3$ | $OCH_3$ | |
| 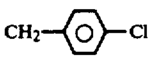 | H | H | H | H | H | S | $CH_3$ | $OCH_3$ | |

TABLE VIII-a-continued

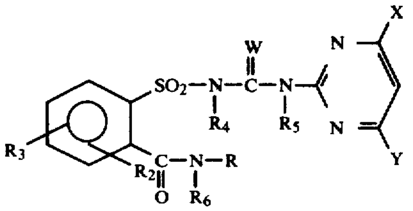

| R | $R_2$ | $R_3$ | $R_4$ | $R_5$ | $R_6$ | W | X | Y | m.p. (°C.) |
|---|---|---|---|---|---|---|---|---|---|
| $CH_2$—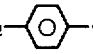—$CH(CH_3)_2$ | H | H | H | H | H | O | $CH_3$ | $OCH_3$ | |
| $-(CH_2)_4-$* | H | H | H | H | * | O | $CH_3$ | $OCH_3$ | 175-177° |
| $-(CH_2)_4-$* | H | H | H | H | * | O | $OCH_3$ | $OCH_3$ | 189-191° |
| $-(CH_2)_4-$* | H | H | H | H | * | O | $CH_3$ | $CH_3$ | 180-181° |
| $-(CH_2)_5-$* | H | H | H | H | * | O | $CH_3$ | $CH_3$ | 178-181° |
| $-(CH_2)_5-$* | H | H | H | H | * | O | $OCH_3$ | $CH_3$ | 180-183° |
| $-(CH_2)_2O(CH_2)_2-$* | H | H | H | H | * | O | $OCH_3$ | $CH_3$ | 162-164° |
| $-(CH_2)_2N(CH_2)_2-$*<br>$CH_3$ | H | H | H | H | * | O | $OCH_3$ | $CH_3$ | |
| $CH_2C_6H_5$ | H | H | H | H | H | O | $OCH_3$ | $OCH_3$ | 112-117° |
| $CH_2C_6H_5$ | H | H | H | H | H | O | $CH_3$ | $CH_3$ | 75-85° |
| $CH_3O$ | H | H | H | H | $CH_3$ | O | $CH_3$ | $CH_3$ | 183-184° |
| t-$C_4H_9$ | H | H | H | H | H | O | $OCH_3$ | $CH_3$ | 122-125° |
| $(CH_2)_5$* | H | H | H | H | * | O | $OCH_3$ | $OCH_3$ | 193-195° |
| $(CH_2)_5$* | H | H | H | H | * | O | Cl | Cl | 156-157° |
| n-$C_3H_7$ | H | H | H | H | H | O | $OCH_3$ | $OCH_3$ | 184-185° |
| $CH_3$ | H | H | H | H | $CH_3$ | O | $OCH_3$ | $OCH_3$ | 184-186° |
| $C(CH_3)_3$ | H | H | H | H | H | O | $CH_3$ | $OCH_3$ | 122-125° |
| 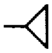 | H | H | H | H | H | O | $OCH_3$ | $OCH_3$ | 194-195° |
| 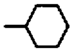 | H | H | H | H | H | O | $OCH_3$ | $OCH_3$ | 199-200° |
| $-CH_2CH\equiv CH_2$ | H | H | H | H | H | O | $OCH_3$ | $OCH_3$ | 147-150° |
| $CH_3$<br>$-CH_2C=CH_2$ | H | H | H | H | H | O | $OCH_3$ | $OCH_3$ | 164-166° |
| 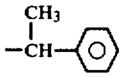 | H | H | H | H | H | O | $OCH_3$ | $OCH_3$ | 122-127° |
| $C_2H_5$ | H | H | H | H | $C_2H_5$ | O | $OCH_3$ | $OCH_3$ | 188-190° |
| $-CH_2-C\equiv H$ | H | H | H | H | H | O | $CH_3$ | $OCH_3$ | |
| $-C(CH_3)_2C\equiv CH$ | H | H | H | H | H | O | $CH_3$ | $CH_3$ | |
| $-CH_2-C\equiv C-CH_3$ | H | H | H | H | H | O | $CH_3$ | $OCH_3$ | |
| $-CH-C\equiv C-C_2H_5$<br>$CH_3$ | H | H | H | H | H | O | $CH_3$ | $CH_3$ | |

*R and $R_6$ are taken together.

TABLE VIII-b

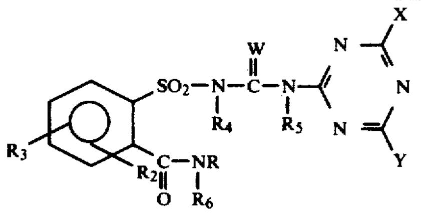

| R | $R_2$ | $R_3$ | $R_4$ | $R_5$ | $R_6$ | W | X | Y | m.p. °C. |
|---|---|---|---|---|---|---|---|---|---|
| $CH_3$ | H | H | H | H | H | O | $OCH_3$ | $OCH_3$ | 166-168° |
| $CH_3$ | H | H | H | H | H | O | $CH_3$ | $OCH_3$ | 172° |
| $C_2H_5$ | 5-Cl | H | $CH_3$ | H | H | O | $CH_3$ | $CH_2OCH_3$ | |
| $CH_3$ | 4-Cl | 6-Cl | $CH_3$ | $CH_3$ | H | O | $OCH_3$ | $OC_2H_5$ | |
| $CH_3$ | H | H | H | H | H | S | $CH_3$ | $OCH_3$ | |
| $(CH_2)_4CH_3$ | H | H | H | H | H | S | $OCH_3$ | $CH_3$ | |
| $(CH_2)_{11}CH_3$ | H | H | H | H | H | O | $OCH_3$ | $CH_3$ | 107-109° |
| $CH(CH_3)-C_6H_5$ | H | H | H | H | H | O | $CH_3$ | $CH_3O$ | |
| 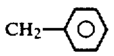 | H | H | H | H | H | O | $CH_3O$ | $CH_3O$ | 212-217° |
| 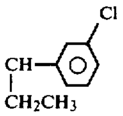 | H | H | H | H | H | O | $CH_3$ | $CH_3O$ | |
| i-$C_3H_7$ | H | H | H | H | H | O | $OCH_3$ | $OCH_3$ | 102° |
| sec-$C_4H_9$ | H | H | H | H | H | O | $OCH_3$ | $CH_3$ | |
| $C_2H_5$ | H | H | H | H | $CH_3$ | S | $OCH_3$ | $CH_3$ | |
| sec-$C_4H_9$ | H | H | H | H | i-$C_3H_7$ | S | $OCH_3$ | $CH_3$ | |
| $-CH-CH_2$ / $CH_2-CH_2$ (ring) | H | H | H | H | H | O | $OCH_3$ | $CH_3$ | |
| 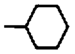 | H | H | H | H | H | O | $CH_3$ | $OCH_3$ | 127-130° |
| $CH_2-CH=CH_2$ | H | H | H | H | H | O | $CH_3$ | $OCH_3$ | 118-120° |
| $-(CH_2)_2OCH_3$ | H | H | H | H | $CH_3$ | S | $CH_3$ | $OC_2H_5$ | |
| $-CH_2-C_6H_5$ | H | H | H | H | H | O | $OCH_3$ | $OCH_3$ | |
| $-(CH_2)_4-$* | H | H | H | H | * | O | $CH_3$ | $OCH_3$ | |
| $-(CH_2)_5-$* | H | H | H | H | * | O | $CH_3$ | $OCH_3$ | 115-118° |
| $-(CH_2)_6-$* | H | H | H | H | * | O | $CH_3$ | $OCH_3$ | |
| n-$C_4H_9$ | H | H | H | H | n-$C_3H_7$ | S | $CH_3$ | $OCH_3$ | |
| $(CH_2)_6CH_3$ | H | H | H | H | n-$C_3H_7$ | O | $CH_3$ | $OCH_3$ | |
| $CH(CH_3)(CH_2)_4CH_3$ | H | H | H | H | H | O | $CH_3$ | $OCH_3$ | |
| cyclo-$C_8H_{15}$ | H | H | H | H | H | O | $CH_3$ | $OCH_3$ | |
| 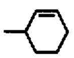 | H | H | H | H | H | O | $CH_3$ | $OCH_3$ | |
| 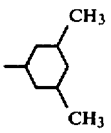 | H | H | H | H | H | O | $CH_3$ | $OCH_3$ | |
| 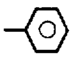 | H | H | H | H | H | O | $CH_3$ | $OCH_3$ | |
| 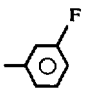 | H | H | H | H | H | O | $CH_3$ | $OCH_3$ | |

TABLE VIII-b-continued

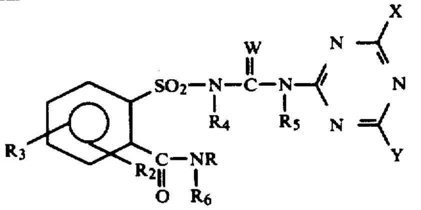

| R | $R_2$ | $R_3$ | $R_4$ | $R_5$ | $R_6$ | W | X | Y | m.p. °C. |
|---|---|---|---|---|---|---|---|---|---|
| 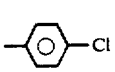 | H | H | H | H | H | O | $CH_3$ | $OCH_3$ | |
| 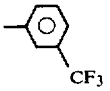 | H | H | H | H | H | O | $CH_3$ | $OCH_3$ | |
| 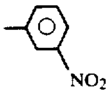 | H | H | H | H | H | O | $CH_3$ | $OCH_3$ | |
| 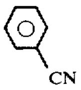 | H | H | H | H | H | O | $CH_3$ | $OCH_3$ | |
| $i\text{-}C_3H_7$ | H | H | H | H | H | O | $CH_3$ | $\underset{CH_3}{OCH}-CO_2CH_3$ | 125-130° |
| $-(CH_2)_5$* | H | H | H | H | * | O | Cl | Cl | 181-183° |
| $-(CH_2)_5$* | H | H | H | H | * | O | $OCH_3$ | $OCH_3$ | 158-161° |
| $C(CH_3)_3$ | H | H | H | H | H | O | $CH_3$ | $OCH_3$ | 118-121° |
| $CH_2C\equiv CH$ | H | H | H | H | H | O | $CH_3$ | $CH_3$ | |
| $C(CH_3)_2C\equiv CH$ | H | H | H | H | H | O | $CH_3$ | $CH_3$ | |
| $CH_2-C\equiv C-CH_3$ | H | H | H | H | H | O | $CH_3$ | $OCH_3$ | |
| $\underset{CH_3}{CH}-C\equiv C-CH_2CH_3$ | H | H | H | H | H | O | $CH_3$ | $OCH_3$ | |

*R and $R_6$ are taken together.

TABLE VIII-c

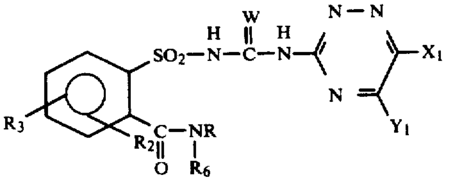

| R | $R_2$ | $R_3$ | W | $R_6$ | $X_1$ | $Y_1$ |
|---|---|---|---|---|---|---|
| H | H | H | O | H | $CH_3$ | $CH_3$ |
| $CH_3$ | H | H | O | H | $CH_3$ | $OCH_3$ |
| $CH_3$ | 5-Cl | H | S | H | $OCH_3$ | $OCH_3$ |
| $CH_3$ | 6-Cl | H | S | H | $CH_3$ | $CH_3$ |
| $C_2H_5$ | H | H | O | H | $CH_3$ | $CH_3$ |
| sec-$C_4H_9$ | H | H | O | H | $CH_3$ | $CH_3$ |

TABLE VIII-d

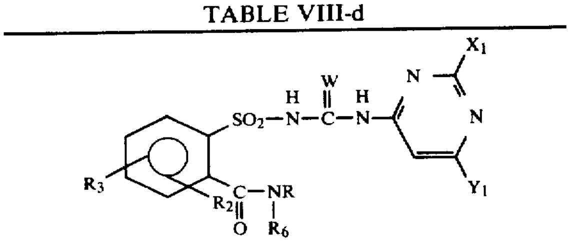

| R | $R_2$ | $R_3$ | W | $R_6$ | $X_1$ | $Y_1$ |
|---|---|---|---|---|---|---|
| $CH_3$ | H | H | O | H | $OCH_3$ | $CH_3$ |
| $C_2H_5$ | 5-Cl | H | O | H | $CH_3$ | $OCH_3$ |
| $i\text{-}C_3H_7$ | H | H | O | H | $CH_3$ | $CH_3$ |

EXAMPLE 21

N-[(4-methoxy-6-methyltriazin-2-yl)aminocarbonyl]-2-[methylthio)carbonylbenzenesulfonamide.

Trimethylaluminum (6.0 ml, 2 M) was charged via syringe to 15 ml dry toluene under nitrogen atmosphere and 3.8 g N-[(4-methoxy-6-methyltriazin-2-yl)aminocarbonyl]-2-methoxycarbonylbenzenesulfonamide was added portionwise. After stirring at room temperature for one hour, methyl mercaptan (gas) was passed through the reaction mixture until the initial temperature rise subsided, whereupon the addition was discontinued. The reaction mixture was allowed to stir at room temperature for 1 hour, and quenched with 25 ml of 10% HCl. The resultant white suspension was filtered to give 2.9 g white solid which showed infrared absorption peaks at 1740, 1690 $cm^{-1}$, consistent for N-[(4-methoxy-6-methyltriazin-2-yl)aminocarbonyl]-2-(methylthio)carbonylbenzenesulfonamide.

EXAMPLE 23

N-[(4-Methoxy-6-methyl-1,3,5-triazin-2-yl)aminocarbonyl]-2-isopropylthiocarbonylbenzenesulfonamide To 1.5 ml (2 N) trimethylaluminum in 5 ml dry toluene under $N_2$ was added dropwise 0.48 g (6.0 mmole) 2-propanethiol in 2 ml toluene. The resultant aluminum reagent was stirred at room temperature for 15 minutes, and 0.95 g (2.5 mmole) of N-[(4-methoxy-6-methyl-1,3,5-triazin-2-yl)aminocarbonyl]-2-methoxycarbonylbenzenesulfonamide was added in one portion. The suspension was heated to 80° C. for 3 hours, cooled to room temperature and 10% HCl (15 ml) was added. The mixture was stirred until a fine solid precipitated which was filtered off, washed with hexanes and air dried to yield 0.4 g of product melting at 155°-158° C. It showed infrared absorption peaks consistent for N-[(4-methoxy-6-methyl-1,3,5-triazin-2-yl)aminocarbonyl]-2-isopropylthiocarbonylbenzenesulfonamide.

By using the procedures of Examples 21-23 with equivalent amounts of an appropriately substituted dialkyl-aluminum alkylthiolate and appropriately substituted esters of this invention, the compounds of Table IX can be prepared.

TABLE IX-a

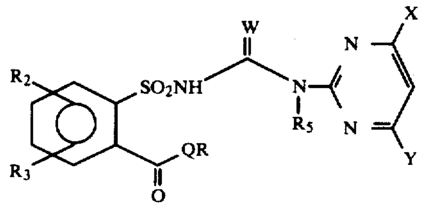

| QR | $R_2$ | $R_3$ | W | $R_5$ | X | Y | m.p. (°C.) |
|---|---|---|---|---|---|---|---|
| $SCH_3$ | H | H | O | H | $CH_3$ | $OCH_3$ | |
| $SCH_3$ | H | H | O | H | $CH_3$ | $CH_3$ | |
| $SC_2H_5$ | H | H | O | H | $OCH_3$ | $OCH_3$ | |
| S—n($C_7H_{15}$) | H | H | O | H | $OCH_3$ | $OCH_3$ | |
| $-SCHCH_3$<br>$CH_3$ | H | H | O | H | $OCH_3$ | $CH_3$ | 143-146° |
| $-SCHCH_2CH_3$<br>$CH_3$ | H | H | O | H | $CH_3$ | $CH_3$ | |
| $-SCH(CH_2)_9CH_3$<br>$CH_3$ | H | H | O | H | $OCH_3$ | $OCH_3$ | |
| $-SCHCH_2Cl$<br>$CH_3$ | H | H | O | H | $OCH_3$ | $CH_3$ | |
| $-SCH(CH_2)_3CH_3$<br>$CH_2-Cl$ | H | H | O | H | $OCH_3$ | $CH_3$ | |

TABLE IX-a-continued

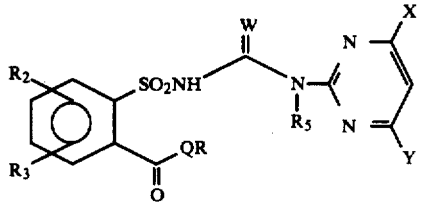

| QR | $R_2$ | $R_3$ | W | $R_5$ | X | Y | m.p. (°C.) |
|---|---|---|---|---|---|---|---|
| 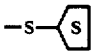 | H | H | O | H | $CH_3$ | $CH_3$ | |
| 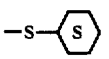 | H | H | O | H | $OCH_3$ | $CH_3$ | 133-136° |
| $S-CH-CH_2-CHBr$<br>$CH_3$ | H | H | O | H | $CH_3$ | $CH_3$ | |
| $-S-CH-CH_2CCl_3$<br>$CH_3$ | H | H | O | H | $CH_3$ | $CH_3$ | |
| —S—cyclo-$C_8H_{15}$ | H | H | O | H | $CH_3$ | $OCH_3$ | |
| 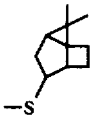 | H | H | O | H | $OCH_3$ | $CH_3$ | |
| 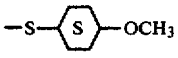 | H | H | O | H | $CH_3$ | $CH_3$ | |
| 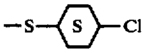 | H | H | O | H | $CH_3$ | $CH_3$ | |
| 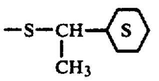 | H | H | O | H | $OCH_3$ | $OCH_3$ | |
| 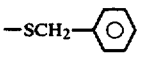 | H | H | O | H | $OCH_3$ | $CH_3$ | 148-150° |
| 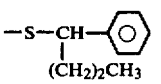 | H | H | O | H | $OCH_3$ | $CH_3$ | |
| 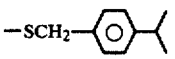 | H | H | O | H | $CH_3$ | $CH_3$ | |
| 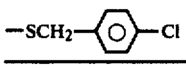 | H | H | O | H | $CH_3$ | $CH_3$ | |

TABLE IX-b

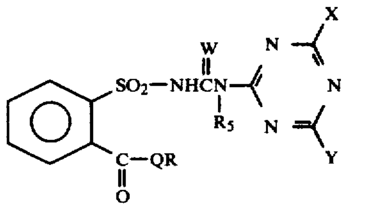

| QR | $R_2$ | $R_3$ | W | $R_5$ | X | Y | m.p. °C. |
|---|---|---|---|---|---|---|---|
| $SCH_3$ | H | H | O | H | $CH_3$ | $OCH_3$ | 144–146° |
| $SC_2H_5$ | H | H | O | H | $OCH_3$ | $OCH_3$ | |
| $S—n(C_5H_{11})$ | H | H | O | H | $OCH_3$ | $OCH_3$ | |
| $S—n(C_8H_{17})$ | H | H | O | H | $OCH_3$ | $OCH_3$ | |
| $S—n(C_4H_9)$ | H | H | O | H | $OCH_3$ | $CH_3$ | 115–120° |
| 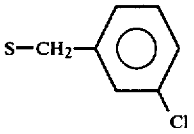 | H | H | O | H | $OCH_3$ | $CH_3$ | |
| 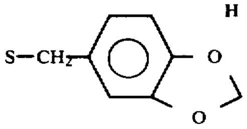 | H | H | O | H | $OCH_3$ | $CH_3$ | |
| 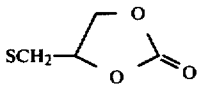 | H | H | O | H | $OCH_3$ | $CH_3$ | |
| 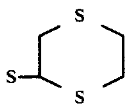 | H | H | O | H | $OCH_3$ | $CH_3$ | |
| 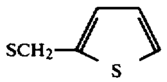 | H | H | O | H | $OCH_3$ | $CH_3$ | |
| 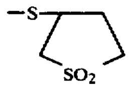 | H | H | O | H | $OCH_3$ | $CH_3$ | |
| 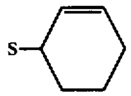 | H | H | O | H | $OCH_3$ | $CH_3$ | |
| $S(CH_2)_8CH=CH_2$ | H | H | O | H | $OCH_3$ | $CH_3$ | |
| $—SCHCH_3$<br>$CH_3$ | H | H | O | H | $OCH_3$ | $CH_3$ | 177–178 |
| $—SCHCH_2CH_3$<br>$CH_3$ | H | H | O | H | $OCH_3$ | $CH_3$ | |
| $—SCH(CH_2)_9CH_3$<br>$CH_3$ | H | H | O | H | $OCH_3$ | $OCH_3$ | |
| $—SCHCH_2Cl$<br>$CH_3$ | H | H | O | H | $CH_3$ | $CH_3$ | |

TABLE IX-b-continued

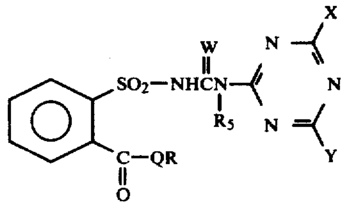

| QR | $R_2$ | $R_3$ | W | $R_5$ | X | Y | m.p. °C. |
|---|---|---|---|---|---|---|---|
| $—SCH(CH_2)_3CH_3$<br>$CH_2—Cl$ | H | H | O | H | $OCH_3$ | $CH_3$ | |
| 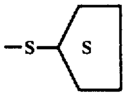 | H | H | O | H | $CH_3$ | $CH_3$ | |
| 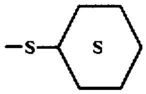 | H | H | O | H | $CH_3$ | $CH_3$ | |
| 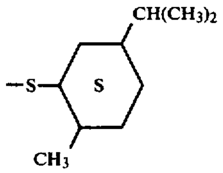 | H | H | O | H | $CH_3$ | $CH_3$ | |
| 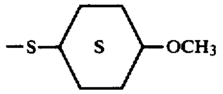 | H | H | O | H | $CH_3$ | $CH_3$ | |
| 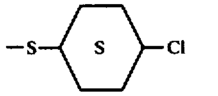 | H | H | O | H | $CH_3$ | $CH_3$ | |
| 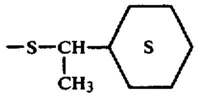 | H | H | O | H | $CH_3$ | $CH_3$ | |
| 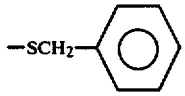 | H | H | O | H | $OCH_3$ | $CH_3$ | 125–130 |
| 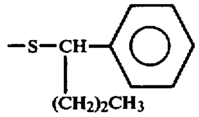 | H | H | O | H | $CH_3$ | $CH_3$ | |
| 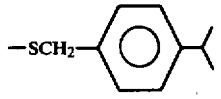 | H | H | O | H | $CH_3$ | $CH_3$ | |

TABLE IX-b-continued

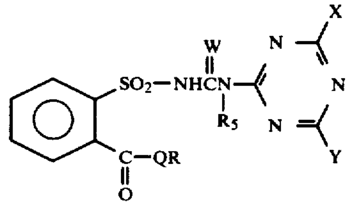

| QR | $R_2$ | $R_3$ | W | $R_5$ | X | Y | m.p. °C. |
|---|---|---|---|---|---|---|---|
| 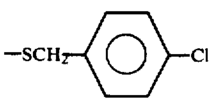 | H | H | O | H | $CH_3$ | $CH_3$ | |

TABLE IX-c

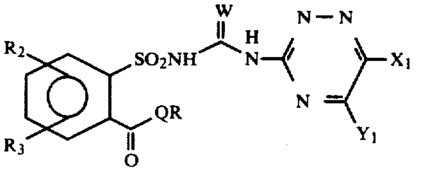

| QR | $R_2$ | $R_3$ | W | $X_1$ | $Y_1$ | m.p. (°C.) |
|---|---|---|---|---|---|---|
| $-SCHCH_3$<br>$CH_3$ | H | H | O | $CH_3$ | $CH_3$ | |
| $-SCHCH_2CH_3$<br>$CH_3$ | H | H | O | $OCH_3$ | $CH_3$ | |
| $-SCH_2CH_3$ | H | H | O | $OCH_3$ | $CH_3$ | |
| 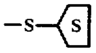 | H | H | O | $CH_3$ | $CH_3$ | |
| $-S-CH-CH_2CCl_3$<br>$CH_3$ | H | H | O | $CH_3$ | $CH_3$ | |
| $S-n(C_3H_7)$ | H | H | O | $OCH_3$ | $OCH_3$ | |
| $SCH_3$ | H | H | O | $CH_3$ | $CH_3$ | |

TABLE IX-d

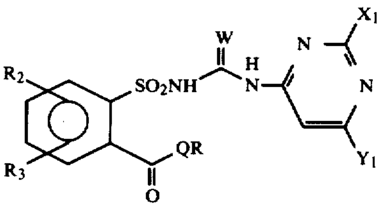

| QR | $R_2$ | $R_3$ | W | $X_1$ | $Y_1$ | m.p.(°C.) |
|---|---|---|---|---|---|---|
| $-SCHCH_3$<br>$CH_3$ | H | H | O | $OCH_3$ | $CH_3$ | |
| $-SCHCH_2CH_3$<br>$CH_3$ | H | H | O | $OCH_3$ | $CH_3$ | |

TABLE IX-d-continued

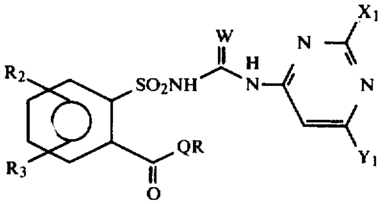

| QR | $R_2$ | $R_3$ | W | $X_1$ | $Y_1$ | m.p.(°C.) |
|---|---|---|---|---|---|---|
| 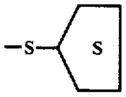 | H | H | O | $OCH_3$ | $OCH_3$ | |
| $-S-CH-CH_2CCl_3$<br>$CH_3$ | H | H | O | $CH_3$ | $CH_3$ | |
| $SCH_3$ | H | H | O | $CH_3$ | $OCH_3$ | |
| $S-n(C_5H_{11})$ | H | H | O | $OCH_3$ | $OCH_3$ | |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table X.

TABLE X

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions (including Emulsifiable Concentrates) | 3-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |

*Active Ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates, solution concentrates are preferably stable against phase separation at 0° C. "McCutcheon's Detergents and Emulsifiers Annual", MC Publishing Corp., Ridgewood, New Jersey, as well as Sisely and Wood, "Enclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually, grinding as in a hammer or fluid energy mill. Suspensions are prepared by wet milling (see, for example, Littler, U.S. Pat. No. 3,060,084). Granules and pellets may be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, Col, 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed. Blackwell Scientific Publications, Oxford, 1968, pp. 101–103.

Unless indicated otherwise, all parts are by weight in the following examples.

EXAMPLE 24

Wettable Powder:

N-[(4,6-dimethoxy-pyrimidin-2-yl)aminocarbonyl]-2-methoxycarbonylbenzenesulfonamide: 95%
dioctyl sodium sulfosuccinate: 0.1%
sodium ligninsulfonate: 1%
synthetic fine silica: 4%

The ingredients are blended and ground in a hammer-mill to produce particles almost all of which are below 100 microns in size. That material is sifted through a U.S.S. No. 50 screen and packaged.

EXAMPLE 25

Granule wettable powder of Example 24: 10%
attapulgite granules (U.S.S. #20-40; 0.84–0.42 mm): 90%

A slurry of wettable powder containing 50% solids is sprayed onto the surface of attapulgite granules in a double-cone blender. The granules are dried and packaged.

EXAMPLE 26

Wettable Powder

N[(4-methoxy-6-methyl-1,3,5-triazin-2-yl)aminocarbonyl]-2-methoxycarbonylbenzenesulfonamide: 40%
dioctyl sodium sulfosuccinate: 1.5%
sodium ligninsulfonate: 3%
low viscosity methyl cellulose: 1.5%
attapulgite: 54%

The ingredients are thoroughly blended and passed through an air mill to produce an average particle size under 15 microns, reblended, and sifted through a U.S.S. No. 50 sieve (0.3 mm opening) before packaging.

EXAMPLE 27

Granule wettable powder of Example 26: 25%
gypsum: 64%
potassium sulfate: 11%

The ingredients are blended in a rotating mixer, and water is sprayed onto that blend so as to effect granulation. When most of the granules have reached 1.0 to 0.42 mm (U.S.S. #18 to 40 sieves) in size, they are removed, dried, and screened. Oversize material is crushed to produce additional material in the desired range. The resulting granules contain 10% of the active ingredient.

EXAMPLE 28

Wettable Powder

N-[(4,6-dimethoxy-1,3,5-triazin-2-yl)aminocarbonyl]-2-methoxycarbonylbenzenesulfonamide: 65%
dodecylphenol polyethylene glycol ether: 2%
sodium ligninsulfonate: 4%
sodium silicoaluminate: 6%
montmorillonite (calcined): 23%

The ingredients are thoroughly blended. The liquid surfactant is added by spraying on the solid ingredients in a blender. After grinding in a hammer mill to produce particles almost all of which are below 100 microns in size, the material is reblended, sifted through a U.S.S. #50 sieve (0.3 mm opening) and packaged.

EXAMPLE 29

Oil Suspension
N-[(4-methoxy-6-methylpyrimidin-2-yl)aminocarbonyl]-2-methoxycarbonylbenzenesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting suspension may be applied directly, but preferably after being extended further with oils or emulsified in water.

EXAMPLE 30

Aqueous Suspension

N-[(4,6-dimethyl-1,3,5-triazin-2-yl)aminocarbonyl]-2-methoxycarbonylbenzenesulfonamide 25%
hydrated attapulgite: 3%
crude calcium ligninsulfonate: 10%
sodium dihydrogen phosphate: 0.5%
water: 61.5%

The ingredients are ground together in a ball or roller mill until the solid particles have been reduced to sizes under 10 microns, and then packaged.

EXAMPLE 31

Extruded Pellet

N-[(4,6-dimethylpyrimidin-2-yl)aminocarbonyl]-2-methoxycarbonylbenzenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer milled and then moistened with about 12% water. The mixture is extruded in the form of cylinders about 3 mm in diameter which are cut to produce pellets about 3 mm long. The pellets may be used directly, after drying, or dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 32

Solution

N-[(4,6-dimethoxy-1,3,5-triazin-2-yl)aminocarbonyl]-2-methoxycarbonylbenzenesulfonamide: 5%
dimethylformamide: 95%

The ingredients are combined and stirred to produce a solution, which can be used for low volume applications.

EXAMPLE 33

Wettable Powder

N-[(4,6-dimethoxy-1,3,5-triazin-2-yl)aminocarbonyl]-2-isopropoxycarbonyl benzenesulfonamide: 80%
sodium alkylnaphthalenesulfonate: 2%
sodium ligninsulfonate: 2%
synthetic amorphous silica: 3%
kaolinite: 13%

The ingredients are thoroughly blended after grinding in a hammer mill to produce particles essentially all of which are under 100 microns in size; the material is reblended, sifted through a U.S.S. No. 50 sieve and packaged.

EXAMPLE 34

Tank Mix

Wettable Powder of Example 33: 2.5 gm
An alkylarylpolyglycol ether type spreader/sticker adjuvant: 0.6 liter A tank mix of these materials may be made by adding these ingredients (in the amounts given) to 300 liters of water in a spray tank. After agitation, this suspension is applied to 1 hectare of land. Larger spray tanks and land areas may be used if the materials are used in the same proportions.

For good spraying properties, the wettable powders should be added first and be properly dispersed before adding the adjuvant. Then the mixture may be sprayed using conventional spraying techniques.

EXAMPLE 35

Tank Mix

Wettable Powder of Example 33: 2.5 gm
Citowett® Plus (Spreader/Sticker Adjuvant by BASF): 0.3 liter Specifically, a tank mix of these materials may be made by adding these ingredients (in the amounts given) to 300 liters of water in a spray tank. After agitation, this suspension is applied to 1 hectare of land. Larger spray tanks may be used and larger land areas sprayed if the materials are used in the same proportions.

For good spraying properties, the wettable powder should be added first and be properly dispersed before adding the adjuvant. Then, the mixture may be sprayed using conventional spraying techniques.

The compounds of this invention may be used in combination with other commercial herbicides. They are particularly useful in combination with the following herbicides:

| Common Name | Chemical Name |
|---|---|
| acifluorfen | 5-[2-chloro-4-(trifluoromethyl)phenoxy]-2-nitrobenzoic acid |
| acrolein | acrolein |
| alachlor | 2-chloro-2',6'-diethyl-N—(methoxymethyl)-acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N—butyl-N—ethyl-α,α,α-trifluoro-2,6-dinitro-p-toluidine |
| bensulide | O,O—diisopropyl phosphorodithioate S—ester with N—(2-mercaptoethyl)benzene-sulfonamide |
| benzipram | 3,5-dimethyl-N—(1-methylethyl)-N—(phenylmethyl)benzamide |
| benzoylprop | N—benzoyl-N—(3,4-dichlorophenyl)-DL-alanine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N—(butoxymethyl)-2-chloro-2',6'-diethyl-acetanilide |
| butam | 2,2-dimethyl-N—(1-methylethyl)-N—(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methyl-propyl)-2,6-dinitrobenzenamide |
| cacodylic acid | hydroxydimethylarsine oxide |
| carbetamide | D-N—ethyllactamide carbanilate (ester) |
| CDAA | N—N—diallyl-2-chloroacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| cisanilide | cis-2,5-dimethyl-N—phenyl-1-pyrrolidine-carboxamide |
| CMA | calcium methanearsonate |
| cyanazine | 2-[[4-chloro-6-(ethylamino)-s-triazin-2-yl]amino]-2-methylpropionitrile |
| cycloate | S—ethyl N—ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(iso-propylamino)-s-triazine |
| cyprazole | N—[5-(2-chloro-1,1-dimethylethyl)-1,3,4-thiadiazol-2-yl] cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H-1,3,5-thia-diazine-2-thione |
| DCPA | dimethyl tetrachloroterephthalate |
| desmetryn | 2-(isopropylamino)-4-(methylamino)-6-methylthio)-s-triazine |

-continued

| Common Name | Chemical Name |
|---|---|
| diallate | S—(2,3-dichloroallyl)diisopropyl-thiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-diclorophenoxy)phenoxy]propanoic acid |
| diethatyl | N—(chloroacetyl)-N—(2,6-diethylphenyl)glycine |
| difenzoquat | 1,2-dimethyl-3,5-diphenyl-1H-pyrazolium |
| dinitramine | $N^4$,$N^4$—diethyl-$\alpha$,$\alpha$,$\alpha$-trifluoro-3,5-dinitro-toluene-2,4-diamine |
| dinoseb | 2-sec-butyl-4,6-dinitrophenol |
| diphenamid | N,N—dimethyl-2,2-diphenylacetamide |
| dipropetryn | 2-(ethylthio)-4,6-bis(isopropylamino)-s-triazine |
| diquat | 6,7-dihydrodipyrido[1,2-$\alpha$:2',1'-c]pyra-zinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloro-propionate |
| ethafluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenuron | 1,1-dimethyl-3-phenylurea |
| fenuron TCA | 1,1-dimethyl-3-phenylurea mono(trichloro-acetate) |
| flamprop | N—benzoyl-N—(3-chloro-4-fluorophenyl)-DL-alanine |
| fluchloralin | N—(2-chloroethyl)-2,6-dinitro-N—propyl-4-(trifluoromethyl)analine |
| fluometuron | 1,1-dimethyl-3-($\alpha$,$\alpha$,$\alpha$-trifluoro-m-tolyl)urea |
| fluorodifen | p-nitrophenyl $\alpha$,$\alpha$,$\alpha$-trifluoro-2-nitro-p-tolyl ether |
| fluridone | 1-methyl-3-phenyl-5-[3-(trifluoromethyl)-phenyl]-4(1H)-pyridinone |
| fosamine | ethyl hydrogen (aminocarbonyl)phosphonate |
| glyphosate | N—(phosphonomethyl)glycine |
| hexaflurate | potassium hexafluoroarsenate |
| hexazinone | 3-cyclohexyl-6-(dimethylamino)-1-methyl-1,3,5-triazin-2,4(1H,3H)-dione |
| ioxynil | 4-hydroxy-3,5-diiodobenzonitrile |
| isopropalin | 2,6-dinitro-N,N—dipropylcumidine |
| karbutilate | tert-butylcarbamic acid ester with 3(m-hydroxyphenyl)-1,1-dimethylurea |
| lenacil | 3-cyclohexyl-6,7-dihydro-1H-cyclopenta-pyrimidine-2,4(3H,5H)-dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N—[(2,4-dimethyl-5-[[(trifluoromethyl)sul-fonyl]amino]phenyl]acetamide |
| methalpropalin | N—(2-methyl-2-propenyl)-2,6-dinitro-N—propyl-4-(trifluoro-methyl)benzenamide |
| metham | sodium methyldithiocarbamate |
| methazole | 2-(3,4-dichlorophenyl)-4-methyl-1,2,4-oxadiazolidine-3,5-dione |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazin-5(4H)-one |
| molinate | S—ethyl hexahydro-1H-azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono-(trichloroacetate) |
| MSMA | monosodium methanearsonate |
| napropamide | 2-($\alpha$-naphthoxy)-N,N—diethylpropionamide |
| naptalam | N—1-napthylphthalamic acid |
| neburon | 1-butyl-3-(3,4-dichlorophenyl)-1-methylurea |
| nitralin | 4-(methylsulfonyl)-2,6-dinitro-N,N— dipropyl-aniline |

-continued

| Common Name | Chemical Name |
|---|---|
| nitrofen | 2,4-dichlorophenyl p-nitrophenyl ether |
| nitrofluorfen | 2-chloro-1-(4-nitrophenoxy)-4-(trifluoro-methyl)benzene |
| norea | 3-(hexahydro-4,7-methanoindan-5-yl)-1,1-dimethylurea |
| norflurazon | 4-chloro-5-(methylamino)-2-($\alpha$,$\alpha$,$\alpha$-trifluoro-m-tolyl)-3(2H)-pyridazinone |
| oryzalin | 3,5-dinitro-$N^4$,$N^4$—dipropylsulfanilamide |
| oxadiazon | 2-tert-butyl-4-(2,4-dichloro-5-isopropoxy-phenyl)$\Delta^2$-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N—(1-ethylpropyl)-3,4-dimethyl-2,6-dinitro-benzenamine |
| perfluidone | 1,1,1-trifluoro-N—[2-methyl-4-(phenylsul-fonyl)phenyl]methanesulfonamide |
| picloram | 4-amino-3,5,6-trichloropicolinic acid |
| procyazine | 2-[[4-chloro-6-(cyclopropylamino)-1,3,5-traizine-2-yl]amino]-2-methylpropanenitrile |
| profluralin | N—(cyclopropylmethyl)-$\alpha$,$\alpha$,$\alpha$-trifluoro-2,6-dinitro-N—propyl-p-toluidine |
| prometon | 2,4-bis(isopropylamino)-6-methoxy-s-triazine |
| prometryn | 2,4-bis(isopropylamino)-6-(methylthio)-s-traizine |
| pronamide | 3,5-dichloro(N—1,1-dimethyl-2-propynyl)-benzamide |
| propachlor | 2-chloro-N—isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N—[[4-(dipropylamino)-3,5-dinitrophenyl]-sulfonyl]-S,S—dimethylsulfilimine |
| prynachlor | 2-chloro-N—(1-methyl-2-propynyl)acetanilide |
| secbumeton | N—ethyl-6-methoxy-N'(1-methylpropyl)-1,3,5-triazine-2,4-diamine |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| TCA | trichloroacetic acid |
| tebuthiuron | N—[5-(1,1-dimethylethyl)-1,3,4-thiadiazol-2-yl]-N,N' —dimethylurea |
| terbacil | 3-tert-butyl-5-chloro-6-methyluracil |
| terbuchlor | N—(butoxymethyl)-2-chloro-N—[2-(1,1-dimethylethyl)-6-methylphenyl]acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-(methyl-thio)-s-triazine |
| tetrafluron | N,N—dimethyl-N'—[3-(1,1,2,2-tetrafluoroethoxy)phenyl]urea |
| thiobencarb | S—[(4-chlorophenyl)methyl]-diethylcarbamothioate |
| triallate | S—(2,3,3-trichloroallyl)-diisopropylthiocarbamate |
| trifluralin | $\alpha$,$\alpha$,$\alpha$-trifluoro-2,6-dinitro-N,N—dipropyl-p-toluidine |
| trimeturon | 1-(p-chlorophenyl)-2,3,3-trimethylpseudourea |
| 2,3,6-TBA[b] | 2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |
| methabenzthiazuron | 1,3-dimethyl-3-(2-benzothiazolyl)urea |
| chlortoluran | N'—(3-chloro-4-methyl-phenyl)-N'N—dimethylurea |
| isoproturan | N—(4-isopropylphenyl)-N'N'—dimethylurea |
| metoxuran | N'—(3-chloro-4-methoxyphenyl)-N,N—dimethylurea |

UTILITY

The compounds of the present invention are highly active herbicides. They have utility for broad-spectrum pre- and/or post-emergence weed control in areas where complete control of all vegetation is desired, such as around fuel storage tanks, ammunition depots, industrial storage areas, oil well sites, drivein theatres, around billboards, highway and railroad structures. By properly selecting rate and time of application, compounds of this invention may be used also to modify plant growth beneficially and for the selective control of weeds in crops such as wheat and barley.

The precise amount of the compound of Formula I to be used in any given situation will vary according to the particular end result desired, the amount of foliage present, the weeds to be controlled, the crop species, the soil type, the formulation and mode of application, weather conditions, etc. Since so many variables play a role, it is not possible to state a rate of application suitable for all situations. Broadly speaking, the compounds of this invention are used at levels of about 0.005 to 20 kg/ha with a preferred range of 0.125 to 10 kg/ha. In general, the higher rates of application from within this range will be selected for adverse conditions or where extended persistence in soil is desired and the lower rates for selective weed control in crops.

The activity of these compounds was discovered in a number of greenhouse and field tests. The tests are described and the data resulting from them are shown below. The ratings are based on a numerical scale extending from 0=no effect, to 10=maximum effect. The accompanying descriptive symbols have the following meanings:

C=chlorosis or necrosis
D=defoliation
E=emergence inhibition
G=growth retardation
H=formative effects
U=unusual pigmentation
6Y=abscised buds or flowers

TEST A

Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated preemergence with a nonphytotoxic solvent solution of the compounds of Table XII. Other batches of seeds and tubers for all of the foregoing weed and crop plants were planted at the same time as controls. The control plantings were untreated; i.e., neither any compound nor any solvent was applied. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds of Table XII. Other groups of all the same weed and crop plants were sprayed with the same nonphytotoxic solvent so as to provide control plants. Preemergence and postemergence treated plants and controls were maintained in a greenhouse for sixteen days, then all treated plants were compared with their respective controls and rated visually for response to treatment. The data in Table XII shows that the compounds of this invention are very effective as herbicides.

TABLE XII
| | | POST EMERGENCE | | | | | | | | | | | | | |
|---|---|---|---|---|---|---|---|---|---|---|---|---|---|---|---|
| | kg/ha | BUSH-BEAN | COT-TON | MORN-ING-GLORY | COCK-LEBUR | CAS-SIA | NUTS-EDGE | CRAB-GRASS | BARN-YARD GRASS | WILD OATS | WHEAT | CORN | SOY-BEAN | RICE | SOR-GHUM |
| 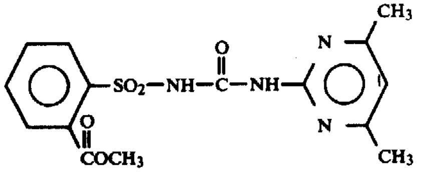 | 0.4<br>2.0 | 9C<br>9C | 9C<br>9C | 10C<br>10C | 10C<br>9C | 9C<br>9C | 9C<br>9C | 9C<br>9C | 10C<br>10C | 9C<br>9C | 9C<br>9C | 9C<br>9C | 9C<br>6C 9G | 10C<br>10C | 9C<br>10C |
| 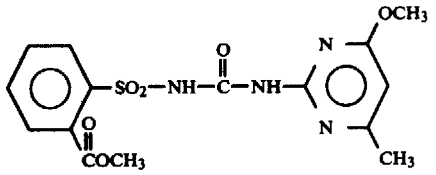 | 0.4 | 9C | 9C | 10C | 9C | 9C | 9C | 5C 9G | 9C | 9C | 9C | 10C | 9C | 5C 9G | 9C |
| 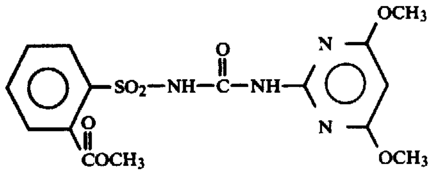 | 0.4 | 9C | 9C | 10C | 9C | 9C | 10C | 5C 8G | 9C | 9C | 9C | 9C | 9C | 8C | 9C |
| 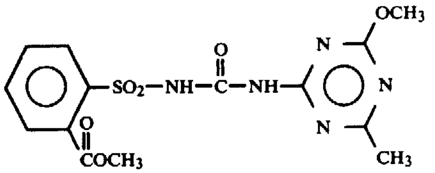 | 0.4 | 9C | 9C | 10C | 9C | — | 9C | 10C | 10C | 10C | 10C | 10C | 9C | 10C | 10C |
| 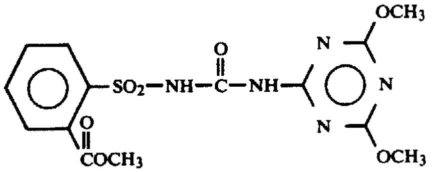 | 0.4 | 9C | 5U 5C 9G | 10C | 9C | 9C | 9C | 9C | 10C | 4C 7G | 3C 7G | 10C | 9C | 10C | 9C |

TABLE XII-continued
| | | | | | | | | | | | | | | | | |
|---|---|---|---|---|---|---|---|---|---|---|---|---|---|---|---|---|
| 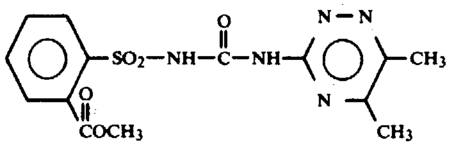 | 2 | 5C 10D | 5C 9G | 5C 9G | 9C | 9C | 9C | 9C | 9C | 9C | 10C | 5U 9C | 9C | 9C | 9C |
| 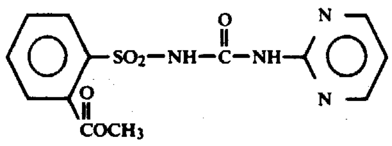 | 2 | 6C 9G | 3C 9G | 5C 8G | 5C 9G | 3C 6G | 1C 8G | 5C 8G | 9C | 2G | 5G | 1C 8G | 2C 8G | 3C 8G | 2C 8G |
| 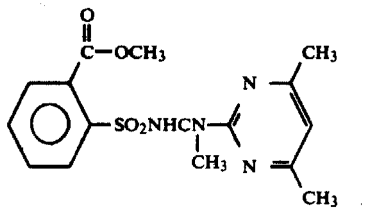 | 0.4 | 3C,8G, 6Y | 3C,9G | 3C,9G | 2C,7G | 2C | 7G | 7G | 9C | 6C | 2C,6G | 1C,8G | 3C | 3C,8G | 2C,8G |
| 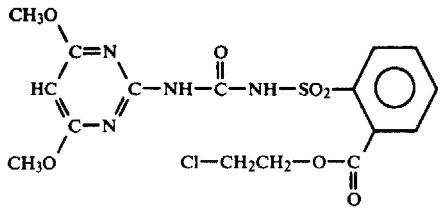 | 0.4 | 9C | 9C | 10C | 10C | 9C | 9C | 2C,6G | 10C | 2C,6G | 3C,6G | 2U,9G | 10C | 3C,8G | 10C |
| 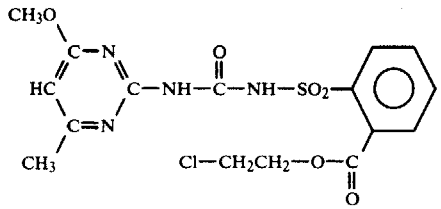 | 0.4 | 9C | 9C | 10C | 10C | 10C | 10C | 3C,7G | 10C | 2C,8G | 3C,7G | 10C | 5C,9G | 3C,8G | 9C |

TABLE XII-continued
| | | | | | | | | | | | | | | | |
|---|---|---|---|---|---|---|---|---|---|---|---|---|---|---|---|
| 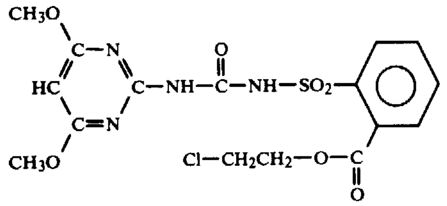 | 0.4 | 9C | 9C | 10C | 10C | 10C | 10C | 2C | 2C,9H | 2C,5G | 1C | 3C,9G | 3C,9G | 6G | 2H,8G |
| 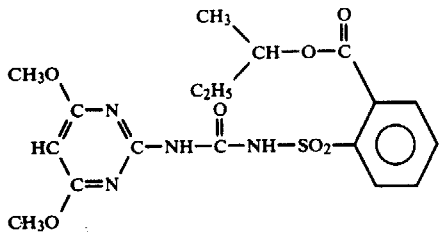 | 0.4 | 9D,9G | 6C,9G | 9C | 6C,9G | 5C,8G | 7G | 2A | 9C | 2C | 1C | 9H | 9C | 4C,8G | 2C,9G |
| 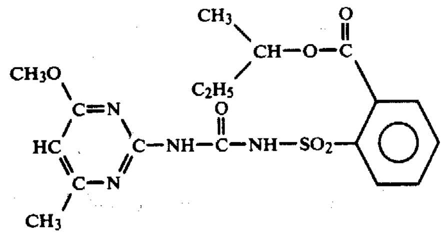 | 0.4 | 9D,9G | 7C,9G | 10C | 9C | 5C,8G | 8G | 0 | 5C,9H | 8G | 5C,8G | 5C,9H | 3C,9G | 5C,9G | 3C,9G |
| 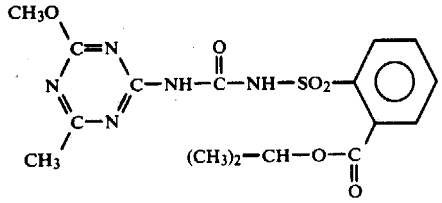 | 0.4 | 9C | 9C | 10C | 10C | 10C | 10C | 5C,8G | 6C,9H | 2C,6G | 2C | 10C | 5C,9G | 5C,8G | 5C,9G |

TABLE XII-continued
| | | | | | | | | | | | | | | | |
|---|---|---|---|---|---|---|---|---|---|---|---|---|---|---|---|
| 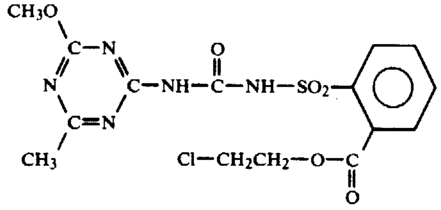 | 0.4 | 9C | 9C | 10C | 10C | 9C | 9C | 2C,5G | 2C,8H | 4G | 1C | 9C | 6C,9G | 1C,7G | 2U,9G |
| 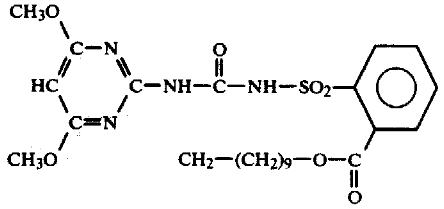 | 0.4 | 5C,8G, 6Y | 2C,2H, 7G | 1C | 3C,9G | 5G | 2G | 2G | 3C,9H | 1C | 1C | 3U,9G | 1H | 8G | 9G |
| 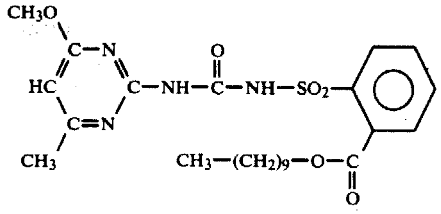 | 0.4 | 6C,6G, 6Y | 2C,2H, 7G | 2C,8G | 4C,9G | 5G | 7G | 0 | 3C,9H | 5G | 3C | 2C,9G | 2H,5G | 2C,9G | 2U,9G |
| 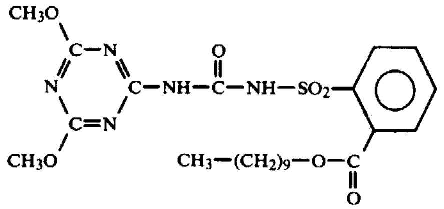 | 0.4 | 6C,8G, 6Y | 2C,2H, 8G | 1C,8G | 2C,9G | 5G | 3G | 3G | 1C | 0 | 0 | 6H | 7G | 2G | 7H |
| 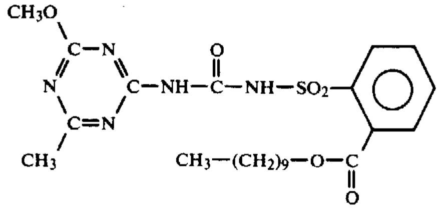 | 0.4 | 8C,5G, 6Y | 2C,2H, 8G | 3C,7G | 5C,9G | 2C,5G | 2G | 0 | 2H | 0 | 0 | 7H | 6H | 6G | 2C,9G |

TABLE XII-continued
| | | | | | | | | | | | | | | | |
|---|---|---|---|---|---|---|---|---|---|---|---|---|---|---|---|
| 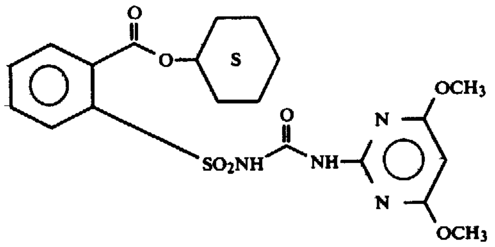 | 0.4 | 5S,8G, 6Y | 3C,3H, 9G | 9C | 9C | 1C | 1C,5G | 1C,5G | 5C,9H | 2C,5G | 1C | 7H | 2H,9G | C | 8H |
| 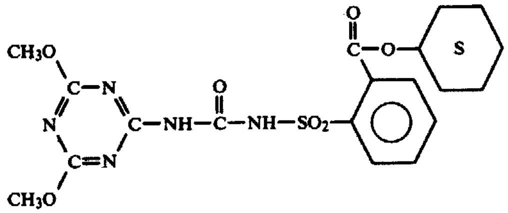 | 0.4 | 6C,8G, 6Y | 2H,3C, 8G | 6C,9G | 3C,9G | 5C | 2G | 0 | 3C,8H | 0 | 0 | 6H | 2H,8G | 2G | 3G |
| 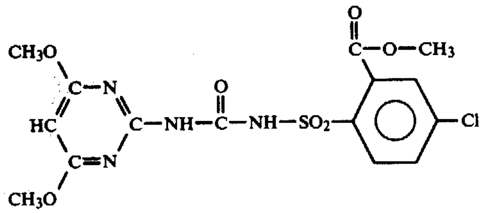 | 0.4 | 9C | 9C | 10C | 10C | 9C | 10C | 2C,6G | 3C,9H | 9G | 1C,2G | 6H | 5C,9G | 5C,9G | 3C,9G |
| 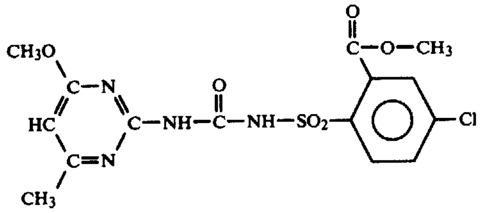 | 0.4 | 9C,9G | 9C,9G | 10C | 10C | 9C | 6C,9G | 3G | 6C,9H | 3C,9G | 3C,5G | 9H | 4C,9G | 9C | 4C,9G |

TABLE XII-continued
| | | | | | | | | | | | | | | | |
|---|---|---|---|---|---|---|---|---|---|---|---|---|---|---|---|
| 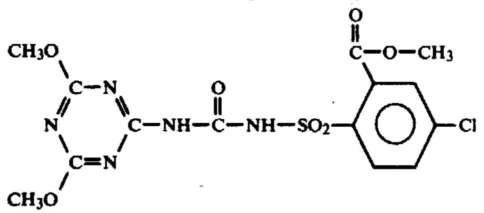 | 0.4 | 9C,9G | 7C,9G | 10C | 10C | 6C,9G | 10C | 1C | 3G | 0 | 0 | 9H | 5C,9G | 2C,9G | 8H |
| 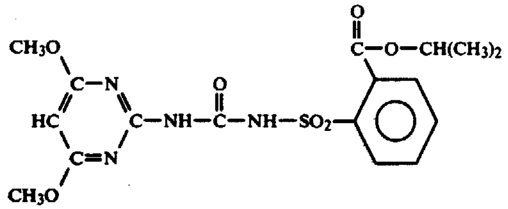 | 0.4 | 5H,8C | 9C | 10C | 10C | 9C | 9C | 6C | 9C | 6C | 3G,4G | 5U,8G | 6H,8G | 7C | 9C |
| 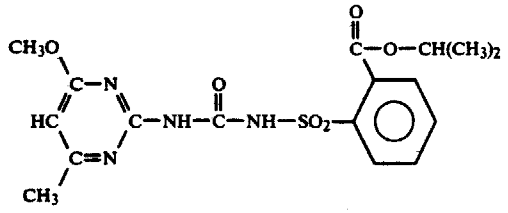 | 0.4 | 5C,9H | 10C | 9C | 10C | 9C | 9C | 3U,5G | 10C | 3C,7G | 3C,8G | 9C | 5H,9G | 8C | 10C |
| 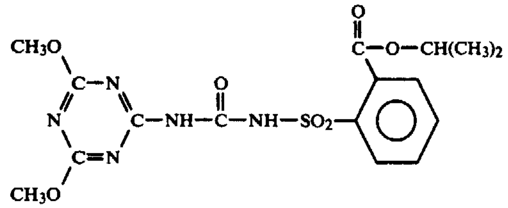 | 0.4 | 8H,9G | 9C | 10C | 10C | 9C | 9C | 6G | 8C | 2C | 2C | 5H,7G | 5H,8G | 8C | 2H,7G |
| 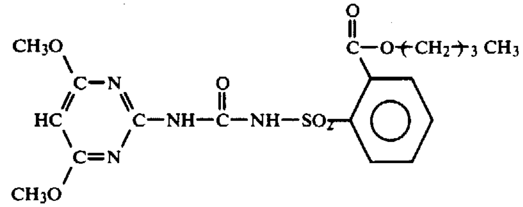 | 2 | 3C,9G, 9D | 9C | 10C | 9C | 9C | 9C | 4C,7G | 10C | 9C | 9C | 9C | 6C,9G | 9C | 9C |
| | 0.4 | 3C,9G, 9D | 4C,9G | 9C | 9C | 3C,7G | 2C,6G | 2C,6G | 9C | 2C,5G | 1C,4G | 2U,8H | 6C,9G | 6C,8G | 3C,8G |

TABLE XII-continued
| | | | | | | | | | | | | | | | |
|---|---|---|---|---|---|---|---|---|---|---|---|---|---|---|---|
| 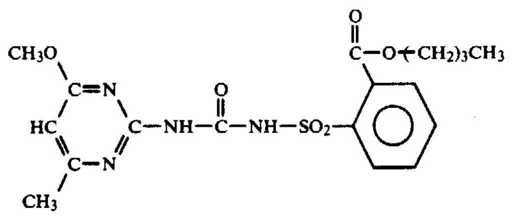 | 2 | 3C,9G, 10D | 5C,9G | 10C | 10C | 9C | 9C | 5C,8G | 10C | 4C,8G | 8C | 9C | 9C | 8C | 9C |
| | 0.4 | 3C,9G, 9D | 5C,9G | 9C | 9C | 3C,7G | 2C,7G | 3G | 10C | 8G | 4C,8G | 5C,9G | 4C,8G | 5C,8G | 2C,8G |
| 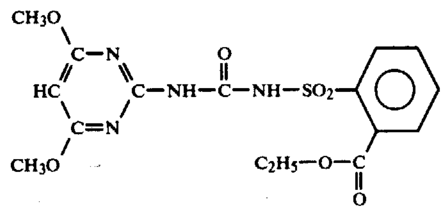 | 2 | 9G,10D | 9C | 10C | 9C | 9C | 9C | 9C | 10C | 9C | 9C | 9C | 6C,9G | 9C | 10C |
| 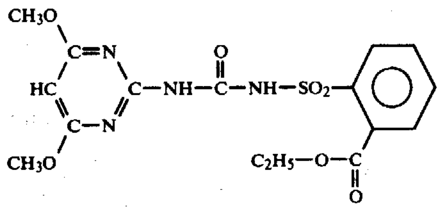 | 0.4 | 3C,9G, 9D | 9C | 10C | 9C | 9C | 9C | 4C,7G | 10C | 9C | 9C | 9C | 6C,9G | 9C | 9C |
| 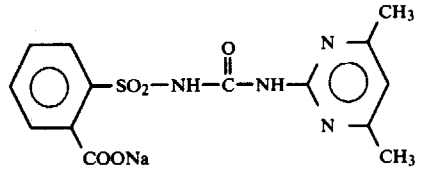 | 2 | 5H,8G, 6F | 4C,7G | 4G | 8C | 3C,8G | 8C | 5G | 8C | 4C | 4C | 3H,8G | 6H,9G | 9C | 3H,8G |
| | 2 | 1C | | 0 | 0 | 0 | 0 | 0 | 1H | 0 | 0 | 0 | 1C | 3G | 1C,5G |
| 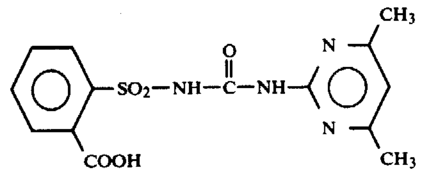 | 10 | 2C,2H | | 0 | 0 | 0 | 0 | 0 | 2G | 0 | 0 | 0 | 1C | 5G | 3G |
| | 2 | 1C | | 0 | 0 | 1C | 0 | 0 | 0 | 0 | 0 | 0 | 0 | 0 | 0 |
| | 2 | 0 | 0 | 0 | 0 | 0 | 0 | 0 | 0 | 0 | 0 | 0 | 0 | 0 | 0 |
| | 0.4 | 0 | 0 | 0 | 0 | 0 | 0 | 2G | 1C,2H | 0 | 0 | 0 | 0 | 0 | 0 |

TABLE XII-continued
| | | | | | | | | | | | | | | | |
|---|---|---|---|---|---|---|---|---|---|---|---|---|---|---|---|
| 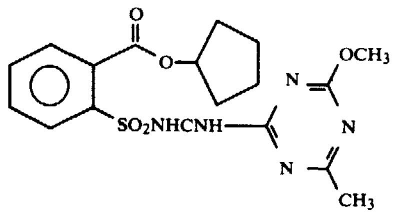 | 0.4 | 8C | 6C,9G | 10C | 9C | 5C,7G | 7G | 1C | 1C,7G | 1C | 1C | 3U,8G | 9C | 3C,7G | 8G |
| 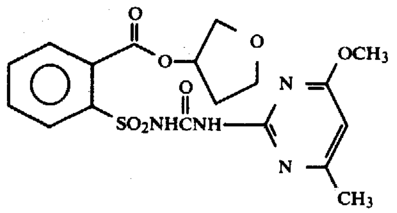 | 0.4 | 9C | 5C,9G | 9C | 5C,9G | 5C,9G | 3C,8G | 2C,8G | 9C | 7G | 7C | 5U,9C | 9C | 5C,8G | 9C |
| 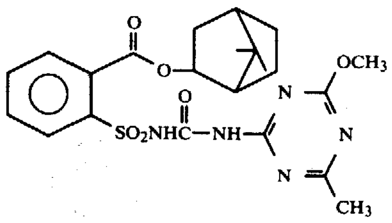 | 0.4 | 9C | 5C,9G | 5C,9G | 6G | 9C | 4G | 3G | 2G | 0 | 2G | 8G | 9C | 2C,5G | 1C,9G |
| 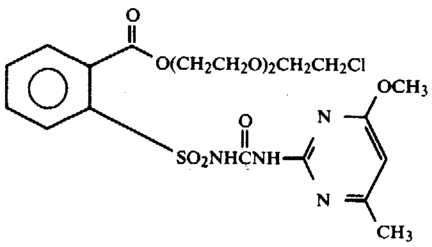 | 0.4 | 9C | 9C | 10C | 9C | 9C | 2C,6G | 3C,8G | 10C | 9C | 9C | 5U,8G | 8C | 8C | 5C,9G |

TABLE XII-continued
| | | | | | | | | | | | | | | | |
|---|---|---|---|---|---|---|---|---|---|---|---|---|---|---|---|
| 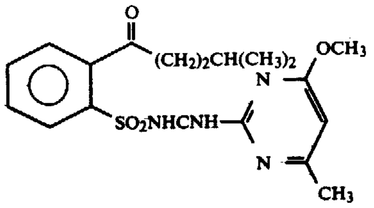 | 0.4 | 10D | 3C,9G | 10C | 5C,9G | 3C,8G | 2C,9G | 5C,8G | 9C | 5C,7G | 3C,9G | 9H | 2C,9G | 5C,9G | 3U,9G |
| 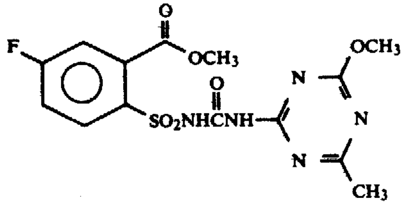 | 0.4 | 9C | 5C,9G | 9C | 3H,9G | 9C | 6C,9G | 9C | 5C,8H | 0 | 0 | 9C | 5C,9G | 9C | 2C,9G |
| 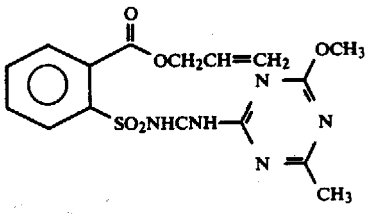 | 0.4 | 9C | 5C,9G | 10C | 10C | 9C | 6C,9G | 2C,6G | 9C | 9C | 9C | 9C | 9C | 9C | 9C |
| 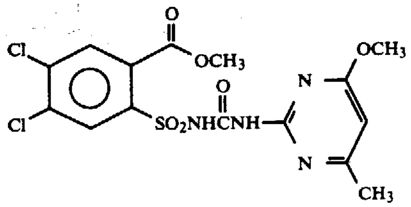 | 0.4 | 4C,9G, 6Y | 2C,3H | 5C,8G | 3C,8G | 2C | 6G | 2G | 7H | 0 | 0 | 2G | 5C,7G | 2C | 5G |
| 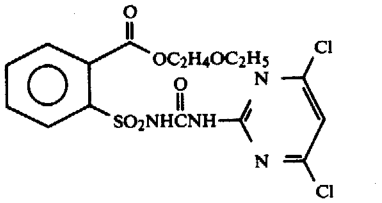 | 0.4 | 3C,5G, 6Y | 1C | 0 | 5C | 0 | 0 | 2C | 2C,6G | 1C | 2G | 1C,7G | 1C,5G | 2C,4G | 2C,7G |

TABLE XII-continued
| | | | | | | | | | | | | | | | |
|---|---|---|---|---|---|---|---|---|---|---|---|---|---|---|---|
| 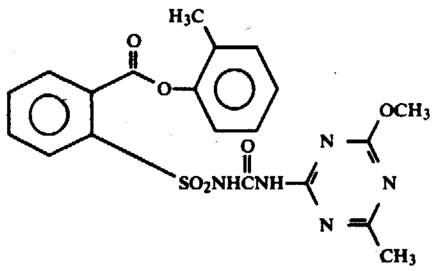 | 0.4 | 9C | 9C | 10C | 9C | 9C | 2C,8G | 2C,8G | 5C,9H | 1C,8G | 1C,7G | 10C | 2C,8G | 3C,8G | 2C,8G |
| 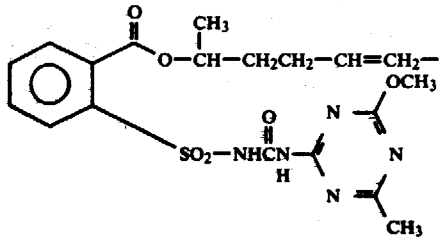 | 0.4 | 9C | 9C | 10C | 10C | 9C | 7G | 9C | 6C,9H | 2C,7G | 2C,6G | 9C | 9C | 5C,8G | 2C,8G |
| 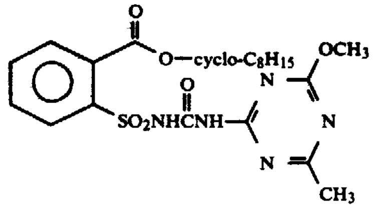 | 0.4 | 9C | 9C | 10C | 9C | 9C | 4G | 1C,5G | 6C,9H | 4G | 2G | 9C | 5C,9G | 5C,9G | 1C,8G |
| 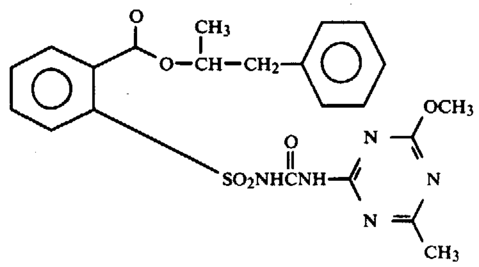 | 0.4 | 9C | 5C,9G | 10C | 9C | 10C | 7G | 9C | 9C | 3C,7G | 3C,6G | 9C | — | — | 5C,9G |

TABLE XII-continued
| | | | | | | | | | | | | | | | |
|---|---|---|---|---|---|---|---|---|---|---|---|---|---|---|---|
| 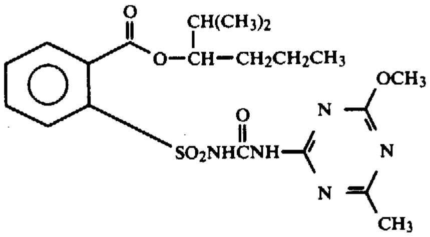 | 0.4 | 9C | 6C,9G | 10C | 10C | 9C | 1C,8G | 3C | 9C | 1C,2G | 1C,4G | 9C | 9C | — | 5C,9G |
| 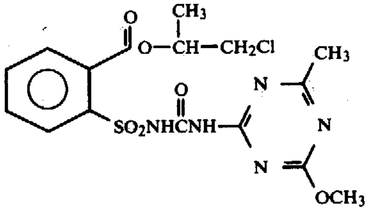 | 0.4 | 9C | 4C,9G | 10C | 9C | 5C,9G | 2C,8G | 2C,6G | 3C,9H | 3G | 2G | 3U,8G | 5C,9G | 3C,7G | 2C,8G |
| 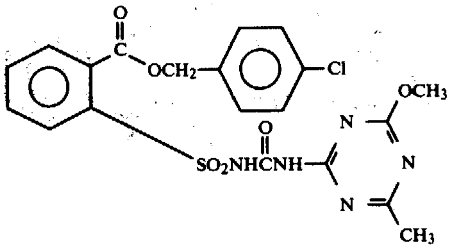 | 0.4 | 5C,8G, 6Y | 5C,9G | 9C | 5C,9G | 5C,9G | 0 | 5C,8G | 3C,7H | 2C | 0 | 8U,9G | 5C,8G | 3C,8G | 2C,9G |
| 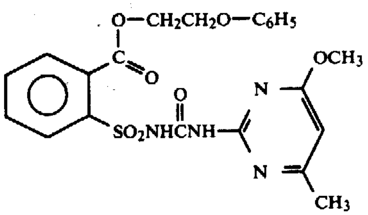 | 0.4 | 9C | 9C | 9C | 10C | 5C,9G | 8G | 4G | 9C | 1C,2G | 1C,2G | 5U,9H | 9C | 3C,8G | 8G |

TABLE XII-continued
| | | | | | | | | | | | | | | | |
|---|---|---|---|---|---|---|---|---|---|---|---|---|---|---|---|
| 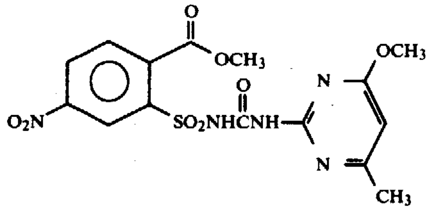 | 0.4 | 9C | 2C,2H, 5G | 9C | 9C | 9C | 9G | 5C,8H | 6C,9H | 4C,8G | 2C,8G | 2C,9H | 2C,8G | 3C,8G | 2U,9G |
| 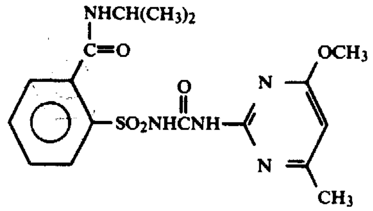 | 0.4 | 6C,9G | 4C,9G | 10C | 9C | 9C | 9C | 10C | 9C | 9C | 6C,8G | 5U,9C | 9C | 5C,9G | 9C |
| 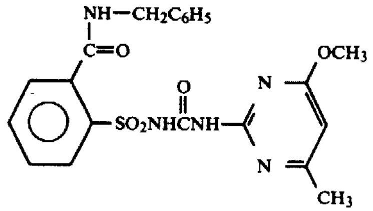 | 0.4 | 9C | 9C | 10C | 9C | 6C,9G | 6C,9G | 4C,8G | 9C | 9C | 9C | 10C | 9C | 6C,8G | 9C |
| 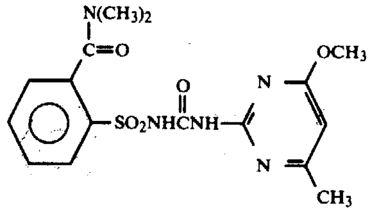 | 0.4 | 10D,9G | 6C,9G | 10C | 5C,9G | 9C | 7C,9G | 5C,8G | 10C | 9C | 9C | 9C | 9C | 9C | 9C |
| 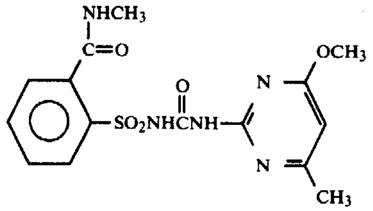 | 0.4 | 9C | 10C | 10C | 9C | 9C | 10C | 9C | 9C | 9C | 9C | 10C | 9C | 5C,9G | 10C |

TABLE XII-continued
| | | | | | | | | | | | | | | | |
|---|---|---|---|---|---|---|---|---|---|---|---|---|---|---|---|
| 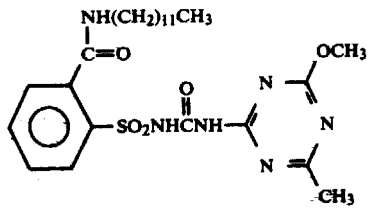 | 0.4 | 8C,9G | 6C,9G | 9C | 2H,8G | 5C,9G | 9G | 2C,6G | 4C,9H | 2C,6G | 3C,5G | 5U,9G | 9C | 5C,9G | 3C,9H |
| 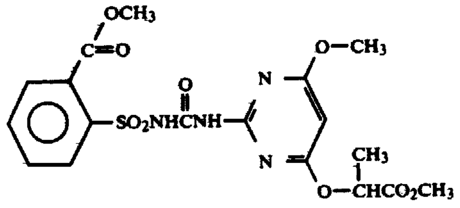 | 0.4 | 9C | 6C,9G | 9C | 5C,9G | 9C | 9C | 9C | 9C | 9C | 9C | 9C | 9C | 9C | 9C |
| 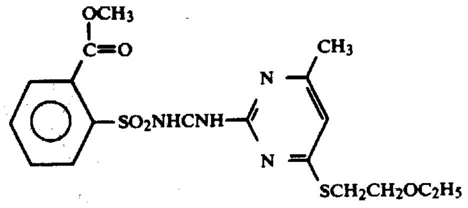 | 0.4 | 9C | 2C,3H, 8G | 2C,8G | 2C | 1C,6H | 8G | 1C,5G | 5C,9H | 1C,7G | 6G | 9H | 1C,5H | 8G | 9G |
| 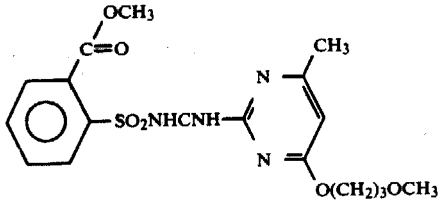 | 0.4 | 9C | 2C,3H, 9G | 5C,9G | 3C,8G | 9C | 9C | 9C | 9C | 6C,9G | 5C,8G | 9C | 8C | 8C | 9C |

TABLE XII-continued
| | | | | | | | | | | | | | | | |
|---|---|---|---|---|---|---|---|---|---|---|---|---|---|---|---|
| 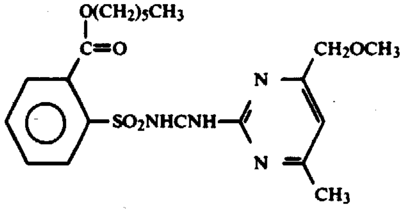 | 0.4 | 4C,7G, 6G | 2C | 2C | 2C,5G | 1C | 1C,5G | 0 | 3C | 0 | 0 | 1C,7H | 2C | 2C,7G | 1C,5G |
| 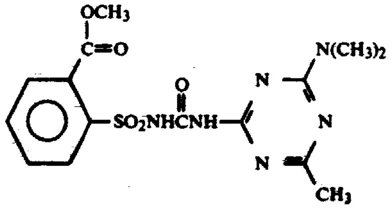 | 0.4 | 9C | 9C | 10C | 9C | 9C | 8G | 3C,9G | 10C | 9C | 9C | 9C | 9C | 10C | 10C |
| 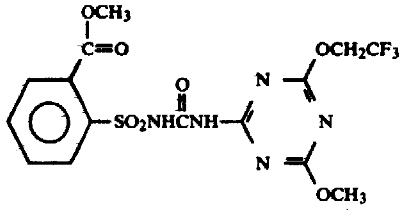 | 0.4 | 9C | 9C | 10C | 10C | 10C | 5C,9G | 3G | 6C,9H | 3C,7G | 2C,6G | 10C | 6C,9G | — | 2C,9G |
| 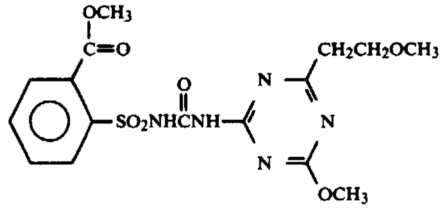 | 0.4 | 9C | 9C | 10C | 2C,8G | 3C,8G | 1C,8G | 9C | 5C,8H | 1C,5G | 1C | 9C | 9C | 5C,9G | 3C,9G |
| 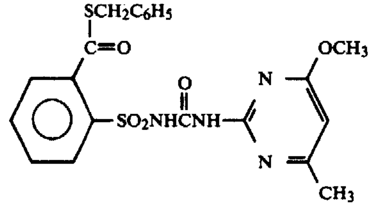 | 0.4 | 9C | 9C | 10C | 9C | 9C | 2C,9G | 1C,8G | 9C | 4C,7G | 4C,6G | 9C | 8C | 5C,9G | 3C,9G |

TABLE XII-continued
| | | | | | | | | | | | | | | | |
|---|---|---|---|---|---|---|---|---|---|---|---|---|---|---|---|
| 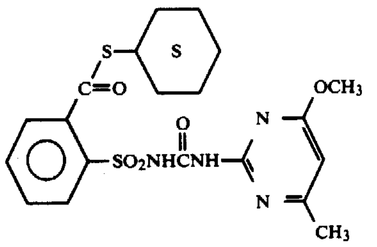 | 0.4 | 9C | 9C | 10C | 9C | 9C | 10C | 5C,8G | 9C | 9C | 5C,8G | 7U,9C | 6C,9G | 9C | 9C |
| 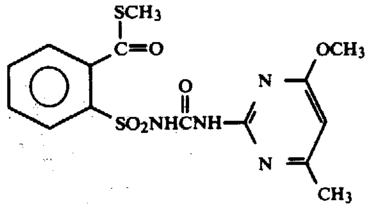 | 0.4 | 9C | 9C | 9C | 9C | 9C | 2C,8G | 2C,7G | 9C | 3C,7H | 1C,5H | 9C | 9C | 5C,8G | 9C |
| 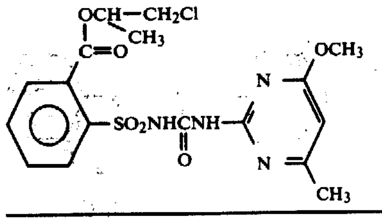 | 0.4 | 6C,9G | 9C | 10C | 9C | 10C | 9C | 9C | 10C | 8C | 8C | 9C | 5C,9G | 6C,9G | 9C |
| | PRE EMERGENCE | | | | | | | | | | | | | |
|---|---|---|---|---|---|---|---|---|---|---|---|---|---|---|
| | kg/ha | MORNING-GLORY | COCK-LEBUR | CASSIA | NUTS-EDGE | CRAB-GRASS | BARNYARD-GRASS | WILD OATS | WHEAT | CORN | SOYBEAN | RICE | SOR-GHUM |
| 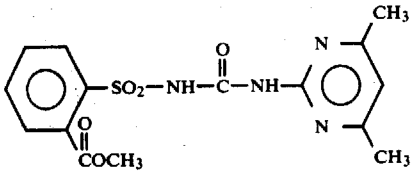 | 0.4 | 9G | 9G | 8G | 10E | 9G | 9H | 3C 9H | 9H | 10E | 9H | 10E | 10E |
| | 2.0 | 9G | 9G | 9G | 10E | 9G | 9H | 3C 9H | 9H | 10E | 9H | 10E | 10E |

TABLE XII-continued
| | | | | | | | | | | | | | | |
|---|---|---|---|---|---|---|---|---|---|---|---|---|---|---|
| 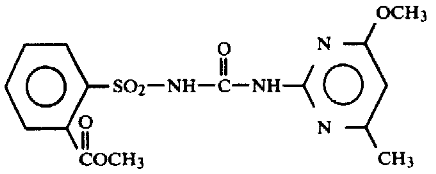 | 0.4 | 9G | 9G | 9G | 10E | 9H | 9H | 9H | 9H | 10H | 9H | 10E | 9H |
| 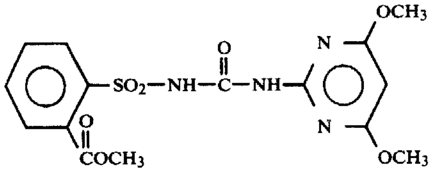 | 0.4 | 9G | 9G | 9G | 10E | 9H | 9H | 9H | 9H | 9H | 10E | 10E | 9H |
| 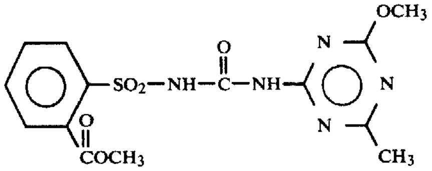 | 0.4 | 9H | 9G | 9G | 10E | 10E | 9H | 9H | 9H | 10E | 9H | 10E | 9H |
| 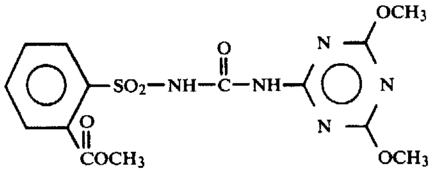 | 0.4 | 9G | 9G | 9G | 9G | 9H | 9H | 9G | 9G | 9G | 9H | 10E | 9G |
| 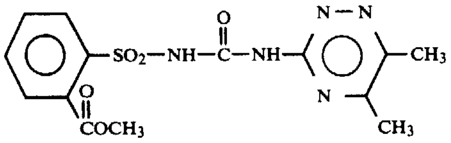 | 2 | 9C | 9G | 9C | 10E | 4C 9G | 9H | 9H | 9H | 9G | 9H | 10E | 9H |
| 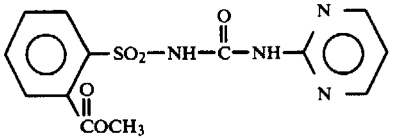 | 2 | 5C 9G | 9G | 9G | 10E | 2C 8G | 2C 9H | 8G | 8G | 9G | 2C 8H | 10E | 9G |

TABLE XII-continued
| | | | | | | | | | | | | | |
|---|---|---|---|---|---|---|---|---|---|---|---|---|---|
| 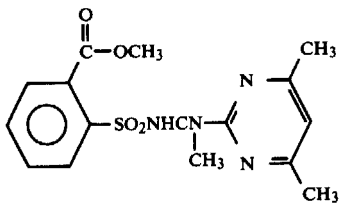 | 0.4 | 0 | — | 0 | 0 | 3G | 2G | 0 | 4H | 3G | 0 | 8H | 4G |
| 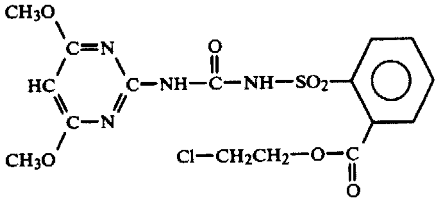 | 0.4 | 9G | 9G | 4C,8G | 10E | 2C,5G | 9H | 9G | 9G | 2U,9G | 9H | 10E | 9H |
| 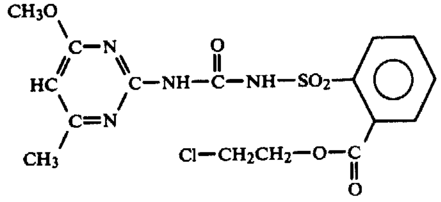 | 0.4 | 9C | 9G | 9C | 10E | 2C,6G | 10H | 5C,9H | 9H | 10H | 9H | 10E | 10H |
| 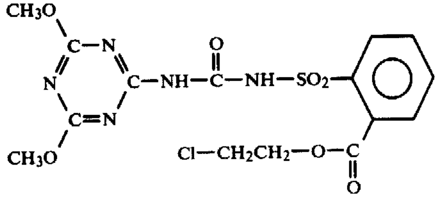 | 0.4 | 9C | 9G | 5C,9G | 10E | 4G | 2C,9G | 8G | 5G | 9G | 9H | 9H | 9G |

TABLE XII-continued
| | | | | | | | | | | | | | | |
|---|---|---|---|---|---|---|---|---|---|---|---|---|---|---|
| 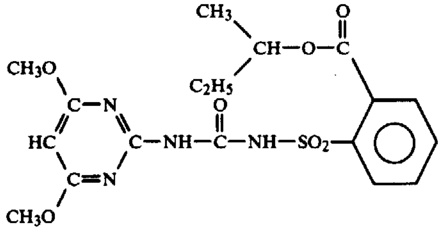 | 0.4 | 9G | 9G | 8G | 10E | 0 | 9H | 8G | 2G | 2C,8G | 8H | 10E | 9G |
| 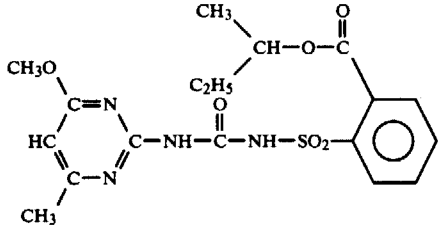 | 0.4 | 9G | 10E | 9G | 10E | 6G | 9H | 2C,9H | 9G | 2U,9H | 9H | 10E | 9H |
| 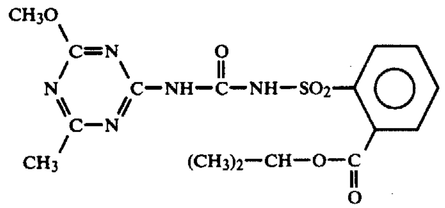 | 0.4 | 9G | 9G | 6C,9G | 10E | 2C,6G | 2C,9H | 9G | 5G | 9G | 9H | 10E | 2C,9G |
| 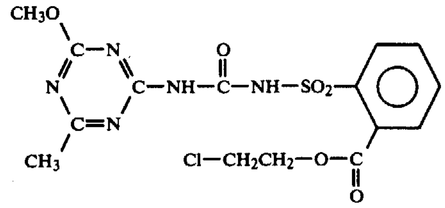 | 0.4 | 9C | 9G | 6C,9G | 9G | 1C,3G | 4C,9G | 8H | 1C,2G | 3C,9G | 9H | 9H | 2C,9G |

TABLE XII-continued
| | | | | | | | | | | | | | | |
|---|---|---|---|---|---|---|---|---|---|---|---|---|---|---|
| 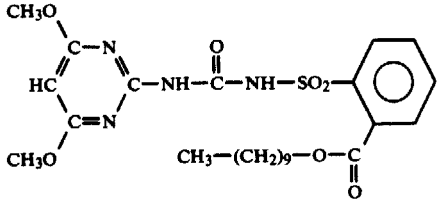 | 0.4 | 5G | 9G | 5G | 5G | 0 | 2C,8G | 6G | 2G | 2C,7G | 3G | 8G | 8G |
| 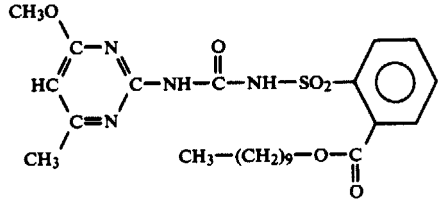 | 0.4 | 8G | 9G | 7G | 7G | 0 | 2C,9G | 2C,8G | 8G | 2C,8G | 1C,3G | 9H | 2H,8G |
| 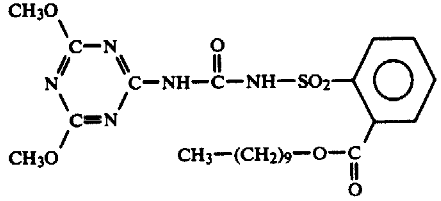 | 0.4 | 4G | 5C,9G | 2C,5G | 0 | 0 | 0 | 0 | 0 | 2G | 1C | 0 | 2H |
| 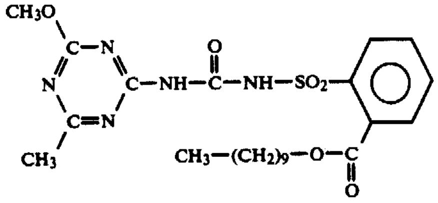 | 0.4 | 0 | 5C,9G | 3C,7G | 2G | 2G | 0 | 0 | 0 | 4G | 0 | 0 | 3G |

TABLE XII-continued
| | | | | | | | | | | | | | | |
|---|---|---|---|---|---|---|---|---|---|---|---|---|---|---|
| 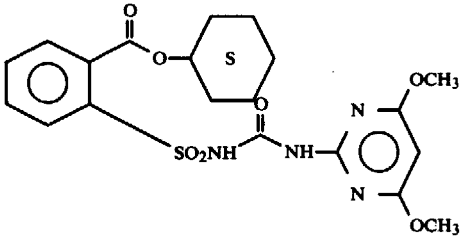 | 0.4 | 8G | 8G | 3G | 5G | 0 | 9H | 5G | 3G | 1C,7G | 2C,4H | 9H | 8G |
| 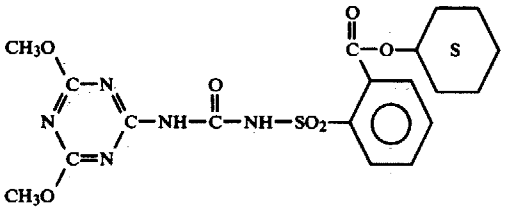 | 0.4 | 9G | 9C | 2C | 0 | 0 | 9H | 2G | 2G | 1C,7G | 2C | 5G | 8G |
| 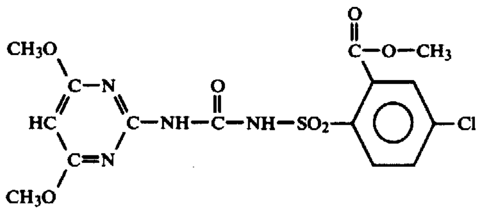 | 0.4 | 9G | 9G | 2C,9G | 10E | 5G | 9H | 9G | 3G | 9H | 9H | 10E | 9H |
| 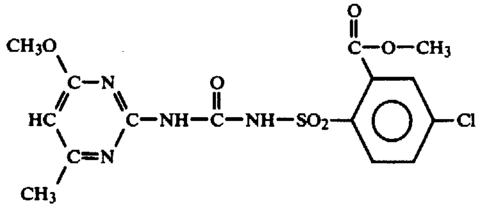 | 0.4 | 9G | 9H | 3C,9G | 10E | 2C,5G | 9H | 9G | 8H | 2U,9G | 9H | 10E | 9H |

TABLE XII-continued
| | | | | | | | | | | | | | |
|---|---|---|---|---|---|---|---|---|---|---|---|---|---|
| 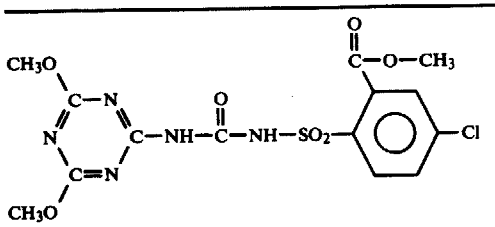 | 0.4 | 9G | 9G | 5C,9G | 10E | 1C | 2C,8H | 8G | 1C | 2C,9H | 9H | 10E | 9H |
| 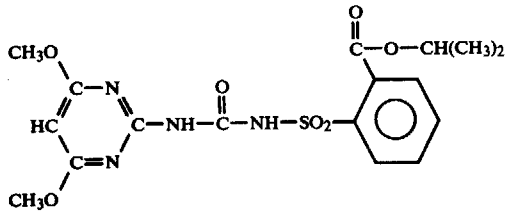 | 0.4 | 9G | 5H,9G | 5H,8G | 10E | 8G | 5H,9G | 7G | 7G | 5H,9G | 6H,8G | 10E | 5H,9G |
| 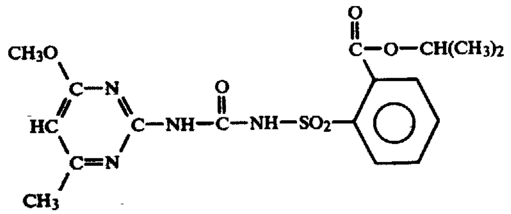 | 0.4 | 9H | 8H,9G | 8H,9G | 10E | 8G | 5H,9G | 8G | 9G | 7H,9G | 8H,9G | 10E | 8H,9G |
| 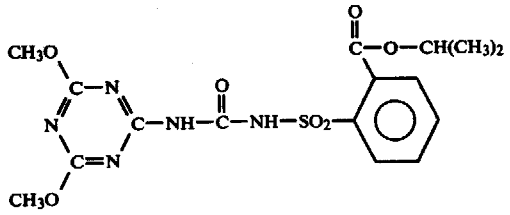 | 0.4 | 8H,9G | 8H,9G | 8H,8G | 9E,9G | 7G | 5H,9G | 8G | 7G | 7H,9G | 7H,8G | 7E,8G | 7H,9G |
| 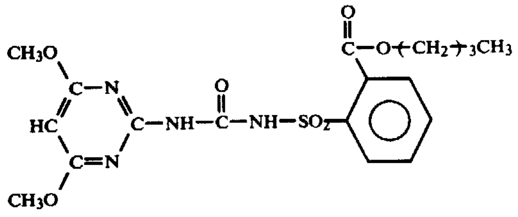 | 2<br>0.4 | 5C,9G<br>9G | 9G<br>9G | 9C<br>9G | 10E<br>10E | 7G<br>8G | 9H<br>9H | 8G<br>7G | 9G<br>9G | 9G<br>2C,9G | 9H<br>7H | 10E<br>10E | 9H<br>9H |

TABLE XII-continued
| | | | | | | | | | | | | | | | |
|---|---|---|---|---|---|---|---|---|---|---|---|---|---|---|---|
| 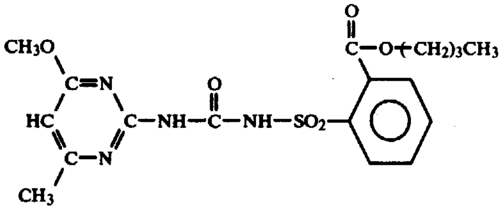 | 2 | 5C,9H | 9G | 3C,9G | 10E | 3C,9G | 9H | 3C,9G | 9H | 9G | 9H | 10E | 9H |
| | 0.4 | 9G | 9G | 9G | 10E | 7G | 9H | 2C,8G | 9H | 9G | 9H | 10E | 9H |
| 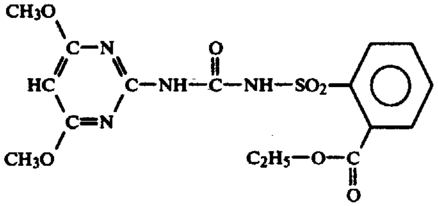 | 2 | 10E | 9G | 9G | 10E | 9H | 9H | 2C,9G | 9H | 10E | 9H | 10E | 10H |
| 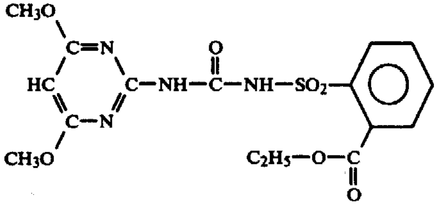 | 0.4 | 10E | 9G | 9G | 10E | 3C,9G | 9H | 9G | 9H | 10E | 9H | 10E | 9H |
| 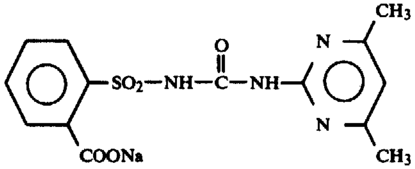 | 2 | 7G | 5H,8G | 5H,8G | 10E | 2G | 5H,8G | 5H,7G | 5H,8G | 5H,9G | 5H,8G | 8H,9G | 5H,8G |
| | 2 | 1C | 1C | 1C | 0 | 0 | 0 | 0 | 0 | 3G | 1C | 0 | 0 |
| 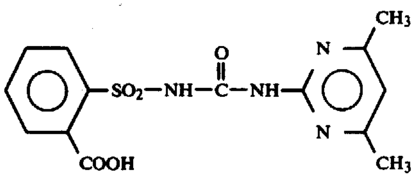 | 10 | 7G | 9G | 1C,5G | 9G | 1C | 1C,3G | 1C,5G | 2C,7G | 8G | 4G | 2C,7G | 5G |
| | 2 | 1C | 0 | 1C | 9G | 0 | 0 | 0 | 3G | 3G | 0 | 0 | 0 |
| | 2 | 0 | 0 | 0 | 0 | 0 | 0 | 0 | 0 | 0 | 0 | 0 | 0 |
| | 0.4 | 0 | 0 | 0 | 0 | 0 | 0 | 0 | 0 | 0 | 0 | 0 | 0 |

TABLE XII-continued
| | | | | | | | | | | | | | |
|---|---|---|---|---|---|---|---|---|---|---|---|---|---|
| 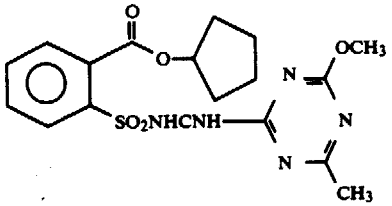 | 0.4 | 9G | 9G | 8G | 9G | 6G | 9H | 4G | 4G | 2C,7G | 9H | 9H | 1C,9G |
| 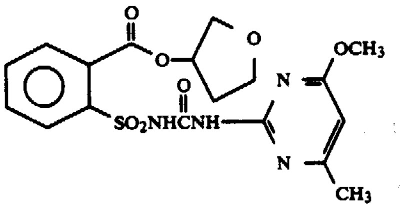 | 0.4 | 9G | 9G | 9G | 10E | 4C,9G | 9H | 2C,8G | 9H | 10E | 9H | 10E | 10E |
| 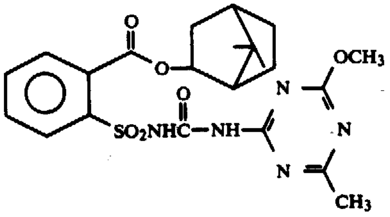 | 0.4 | 8G | 9G | 9G | 2G | 5G | 5G | 2G | 0 | 2C,7G | 2C,4H | 2C,5G | 8G |
| 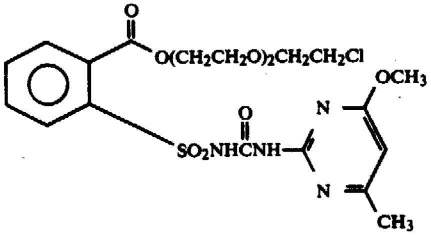 | 0.4 | 9G | 9G | 9C | 10E | 2C,9G | 9H | 1C,8G | 1C,9H | 2C,9H | 9H | 10E | 2C,9H |

TABLE XII-continued
| | | | | | | | | | | | | | |
|---|---|---|---|---|---|---|---|---|---|---|---|---|---|
| 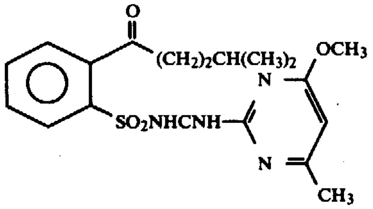 | 0.4 | 9G | 9G | 9G | 9G | 2C,9G | 5C,9H | 2C,8H | 9G | 9G | 8H | 10E | 9H |
| 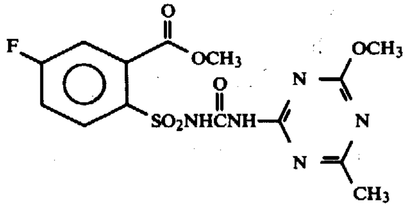 | 0.4 | 9G | 10E | 9G | 10E | 5G | 2C,8G | 2G | 0 | — | 9H | 9H | 9G |
| 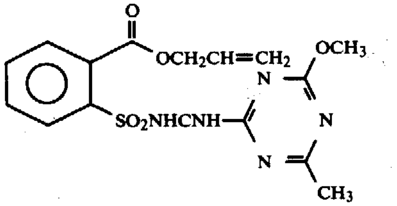 | 0.4 | 9G | 9G | 9G | 10E | 9H | 9H | 3C,9G | 9H | 10E | 9H | 10E | 10H |
| 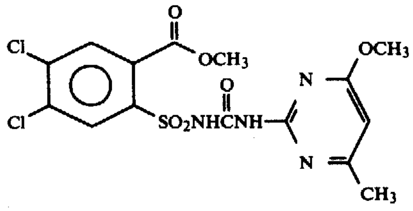 | 0.4 | 8G | 8G | 0 | 10E | 2G | 9G | 4G | 5G | 2C,7G | 1C,5H | 9H | 2C,9G |
| 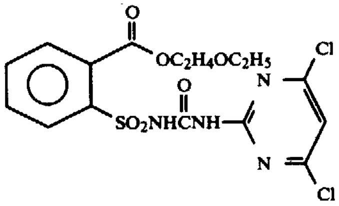 | 0.4 | 3G | — | 0 | 10E | 2G | 1C,8H | 0 | 0 | 1C | 0 | 8H | 8G |

TABLE XII-continued
| | | | | | | | | | | | | |
|---|---|---|---|---|---|---|---|---|---|---|---|---|
| 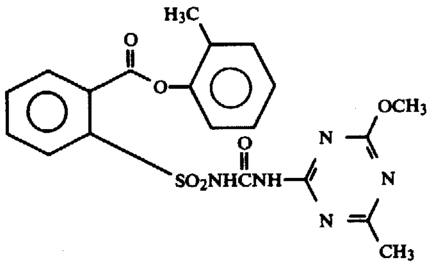 | 0.4 | 9G | 9G | 9G | 8G | 2C,9G | 9H | 1C,7G | 1C,5G | 1C,9G | 9H | 10E | 2C,9G |
| 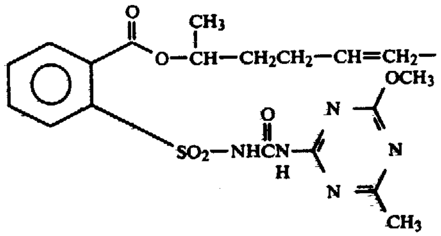 | 0.4 | 9G | 9G | 9G | 9G | 1C,8G | 2C,9H | 1C,8G | 7G | 2C,9G | 9H | 10E | 9H |
| 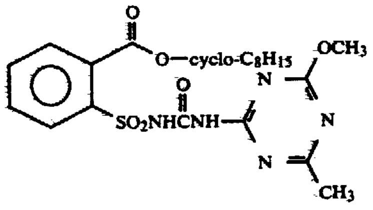 | 0.4 | 3C,9G | 9G | 8G | 7G | 5G | 9H | 7G | 5G | 1U,9G | 9H | 9H | 1C,9G |
| 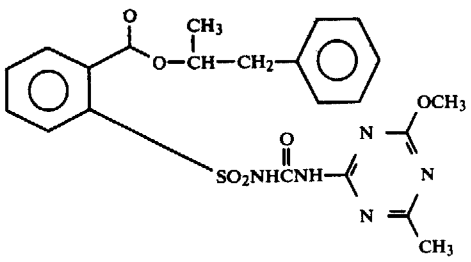 | 0.4 | 9G | 9G | 10E | 10E | 2C,9G | 9H | 9H | 9H | 9H | 9H | 10E | 9H |

TABLE XII-continued
| | | | | | | | | | | | | | | |
|---|---|---|---|---|---|---|---|---|---|---|---|---|---|---|
| 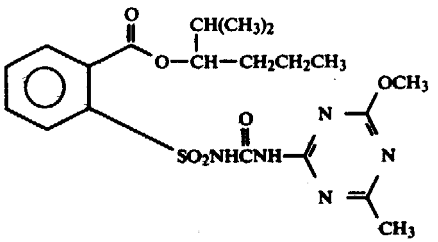 | 0.4 | 9G | 8G | 8G | 5G | 0 | 9H | 5G | 3G | 8G | 9H | 9H | 2C,9G |
| 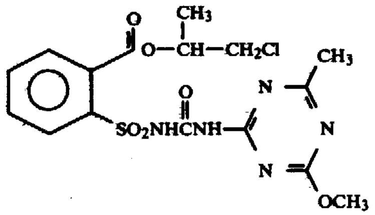 | 0.4 | 9G | 9G | 8G | 2C,9G | 2C,8G | 2C,9H | 2C,8G | 4G | 9G | 9H | 9H | 9H |
| 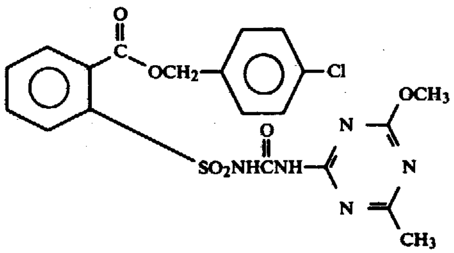 | 0.4 | 9G | 8G | 8G | 9G | 2C,8H | 2C,9H | 4G | 0 | 2C,8G | 7H | 9H | 1C,9G |
| 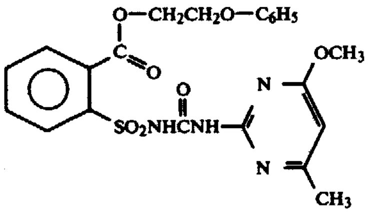 | 0.4 | 9C | 9G | 3C,8G | 10E | 2C,8G | 5C,9H | 1C,8G | 9H | 9G | 9H | 10E | 5C,9H |

TABLE XII-continued
| | | | | | | | | | | | | | |
|---|---|---|---|---|---|---|---|---|---|---|---|---|---|
| 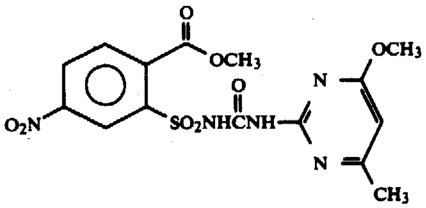 | 0.4 | 9G | 9G | 9G | 1C,9G | 2C,9G | 6C,9H | 2C,8G | 9G | 2C,8G | 9H | 9H | 4C,9H |
| 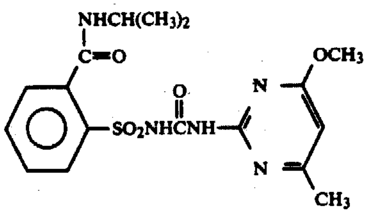 | 0.4 | 9G | 8G | 9G | 10E | 9H | 9H | 2C,8G | 9H | 9H | 9H | 10E | 9H |
| 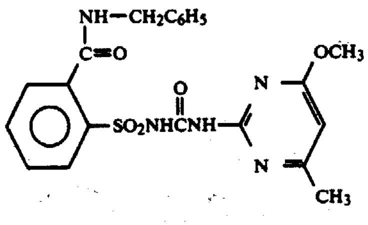 | 0.4 | 9G | 8G | 9G | 10E | 3C,9G | 9H | 3C | 9H | 1C,9G | 9H | 10E | 5C,9H |
| 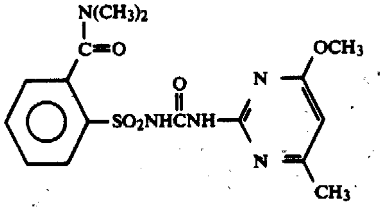 | 0.4 | 9G | 9G | 9G | 10E | 2C,9G | 9H | 2C,9G | 9H | 9H | 9H | 10E | 9H |
| 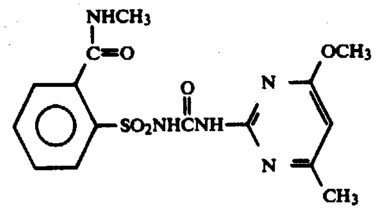 | 0.4 | 10E | 9G | 9G | 10E | 1C,9G | 1C,9H | 2C,9H | 9H | 10E | 9H | 10E | 10E |

TABLE XII-continued
| | | | | | | | | | | | | | |
|---|---|---|---|---|---|---|---|---|---|---|---|---|---|
| 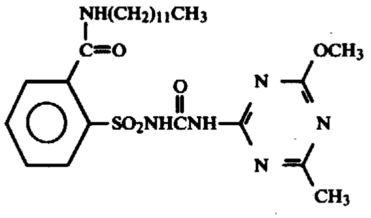 | 0.4 | 9G | 8G | 8G | 10E | 2C,5H | 9H | 6G | 6G | 8G | 2C,5H | 9H | 1C,9G |
| 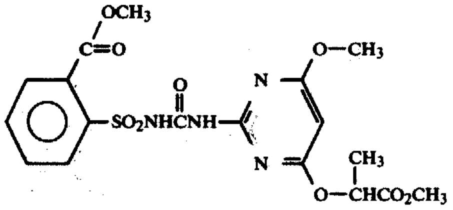 | 0.4 | 10E | 10E | 3C,9G | 10E | 5C,9G | 5C,9H | 5C,9H | 10E | 10H | 9H | 10E | 10H |
| 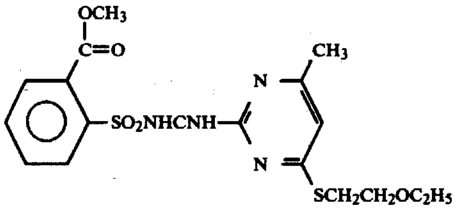 | 0.4 | 9G | 10E | 2C,8G | 10E | 2C,8G | 3C,9H | 1C,5G | 2C,9H | 9G | 9H | 10E | 9H |
| 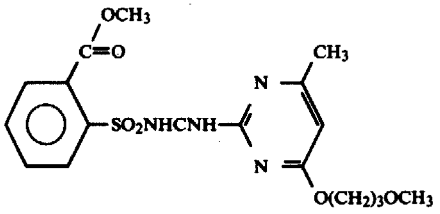 | 0.4 | 10E | 9G | 8G | 10E | 5C,9G | 7C,9H | 4C,6G | 9H | 9H | 9H | 10E | 9H |

TABLE XII-continued
| | | | | | | | | | | | | | | |
|---|---|---|---|---|---|---|---|---|---|---|---|---|---|---|
| 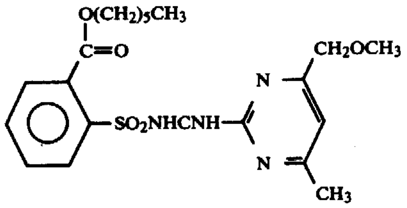 | 0.4 | 0 | 0 | 0 | 10E | 0 | 2G | 0 | 0 | 1C,4G | 0 | 8H | 3G |
| 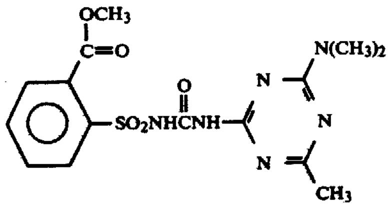 | 0.4 | 9G | 9G | 8G | 10E | 2C,9G | 2C,9H | 2C,7G | 9H | 9G | 9H | 10E | 9H |
| 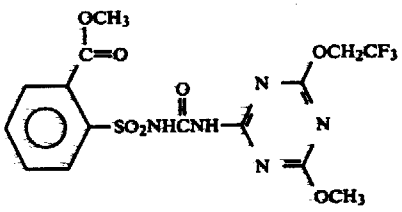 | 0.4 | 9G | 9G | 9G | 10E | 2G | 2C,9H | 1C,7G | 6G | 2U,9G | 9H | 10E | 2C,9G |
| 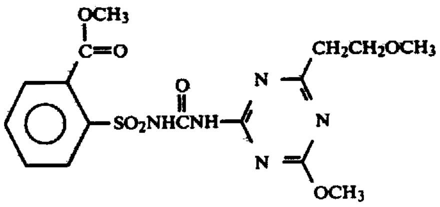 | 0.4 | 9G | 9G | 2C,8G | 1C,9G | 1C,5G | 2C,9H | 2C,8G | 6G | 10H | 9H | 10E | 9H |
| 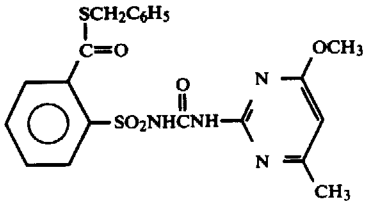 | 0.4 | 9G | 8G | 9G | 10E | 2C,9G | 4C,9H | 2C,7G | 9H | 9G | 9H | 10E | 9H |

TABLE XII-continued
| | | | | | | | | | | | | | |
|---|---|---|---|---|---|---|---|---|---|---|---|---|---|
| 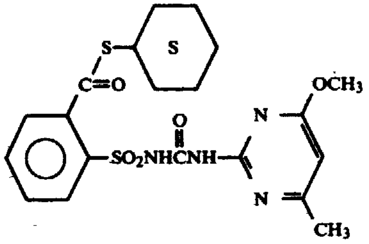 | 0.4 | 9H | 9G | 9G | 10E | 5C,9G | 9H | 4C,9G | 9H | 9G | 9H | 10E | 9H |
| 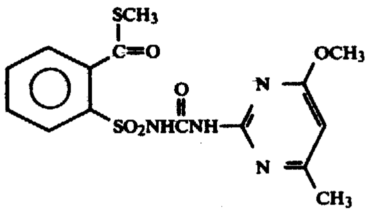 | 0.4 | 9G | 9G | 9G | 2C,8G | 2C,9G | 2C,9H | 2C,8G | 1C,6G | 1U,9G | 9H | 10E | 9H |
| 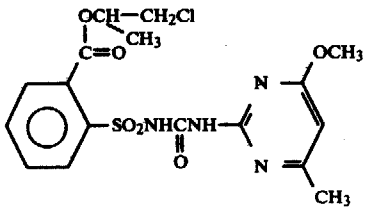 | 0.4 | 9G | 9G | 9G | 10E | 1C,9G | 6C,9H | 5C,8G | 9H | 9H | 9H | 10E | 5C,9H |

Test B

Two bulb pans were filled with fertilized and limed Fallsington silt loam soil. One pan was planted with seeds of corn, sorghum, Kentucky bluegrass and several grassy weeds. The other pan was planted with seeds of soybeans, purple nutsedge tubers (*Cyperus rotundus*), and seeds of several broadleaf weeds. Seeds of the following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), dallisgrass (*Paspalum dilatatum*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A smaller pot was also filled with prepared soil and planted with rice and wheat seeds. Another small pot was planted with seeds of sugarbeets. The above four containers were treated preemergence with nonphytotoxic solvent solutions of the compounds of this invention (i.e., solutions of said compound were sprayed on the soil surface before seed germination). Duplicates of the abovedescribed seeded containers were prepared without treatment and used as controls.

Twenty-eight days after treatment, the treated and control plants were evaluated and the data recorded as set forth in Table XIII.

TABLE XIII

Preemergence on Fallsington Silt Loam

| | Rate kg/ha | CRAB-GRASS | BARN-YARD-GRASS | SOR-GHUM | WILD OATS | JOHN-SON-GRASS | DAL-LIS-GRASS | GIANT FOXTAIL | KY. BLUE-GRASS | CHEAT-GRASS | SUGAR-BEETS | CORN | MUS-TARD |
|---|---|---|---|---|---|---|---|---|---|---|---|---|---|
| 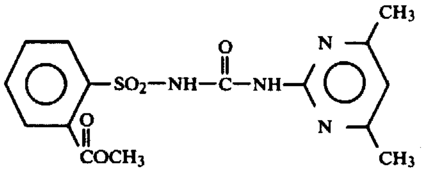 | 1/128 | 9G 9C | 10C | 10C | 8G 8C | 10C | 8G 8C | 9G 9C | 10C | 10C | 8G 5H | 10C | 10C |
| | 1/64 | 10C | 10C | 10C | 10C | 10C | 10C | 10C | 10E | 10C | 10C | 10C | 10C |
| | 1/32 | 10C | 10C | 10C | 10C | 10C | 10C | 10C | 10E | 10C | 10C | 10C | 10C |
| | 1/16 | 10C | 10C | 10E | 7G 5C | 10C | 10C | 10C | 10C | 10C | 10C | 10E | 10C |
| | 1/4 | 10C | 10C | 10E | 8G 8C | 10C | 10C | 10C | 10C | 10C | 10C | 10E | 10C |
| 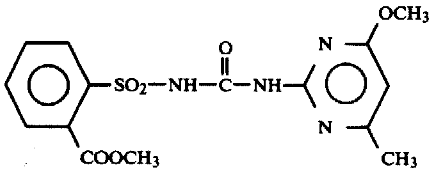 | 1/64 | 8G 3C | 10C | 10C | 8G 8C | 10C | 10C | 10C | 10C | 10C | 10C | 10C | 10C |
| | 1/32 | 9G 9C | 10C | 10C | 10C | 10C | 10C | 10C | 10E | 10C | 10C | 10C | 10C |
| | 1/16 | 10C | 10C | 10C | 9G 9C | 10C | 10C | 10C | 10E | 10C | 10C | 10C | 10C |
| 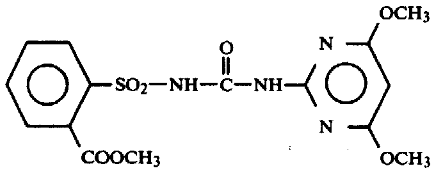 | 1/64 | 8G 5C | 10C | 9G 9C | 5G | 9G 9C | 5G | 8G | 10C | 10C | 10C | 7G 3C | 10C |
| | 1/32 | 8G 5C | 10C | 10C | 7G 5C | 10C | 7G | 9G 9C | 10E | 10C | 10C | 7G 5C | 10C |
| | 1/16 | 10C | 10C | 10C | 6G 5C | 10C | 8G 8C | 10C | 10E | 10C | 10C | 10C | 10C |
| 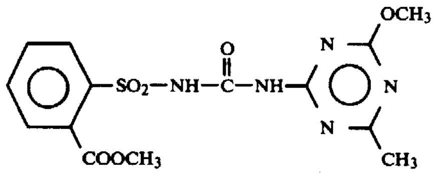 | 1/64 | 7G 3C | 9G 9C | 10C | 4G | 7G 7C | 0 | 7G 3C | 10C | 7G | 10C | 7G 5C | 10C |
| | 1/32 | 9G 9C | 10C | 10C | 5G 3C | 8G 8C | 4G 3C | 8G 5C | 10E | 8G 8C | 10C | 10C | 10C |
| | 1/16 | 10C | 10C | 10C | 10C | 10C | 6G | 10C | 10E | 10C | 10C | 10C | 10C |
| 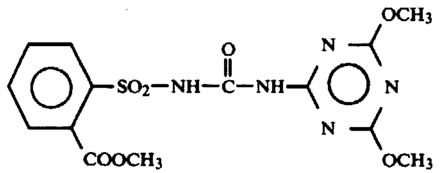 | 1/64 | 7G | 3G | 7G | 0 | 6G | 0 | 6G 3C | 7G 3C | 3G | 10C | 6G 5H | 10C |
| | 1/32 | 8G 5C | 7G 7C | 9G 8C | 10C | 7G 7C | 0 | 5G 3C | 8G 5C | 3G | 10C | 7G 5C | 10C |
| | 1/16 | 10C | 9G 9C | 10C | 5G 3C | 8G 8C | 3G | 8G 8C | 10C | 6G 3C | 10C | 10C | 10C |

TABLE XIII-continued
| Preemergence on Fallsington Silt Loam | | | | | | | | | | | | | | |
|---|---|---|---|---|---|---|---|---|---|---|---|---|---|---|
| 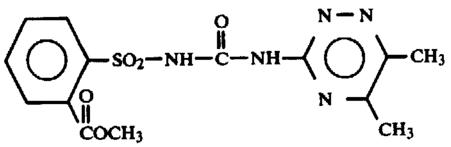 | 1/16 | 0 | 10C | 10C | 0 | 10C | 5G | 3G | 8G | 10E | 7G | 4G | 10E |
| | 1/4 | 5G | 10C | 10C | 5G | 10C | 8G, 3C | 6G | 10E | 10E | 10C | 8G, 8C | 10E |
| 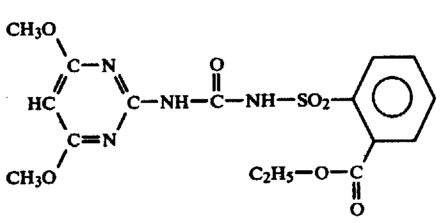 | 1/32 | 0 | 10C | 10C | 8G, 7C | 9G, 9C | 0 | 4G, 3H | 10E | 8G, 9C | 10C | 8G, 8C | 10C |
| | 1/16 | 4G | 10C | 10C | 8G, 8C | 10C | 0 | 5G, 5H | 10E | 10E | 10C | 10C | 10C |
| | 1/4 | 7G | 10C | 10C | 10C | 10C | 6G | 9G, 9C | 10E | 10E | 10C | 10C | 10C |
| 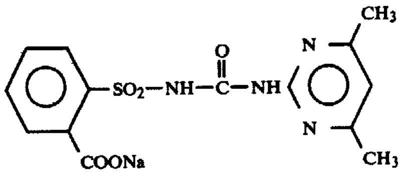 | 1/32 | 0 | 0 | 0 | 0 | 0 | 0 | 0 | 0 | 0 | 6G, 3H | 0 | 0 |
| | 1/16 | 0 | 0 | 0 | 0 | 0 | 0 | 0 | 0 | 0 | 10C | 0 | 0 |
| | 1/4 | 0 | 0 | 0 | 0 | 0 | 0 | 0 | 0 | 6G | 7G, 5H | 0 | 5G |
| 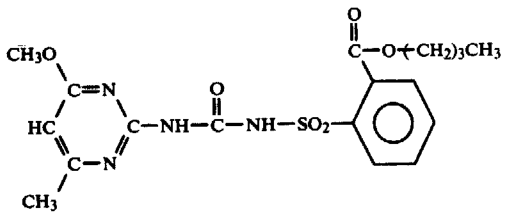 | 1/32 | 0 | 7G, 3C | 6G, 3H | 0 | 0 | 4G | 3H | 9G | 0 | 4G | 0 | 9G |
| | 1/16 | 0 | 8G, 3C | 5G | 0 | 0 | 5G | 3H | 10E | 2G | 4G | 4G | 9G, 5C |
| | 1/4 | 4G | 10C | 10C | 6G, 3C | 5G, 5H | 10E | 10H | 10E | 8G, 8C | 7G, 7C | 5G, 5H | 10C |
| 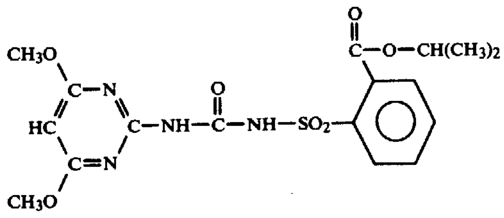 | 1/32 | 0 | 10C | 9G, 9C | 2G | 8G, 8C | 0 | 3H | 10C | 5G | 10C | 6G, 3H | 10C |
| | 1/16 | 0 | 10C | 10C | 6G | 10C | 0 | 4G, 3H | 10C | 8G, 8C | 10C | 7G, 7H | 10C |
| | 1/4 | 6G | 10C | 10C | 7G, 5C | 10C | 5G, 3H | 10C | 10C | 10E | 10C | 10C | 10C |

TABLE XIII-continued
Preemergence on Fallsington Silt Loam
| | | | | | | | | | | | | | | |
|---|---|---|---|---|---|---|---|---|---|---|---|---|---|---|
| 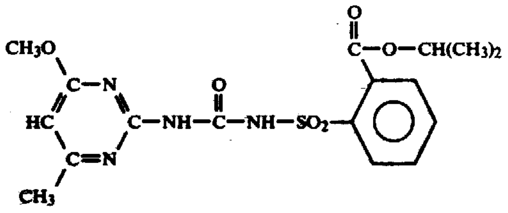 | 1/32 | 0 | 10C | 10C | 4G | 10C | 5G | 6G, 3H | 10C | 10E | 10C | 10C | 10C |
| | 1/16 | 2G | 10C | 10E | 7G, 3C | 10C | 7G | 9G, 9C | 10E | 10E | 10C | 10C | 10C |
| | 1/4 | 7G | 10E | 10E | 10C | 10C | 10C | 10C | 10E | 10E | 10C | 10C | 10C |
| 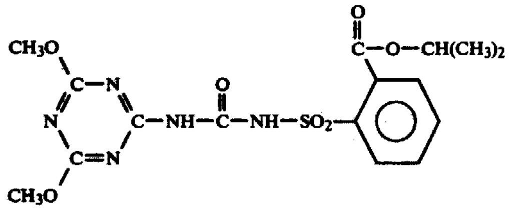 | 1/32 | 0 | 0 | 6G, 3H | 0 | 2H | 0 | 0 | 5G, 6C | 0 | 10C | 7G, 7H | 10C |
| | 1/16 | 4G | 6G, 3H | 7G, 3H | 0 | 2H | 0 | 0 | 7G, 8C | 6G, 3C | 10C | 10C | 10C |
| | 1/4 | 8G | 8C, 5H | 10C | 5G, 3C | 6G, 5H | 4G | 7G | 10E | 7G, 8C | 10C | 10C | 10C |
| 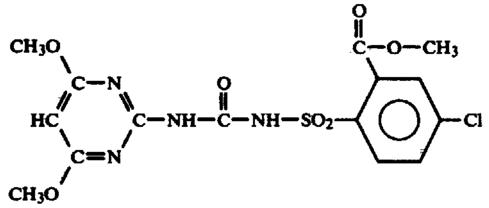 | 1/16 | 3H | 6G, 4C | 10C | 6G | 6G, 3H | 0 | 3H | 8G | 10E | 8G, 8C | 5G, 5H | 10C |
| | 1/4 | 6G | 10C | 10C | 8G, 5C | 8G, 8C | 4G | 6G, 2C | 10E | 10E | 10C | 9G, 9C | 10C |
| 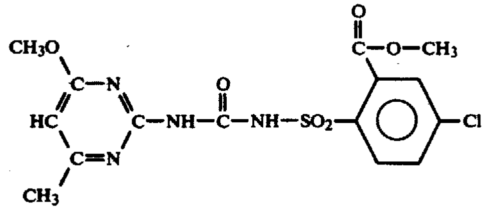 | 1/16 | 0 | 6G, 3H | 10C | 6G | 6G, 3H | 0 | 2H | 9G | 10E | 7G, 8C | 6G, 5H | 10C |
| | 1/4 | 6G | 10C | 10C | 10C | 10C | 5G | 5G, 2C | 10E | 10E | 10C | 9G, 9C | 10C |

TABLE XIII-continued
Preemergence on Fallsington Silt Loam
| | | | | | | | | | | | | | | |
|---|---|---|---|---|---|---|---|---|---|---|---|---|---|---|
| 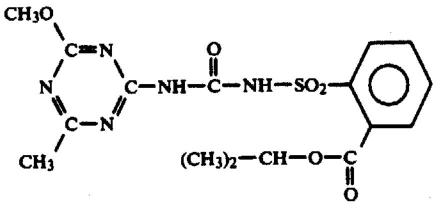 | 1/16 | 6C | 8G, 4C | 9G, 8C | 6G, 2C | 8G, 2C | 3G | 6G | 9G | 7G | 10C | 9G, 9C | 10C |
| | 1/4 | 7G | 8G, 6H | 10C | 8G, 5C | 10C | 5G | 8G, 4C | 10E | 10C | 10C | 10C | 10C |
| 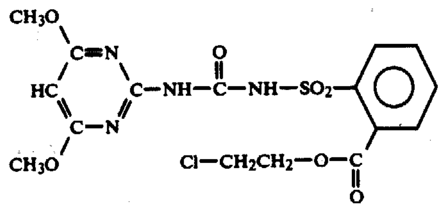 | 1/16 | 0 | 10C | 10C | 8G, 3C | 9G, 3C | 4G | 10C | 10E | 10C | 9G, 9C | 5G, 3H | 10C |
| | 1/4 | 6G | 10C | 10C | 8G, 3C | 10C | 8G, 5C | 10C | 10E | 10E | 9G, 9C | 7G, 7H | 10C |
| 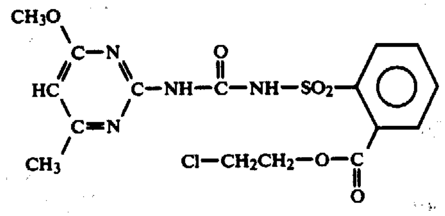 | 1/16 | 0 | 10C | 10C | 8G, 2C | 9G, 9C | 5G | 6G, 4H | 10E | 10E | 9G, 9C | 9G, 9C | 10C |
| | 1/4 | 4G | 10C | 10C | 8G, 6C | 10C | 8G, 9C | 10C | 10E | 10E | 9G, 9C | 9G, 9C | 10C |
| 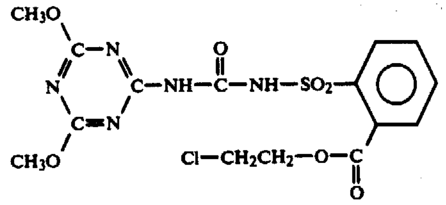 | 1/16 | 0 | 4G | 5G | 3G | 0 | 0 | 0 | 6G | 0 | 10C | 4G, 2H | 9G |
| | 1/4 | 0 | 4G | 7G | 0 | 6G, 6E | 0 | 3H | 8G | 3G | 10C | 7G, 5H | 10C |

TABLE XIII-continued

Preemergence on Fallsington Silt Loam

| | | | | | | | | | | | | | |
|---|---|---|---|---|---|---|---|---|---|---|---|---|---|
| 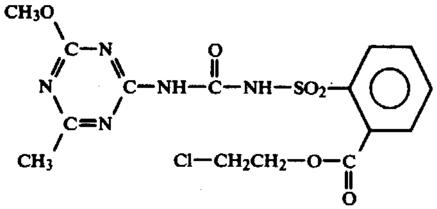 | 1/16 | 0 | 0 | 8G | 3G | 0 | 0 | 0 | 8G | 3G | 9G, 9C | 5G, 3H | 10C |
| | 1/4 | 5G | 7G, 4C | 10C | 6G | 6G | 0 | 6G | 10E | 6G | 10C | 7G, 8H | 10C |

| | Rate kg/ha | COCK-LE-BUR | PIG-WEED | NUT-SEDGE | COT-TON | MORN-ING-GLORY | CAS-SIA | TEA-WEED | VELVET-LEAF | JIM-SON-WEED | SOY-BEAN | RICE | WHEAT |
|---|---|---|---|---|---|---|---|---|---|---|---|---|---|
| 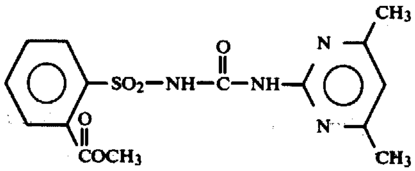 | 1/128 | 7G 5C | — | 10E | 7G | 7G | 8G 8C | — | 10C | 9G 9C | 8G | 10C | 10C |
| | 1/64 | 7G | — | 10E | 8G | 7G | 10C | — | 10C | 9G 9C | 8G 5C | 10C | 10C |
| | 1/32 | 8G | — | 10E | 8G 5C | 8G 6C | 10C | — | 10C | 9G 9C | 10C | 10E | 10C |
| | 1/16 | 8G 5H | 10E | 10E | 10E | 8G | 8G 5C | 10C | 10C | 8G | 8G 8C | 10E | 9G 9H |
| | 1/4 | 8G 8H | 10E | 10E | 10E | 8G 8C | 8G 8C | 10C | 10C | 8G | 8G 8C | 10E | 10H |
| 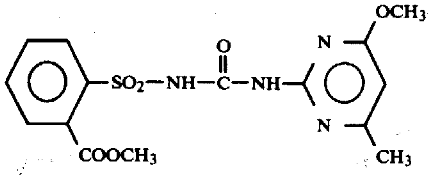 | 1/64 | 8G | — | 10E | 9G 9C | 8G 8C | 10C | — | 10C | 9G 9C | 10C | 10E | 8G 8C |
| | 1/32 | 8G 5C | — | 10E | 10C | 10C | 10C | — | 10C | 10C | 9G 9C | 10E | 10C |
| | 1/16 | 8G 7C | — | 10E | 9G 9C | 10C | 10C | — | 10C | 10C | 8G 5C | 10E | 10C |
| 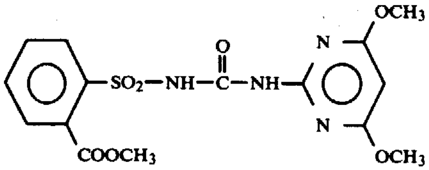 | 1/64 | 7G | — | 10E | 7G | 8G 8C | 10C | — | 10C | 10C | 8G 5C | 10C | 10C |
| | 1/32 | 8G 5C | — | 10E | 7G | 10C | 10C | — | 10C | 8G 8C | 8G 5C | 10C | 8G 8C |
| | 1/16 | 8G 7C | — | 10E | 7G | 9G 9C | 10C | — | 10C | 10C | 8G 5C | 10E | 10C |
| 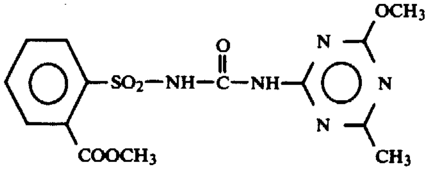 | 1/64 | 8G 9C | — | 7G | 10C | 8G 8C | 10C | — | 10C | 8G 5C | 10C | 8G 8C | 3G |
| | 1/32 | 8G 5C | — | 7G | 8G 5C | 9G 9C | 10C | — | 10C | 9G 8C | 8G 5C | 10C | 4G |
| | 1/16 | 8G 5C | — | 8G | 10C | 10C | 10C | — | 10C | 9G 9C | 8G 8C | 10C | 5G |

TABLE XIII-continued
| Preemergence on Fallsington Silt Loam | | | | | | | | | | | | | |
|---|---|---|---|---|---|---|---|---|---|---|---|---|---|
| 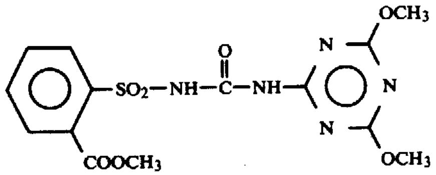 | 1/64 | 8G 3C | — | 7G | 10C | 8G 8C | 10C | — | 7G 8C | 9G 9C | 8G 7C | 6G 5C | 0 |
| | 1/32 | 10C | — | 7G 3C | 8G | 10C | 10C | — | 8G 9C | 10C | 9G 8C | 8G 8C | 2G |
| | 1/16 | 8G 5C | — | 8G | 9G 5C | 10C | 10C | — | 10C | 10C | 8G 5C | 10C | 4G 3C |
| 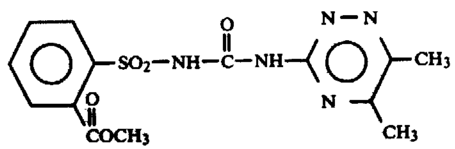 | 1/16 | 7G | 10E | 6G | 4G | 4G | 5G | 0 | 5G | 2G | 7G, 7H | 10E | 2G |
| | 1/4 | 8G | 10E | 10E | 7G | 10E | 7G, 2C | 8G, 5C | 7G | 6G | 8G, 8H | 10E | 8G, 5C |
| 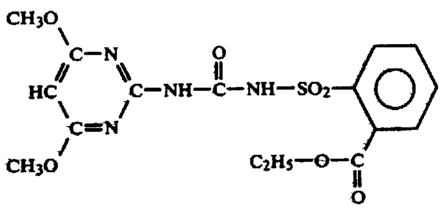 | 1/32 | 7G, 2C | 10E | 10E | 7G | 5G | 7G | 7G | 8G, 7C | 7G | 8G, 3H | 10E | 4G, 2C |
| | 1/16 | 7G, 5H | 10E | 10E | 8G | 7G | 8G, 3C | 7G | 10C | 7G | 7G, 5H | 10E | 6G, 4C |
| | 1/4 | 7G, 5H | 10E | 10E | 8G | 8G | 8G, 8C | 10C | 10C | 8G, 5C | 9G, 9C | 10E | 7G, 4C |
| 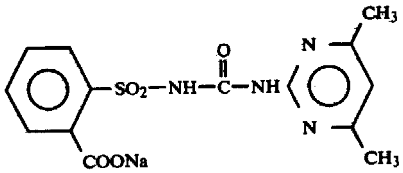 | 1/32 | 0 | 0 | 0 | 0 | 0 | 0 | 0 | 0 | 0 | 0 | 0 | 0 |
| | 1/16 | 0 | 0 | 0 | 0 | 0 | 0 | 0 | 0 | 0 | 0 | 0 | 0 |
| | 1/4 | 0 | 5G | 5G | 0 | 0 | 0 | 0 | 0 | 0 | 0 | 6G, 5C | 0 |
| 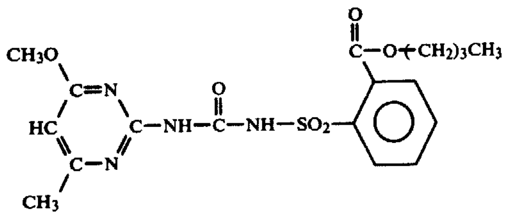 | 1/32 | 3H | 10E | 5G | 0 | 3G | 0 | — | 7G, 7C | 0 | 0 | 9G, 9C | 3G |
| | 1/16 | 2H | 10E | 5G | 0 | 6G | 0 | — | 10C | 2G | 0 | 7G, 5C | 4G |
| | 1/4 | 5G, 5H | 10E | 8G | 3G, 3H | 4G | 3G | 5G, 5H | 10C | 4G | 6G, 6H | 10E | 6G |

TABLE XIII-continued
Preemergence on Fallsington Silt Loam
| | | | | | | | | | | | | | |
|---|---|---|---|---|---|---|---|---|---|---|---|---|---|
| 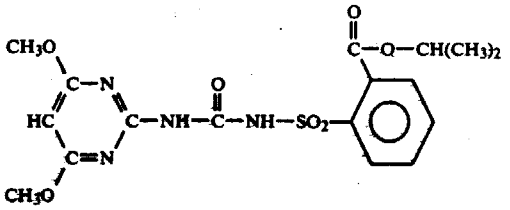 | 1/32 | 7G, 5H | 10E | 10E | 6G | 8G | 8G | 0 | 10C | 8G, 3C | 7G, 5H | 8G, 8C | 2G |
| | 1/16 | 8G, 5H | 10E | 10E | 7G | 8G | 8G, 5H | 6G, 5C | 10C | 8G, 5C | 7G, 5H | 10C | 4G |
| | 1/4 | 8G, 5H | 10E | 10E | 9G | 10C | 10C | 10C | 10C | 8G, 5C | 9G, 5H | 10E | 6G |
| 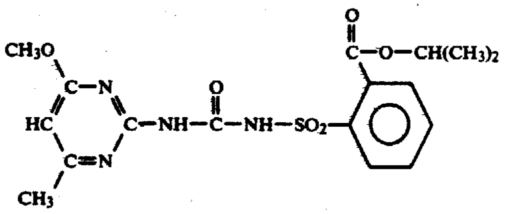 | 1/32 | 8G, 5H | 10E | 10E | 6G, 3H | 9G | 8G, 8C | 10C | 10C | 8G, 5C | 8G, 5H | 8G, 9C | 6G |
| | 1/16 | 8G, 5H | 10E | 10E | 8G, 6C | 9G | 8G, 5C | 10C | 10C | 8G, 7C | 9G, 5H | 10C | 6G, 5C |
| | 1/4 | 8G, 8H | 10E | 10E | 8G, 6C | 10C | 8G, 9C | 10C | 10C | 8G, 8C | 9G, 5H | 10E | 10C |
| 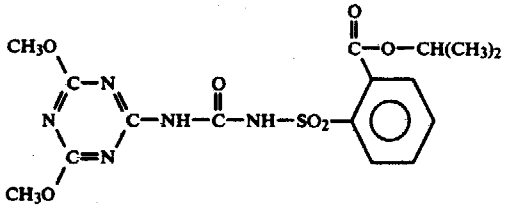 | 1/32 | 8G, 8H | 10E | 10E | 8G | 10C | 8G, 9C | 10C | 10C | 8G, 8C | 9G, 5H | 5G, 3C | 0 |
| | 1/16 | 8G, 8H | 10E | 10E | 8G | 10C | 10C | 10C | 10C | 10C | 9G, 5H | 5G, 3C | 0 |
| | 1/4 | 8G, 8H | 10E | 10E | 10C | 10C | 10C | 10C | 10C | 8G, 9C | 9G, 5H | 7G, 4C | 2G |
| 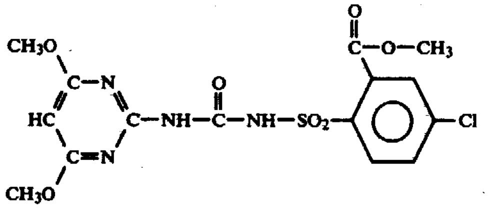 | 1/16 | 8G, 5H | 10C | 10E | 5G | 6G | 4G | 6G, 5C | 8G, 8C | 5G, 3H | 8G, 8C | 10E | 0 |
| | 1/4 | 8G, 3H | 10C | 10E | 5G | 8G, 8C | 8G, 8C | 10C | 10C | 10C | 8G, 8C | 10E | 3G |

TABLE XIII-continued
Preemergence on Fallsington Silt Loam
| | | | | | | | | | | | | | | |
|---|---|---|---|---|---|---|---|---|---|---|---|---|---|---|
| 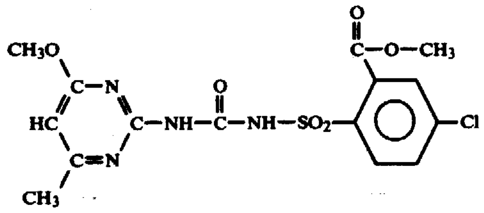 | 1/16 | 6G, 2C | 10C | 10E | 3G | 4G | 3G | 10C | 8G | 8G, 8C | 7G, 5H | 8G, 8C | 3G |
| | 1/4 | 8G, 3C | 10C | 10E | 8G | 10C | 6G | 10C | 10C | 10C | 9G, 9C | 10E | 5G, 2C |
| 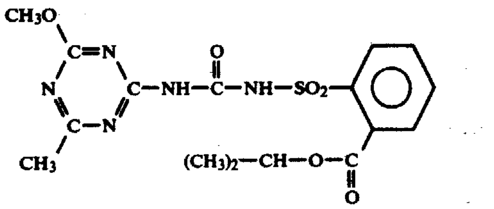 | 1/16 | 8G, 8C | 10E | 7G | 9G, 5H | 9G, 9C | 8G, 9C | 10C | 10C | 5G | 9G, 9C | 6G, 3C | 0 |
| | 1/4 | 8G, 8C | 10E | 9G | 9G, 5H | 9G, 9C | 10C | 10C | 10C | 8G, 7C | 9G, 9C | 8G, 8C | 0 |
| 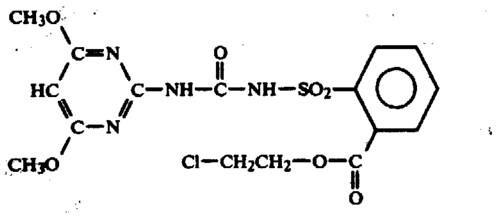 | 1/16 | 7G, 5H | 10E | 10E | 3G | 5G | 7G, 5C | 3H | 10C | 5G | 8G, 8H | 10C | 5G |
| | 1/4 | 8G, 5C | 10E | 10E | 8G | 10C | 8G, 7C | 7G, 5H | 10C | 7G | 9G, 9H | 10E | 6G |
| 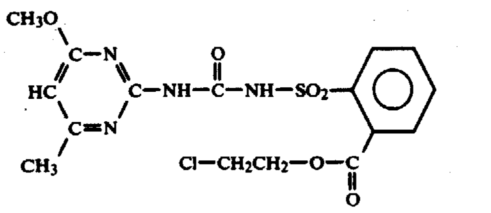 | 1/16 | 8G, 5H | 10E | 10E | 6G, 2H | 10C | 7G, 3C | 9G, 9C | 10C | 6G | 8G, 8H | 10E | 7G |
| | 1/4 | 7G, 5H | 10E | 10E | 8G, 5H | 8G, 5C | 8G, 7C | 10C | 10C | 8G, 7C | 8G, 9H | 10E | 10C |

TABLE XIII-continued
Preemergence on Fallsington Silt Loam
| | | | | | | | | | | | | | |
|---|---|---|---|---|---|---|---|---|---|---|---|---|---|
| 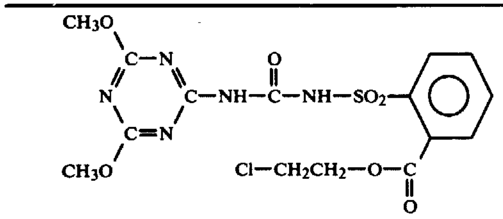 | 1/16 | 8G, 5H | 10E | 8G | 7G, 5H | 8G | 7G, 3C | 5G, 6H | 7G, 7C | 3G | 3G | 6G, 3C | 0 |
| | 1/14 | 8G, 5C | 10E | 8G | 8G, 5H | 8G, 5C | 8G, 9C | 10C | 10C | 5G | 6G, 5H | 5G, 3C | 0 |
| 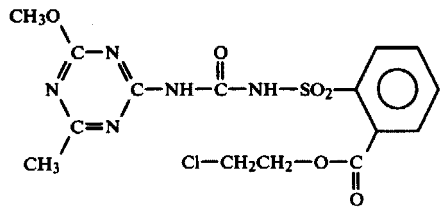 | 1/16 | 8G, 5H | 10E | 7G | 7G | 8G | 7G, 3C | 5G, 5H | 10C | 3G | 2G, 2H | 6G, 3C | 0 |
| | 1/4 | 8G, 8C | 10E | 7G | 8G | 8G, 5C | 8G, 9C | 10C | 10C | 5G | 7G, 7H | 6G, 3C | 0 |

TEST C

Pots filled with Fallsington silt loam were planted to soybeans, cotton, corn, rice, wheat, sorghum, alfalfa, velvet leaf (*Abutulon theophrasti*), sesbania (*Sesbania exaltata*), cassia (*Cassia tora*), morningglory (Ipomoea spp.), jimsonweed (*Datura stramonium*), cocklebur (*Xanthium pennsylvanicum*), crabgrass (Digitaria spp.), nutsedge (*Cyperus rotunda*), barnyardgrass (*Echinochloa crusgalli*), giant foxtail (*Setaria faberii*), and wild oats (*Avena fatua*). Approximately 2½ weeks after planting, the young plants and the soil around them were sprayed overall with the compund of Example 1 dissolved in a nonphytotoxic solvent. Other groups of all the same weed and crop plants were sprayed with the same nonphytotoxic solvent so as to provide control plants. Fourteen days after treatment, all treated plants were compared with the nonphytotoxic solvent controls and visually rated for response to treatment to give the data presented in Table XIV. It will be noted that wheat shows tolerance for several of the compounds included in this table.

TABLE XIV

OVER-THE-TOP SOIL/FOLIAGE TREATMENT

| | Rate kg/ha | Soybeans | Velvetleaf | Sesbania | Cassia | Cotton | Morningglory | Alfalfa | Jimsonweed | Cocklebur | Corn | Crabgrass | Rice | Nutsedge | Barnyardgrass | Wheat | Giant Foxtail | Wild Oats | Sorghum |
|---|---|---|---|---|---|---|---|---|---|---|---|---|---|---|---|---|---|---|---|
| 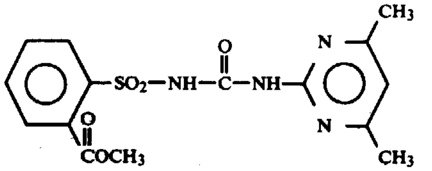 | 1/16 | 10G, 8C | 10C | 10G 9C | 10G 6C | 10G 7C | 10G 7C | 10G 9C | 10G 8C | 10G 9C | 10G 4C | 10G 4C | 10G 6C | 10G 8C | 10G 7C | 10G 7C | 10G 8C | 10G 9C | |
| | 1/4 | 10G 7C | 10C | 10C | 10G 7C | 10G 6C | 10C | 10G 9C | 10G 8C | 10C | 10G 8C | 10G 6C | 10G 7C | 10G 9C | 10G 7C | 10G 8C | 10G 9C | 10G 8C | |
| 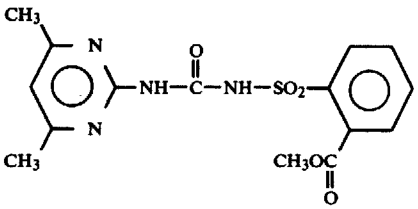 | 1/500 | 10G, 8C | 10C | 8G, 7C | 8G, 3C | 10G, 7C | 2G | 5G | 3G | 10G | 10G, 7C | 5G | 10G, 4C | 10G, 3C | 10C | 10G, 9C | 10G, 8C | 8G, 3C | 10G, 3C |
| | 1/250 | 10G, 9C | 10C | 10G, 8C | 10G, 8C | 10C | 6G | 10G, 6C | 8G, 3C | 8G, 2C | 8G, 3U | 5G | 8G, 2C | 10G, 4C | 10G, 3C | 8G | 8G | 8G | 10G, 4C |
| | 1/128 | 10G, 9C | 10C | 10G, 9C | 10G, 6C | 10G, 9C | 7G, 3C | 10G, 5C | 10C | 10G, 8C | 10G, 9C | 6G | 10G, 5C | 10C | 10G, 8C | 10G, 4C | 10G, 7C | 10G, 5C | 10G, 7C |
| | 1/64 | 10G, 8C | 10G, 8C | 10G, 9C | 10G, 8C | 10G, 8C | 10G, 9C | 10G, 8C | 10G, 9C | 10G, 7C | 10G, 9C | 6G | 10G, 6C | 10G, 8C | 10G, 9C | 10G, 9C | 10G, 9C | 10G, 7C | 10G, 8C |
| | 1/32 | 10G, 8C | 10C | 10G, 9C | 10G, 8C | 10G, 8C | 10G, 9C | 10G, 8C | 10C | 10C | 10G, 8C | 10G, 4C | 10G, 6C | 10G, 9C | 10G, 9C | 10G, 7C | 10G, 9C | 10G, 7C | 10G, 8C |
| 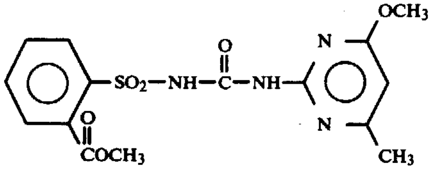 | 1/64 | 10G, 9C | 10C | 10G, 9C | 10G, 9C | 10G, 7C | 10G, 9C | 10G, 9C | 10C | 10G, 9C | 10G, 8C | 3G | 10G, 3C | 10G, 6C | 10G, 9C | 10G, 8C | 10G, 7C | 10G, 7C | 10G, 7C |
| | 1/32 | 10G, 9C | 10C | 10G, 9C | 10G, 8C | 10G, 7C | 10C | 10C | 10C | 10G, 9C | 10G, 7C | 7G, 3C | 10G, 4C | 10G, 6C | 10G, 7C | 10G, 7C | 10G, 7C | 10G, 9C | 10G, 7C |
| | 1/16 | 10G, 8C | — | 10G, 9C | 10G, 9C | 10G, 7C | 10C | 10G, 9C | 10C | 10C | 10G, 9C | 10G, 5C | 10G, 6C | 10G, 8C | 10G, 9C | 10G, 9C | 10C | 10G, 8C | 10G, 9C |
| 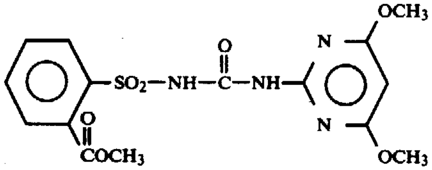 | 1/64 | 10G, 9C | 10C | 10G, 9C | 10G, 8C | 10G, 6C | 10C | 10G, 9C | 10C | 10C | 10G, 7C | 4G | 10G, 4C | 10G, 9C | 10G, 7C | 8G, 3C | 10G, 9C | 10G, 6C | 10G, 8C |
| | 1/32 | 10G, 9C | 10C | 10G, 9C | 10C | 10G, 6C | 10C | 10G, 9C | 10C | 10C | 10G, 8C | 5G, 2C | 10G, 4C | 10G, 9C | 10G, 9C | 10G, 7C | 10G, 9C | 10G, 5C | 10G, 9C |
| | 1/16 | 10G, 8C | 10C | 10G, 9C | 10G, 9C | 10G, 8C | 10G, 9C | 10G, 9C | 10C | 10C | 10G, 8C | 3G, 2C | 10G, 4C | 10G, 9C | 10G, 8C | 10G, 8C | 10C | 8G, 4C | 10G, 9C |

TABLE XIV-continued

OVER-THE-TOP SOIL/FOLIAGE TREATMENT

| | Rate kg/ha | Soybeans | Velvetleaf | Sesbania | Cassia | Cotton | Morningglory | Alfalfa | Jimsonweed | Cocklebur | Corn | Crabgrass | Rice | Nutsedge | Barnyardgrass | Wheat | Giant Foxtail | Wild Oats | Sorghum |
|---|---|---|---|---|---|---|---|---|---|---|---|---|---|---|---|---|---|---|---|
| 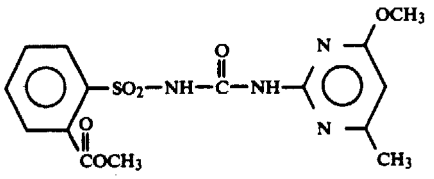 | 1/64 | 10G, 8C | — | 10G, 9C | 10G, 7C | 10G, 5C | 10C | 10G, 8C | 10C | 10G, 8C | 9G, 3C | 0 | 7G | 0 | 8G, 5H | 7G, 3H | 10G, 2C | 6G | 10G, 2C |
| | 1/32 | 10G, 8C | 10C | 10G, 9C | 10G, 9C | 10G, 8C | 10C | 10G, 9C | 10C | 10C | 10G, 8C | 3G, 2H | 10G, 2C | 4G | 10G, 6C | 5G | 10G, 7C | 10G, 2C | 10G, 5C |
| | 1/16 | 10G, 9C | 10C | 10G, 9C | 10G, 8C | 10G, 8C | 10C | 10G, 9C | 10C | 10C | 10G, 9C | 5G, 2C | 10G, 4C | 2G | 10G, 7C | 5G | 10G, 4C | 10G, 3C | 10G, 5C |
| 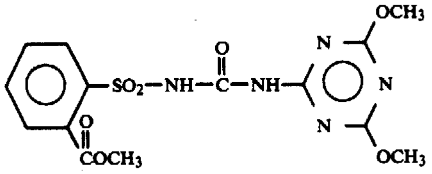 | 1/64 | 10G, 8C | — | 10G, 9C | 10G, 8C | 10G, 5C | 10G, 9C | — | 10G, 9C | 10G, 2C | 8G, 4H | 0 | 6G | 0 | 6G, 2H | 3G, 2H | 3G | 0 | 5G, 2H |
| | 1/32 | 10G, 8C | — | 10G, 9C | 10G, 8C | 10G, 9C | 10C | 8G, 6C | 10C | 10G, 7C | 8G, 2C | 0 | 10G, 2C | 0 | 9G, 3H | 3G | 7G | 2G | 10G, 4H |
| | 1/16 | 10G, 8C | 10C | 10G, 9C | 10G, 8C | 10G, 8C | 10C | 10G, 6C | 10C | 10G, 9C | 9G, 4C | 2G | 10G, 3C | 5G, 2C | 10G, 5H | 3G | 10G, 3C | 3G, 2C | 10G, 4H |
| 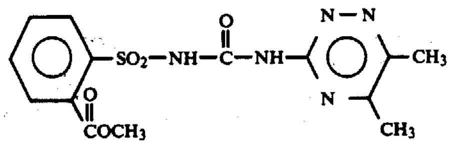 | 1/16 | 10G, 8C | 5G | 10C | 10G, 8C | 5G, 2C | 4G | 2C | 4G, 2C | 3G, 3C | 6G, 3H | 0 | 10G, 8C | 10G, 3C | 10G, 4C | 8G | 5G | 5G | 10G, 6C |
| | 1/4 | 10G, 9C | 10C | 10C | 10G, 8C | 7G, 3H | 9G, 3C | 10G, 6C | 6G, 2C | 9G, 6C | 10G, 7C | 2G | 10G, 7C | 10G, 3C | 10G, 5C | 10G | 8G | 8G | 10G, 6C |
| 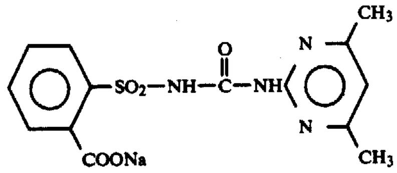 | 1/32 | 0 | 0 | 0 | 0 | 0 | 0 | 0 | 0 | 0 | 0 | 0 | 0 | 0 | 0 | 0 | 0 | 0 | 0 |
| | 1/16 | 0 | 0 | 3G | 0 | 0 | 0 | 0 | 0 | 0 | 0 | 0 | 3G | 3G | 0 | 0 | 0 | 0 | 4G |
| | 1/4 | 5G, 2C | 5G | 7G | 5G, 3C | 5G | 5G | 3G | 2G | 3G | 8G, 5H | 0 | 8G | 8G | 4G | 4G | 2G | 3G | 8G, 3H |

TABLE XIV-continued

OVER-THE-TOP SOIL/FOLIAGE TREATMENT

| | Rate kg/ha | Soybeans | Velvetleaf | Sesbania | Cassia | Cotton | Morningglory | Alfalfa | Jimsonweed | Cocklebur | Corn | Crabgrass | Rice | Nutsedge | Barnyardgrass | Wheat | Giant Foxtail | Wild Oats | Sorghum |
|---|---|---|---|---|---|---|---|---|---|---|---|---|---|---|---|---|---|---|---|
| 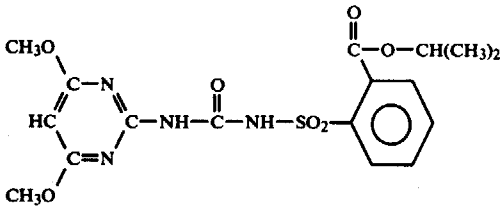 | 1/32 | 10G, 8C | 10C | 10G, 9C | 10G, 8C | 10C | 10C | 10C | 10C | 10C | 8G, 3H | 5G | 10G, 6C | 10G, 8C | 10G, 8C | 8G | 10G | 10G | 10G, 5C |
| | 1/16 | 10G, 8C | 10C | 10C | 10G, 8C | 10C | 10C | 10C | 10C | 10C | 10G, 3C | 5G | 10G, 5C | 10G, 9C | 10G, 9C | 10G | 10G | 10G | 10C |
| | 1/4 | 10C | 10C | 10C | 10G, 9C | 10C | 10C | 10C | 10C | 10C | 10G, 8C | 9G, 3C | 10G, 6C | 10G, 8C | 10G, 9C | 10G, 3H | 10G, 3C | 10G, 3C | 10G, 8C |
| 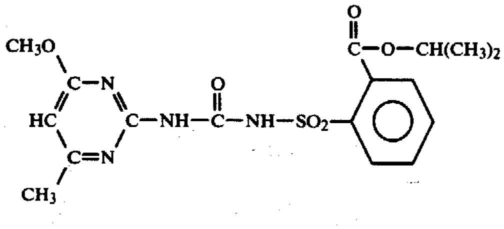 | 1/32 | 10G, 8C | 10C | 10G, 9C | 10G, 8C | 10C | 10C | 10C | 10C | 10G, 9C | 8G, 3C | 8G | 10G, 5C | 10G, 8C | 10G, 8C | 9G | 10G | 10G | 10G, 4C |
| | 1/16 | 10G, 8C | 10C | 10C | 10G, 8C | 10C | 10C | 10C | 10C | 10C | 7G, 3C | 8G | 10G, 4C | 8G, 3C | 10G, 6C | 10G, 3C | 10G | 10G, 3C | 10G, 3C |
| | 1/4 | 10G, 8C | — | 10C | 10G, 8C | 10C | 10C | 10C | 10C | 10C | 10G, 9C | 10G, 3C | 10G, 6C | 10G, 8C | 10G, 8C | 10G, 5C | 10G, 6C | 10G, 5C | 10G, 8C |
| 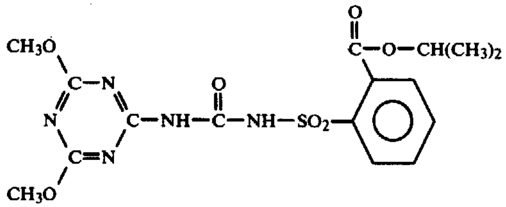 | 1/32 | 10G, 8C | 10C | 10C | 10G, 9C | 10G, 7C | 10C | 10G, 9C | 10C | 10C | — | 0 | 6G | 10G, 8C | 7G, 3H | 0 | 2G | 5G | 8G, 3H |
| | 1/16 | 10G, 9C | 10C | 10C | 10G, 9C | 10C | 10C | 10C | 10C | — | 8G, 5H | 3G | 8G | 10G, 9C | 8G, 3H | 0 | 0 | 5G | 10G, 3H |
| | 1/4 | 10G, 8C | 10C | 10C | 10G, 9C | 10C | 10C | 10C | 10C | 10C | 10G, 4C | 7G | 10G, 4C | 10C | 8G, 3H | 0 | 5G | 8G | 10G, 3H |
| 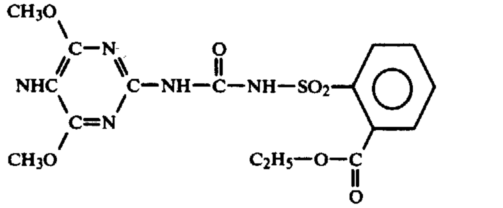 | 1/32 | 10G, 8C | 10C | 10C | 10G, 9C | 10G, 9C | 10C | 10C | 10G, 9C | 10C | 10G, 9C | 5G | 10G, 7C | 10C | 10G, 8C | 8G | 7G | 10G, 6C | 10C |
| | 1/16 | 10C | 10C | 10C | 10G, 9C | 10C | 10C | 10C | 10C | 10C | 10G, 9C | 7G | 10G, 7C | 10C | 10G, 7C | 10G, 3C | 10G | 10G, 5C | 10G, 8C |
| | 1/4 | 10G, 9C | 10C | 10G, 9C | 10G, 9C | 10C | 10C | 10C | 10C | 10C | 10C | 10G, 3C | 10G, 7C | 10C | 10G, 9C | 10G, 4C | 10G, 3C | 10G, 7C | 10C |

TABLE XIV-continued

OVER-THE-TOP SOIL/FOLIAGE TREATMENT

| | Rate kg/ha | Soy-beans | Vel-vet-leaf | Ses-bania | Cas-sia | Cot-ton | Morn-ing-glory | Al-fal-fa | Jim-son-weed | Cock-lebur | Corn | Crab-grass | Rice | Nut-sedge | Barn-yard-grass | Wheat | Gi-ant Fox-tail | Wild Oats | Sor-ghum |
|---|---|---|---|---|---|---|---|---|---|---|---|---|---|---|---|---|---|---|---|
| 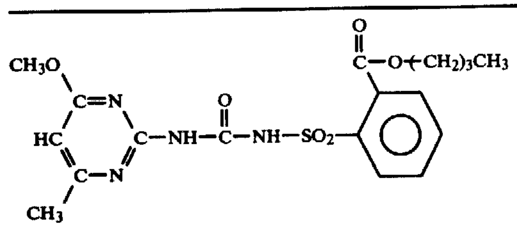 | 1/32 | 10G, 3C | 10G, 7C | 10G, 5C | 3G | 10G, 4C | 10G, 3B | 10G, 6C | 8G, 3C | 10G, 4C | 5G, 2H | 0 | 8G | 3G | 8G, 2C | 0 | 7G | 6G | 5G |
| | 1/16 | 10G, 6C | 10C | 10G, 7C | 4G | — | 10G, 5B | 10G, 6C | 8G, 3C | 10G, 6C | 8G, 3H | 0 | 10G, 2C | 8G | 10G, 3C | 3G | 7G | 7G | 10G, 3H |
| | 1/4 | 10G, 6C | 10C | 10G, 8C | 8G, 3C | 10G, 8C | 10B | 10G, 9C | 10G, 6C | 10G, 6C | 10G, 3H | 0 | 10G, 4C | 9G | 10G, 3C | 5G | 10G, 3H | 9G | 10G, 3H |
| 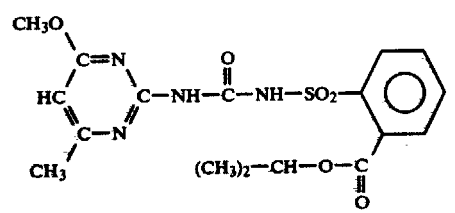 | 1/16 | 10G, 9C | 10C | 10C | 10C | 10C | 10C | 10C | 10G, 6C | 10C | 10G, 2C | 4G | 7G | 8G, 3C | 7G | 0 | 0 | 3G | 8G, 4H |
| | 1/4 | 10G, 9C | — | 10C | 10G, 9C | 10C | 10C | 10C | 10G, 7C | 10C | 10G, 8C | 7G | 10G, 2C | 10C | 10G, 3C | 3G | 7G | 8G | 8G, 2C |
| 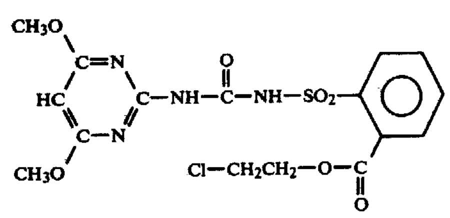 | 1/16 | 10G, 9C | 10C | 10G, 9C | 10G, 8C | 10G, 8C | 10C | 10G, 9C | 8G, 3C | 10C | 8G, 2C | 5G | 10G, 4C | 10G, 6C | 10G, 7C | 6G | 10G, 7C | 8G | 10G |
| | 1/4 | 10G, 9C | — | 10C | 10C | 10G, 9C | 10C | 10C | 10G, 5C | 10C | 9G, 2C | 8G, 2C | 10G, 5C | 10G, 6C | 10G, 8C | 10G | 10G, 9C | 10G, 3C | 10G |
| 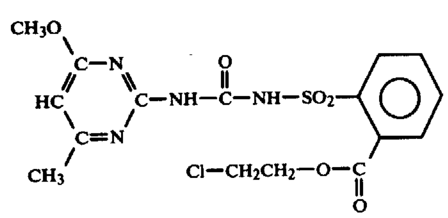 | 1/16 | 10G, 9C | — | 10C | 10C | 10C | 10G, 9C | 10C | 10G, 7C | — | 10G, 5C | 4G | 10G, 4C | 10G, 8C | 10G, 8C | 10G | 10G, 3C | 10G, 2C | 10G |
| | 1/4 | 10G, 9C | — | 10C | 10C | 10G, 8C | 10G, 9C | 10C | 10G, 8C | 10C | 10G, 3C | 7G | 10G, 5C | 10G, 5C | 10G, 8C | 10G, 4C | 10G, 9C | 10G, 2C | 10G, 2C |

TABLE XIV-continued

OVER-THE-TOP SOIL/FOLIAGE TREATMENT

| | Rate kg/ha | Soy-beans | Vel-vet-leaf | Ses-bania | Cas-sia | Cot-ton | Morn-ing-glory | Al-fal-fa | Jim-son-weed | Cock-lebur | Corn | Crab-grass | Rice | Nut-sedge | Barn-yard-grass | Wheat | Gi-ant Fox-tail | Wild Oats | Sor-ghum |
|---|---|---|---|---|---|---|---|---|---|---|---|---|---|---|---|---|---|---|---|
| 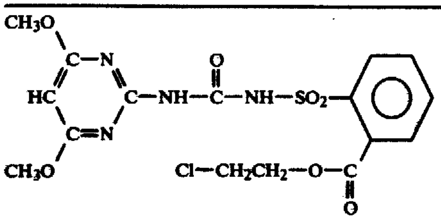 | 1/16 | 10G, 9C | — | 10C | 10G, 9C | 10G, 9C | 10C | 5G | 8G, 4C | 10C | 5G | 3G | 4G | 10G, 4C | 7G | 0 | 0 | 0 | 6G |
| | 1/4 | 10G, 9C | 10C | 10C | 10C | 10G, 8C | 10C | 10G, 9C | 10G, 4C | — | 8G, 2C | 4G | 6G | 10G, 4C | 8G | 0 | 0 | 5G | 8G |
| 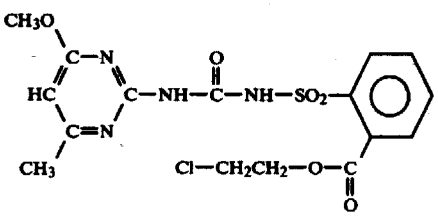 | 1/16 | 10G, 9C | 10G | 10C | 10G, 9C | 10G, 8C | 10C | 10C | 10G, 5C | 10C | 10G, 3H | 0 | 4G | 5G | 6G | 0 | 0 | 3G | 10G, 3H |
| | 1/4 | 10G, 9C | — | 10C | 10C | 10G, 9C | 10C | 10C | 10G, 8C | 10C | 10G, 3C | 3G | 7G | 9G, 4C | 8G | 0 | 3G | 5G | 10G |
| 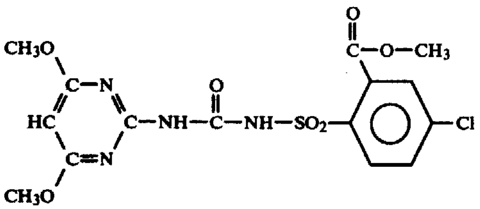 | 1/16 | 10G, 7C | 10C | 10C | 10G, 7C | 10G, 7C | 10G, 9C | 10G, 9C | 10G, 3C | 10C | 4G | 0 | 10G, 3C | 10G, 5C | 10G, 3H | 2G | 0 | 5G | 10G |
| | 1/4 | 10G, 8C | 10C | 10C | 10G, 7C | 10G, 9C | 10C | 10G, 9C | 10G, 6C | 10C | 7G, 3H | 4G | 10G, 3C | 10G, 8C | 10G, 4C | 7G | 5G, 2C | 8G, 3H | 10G, 2C |
| 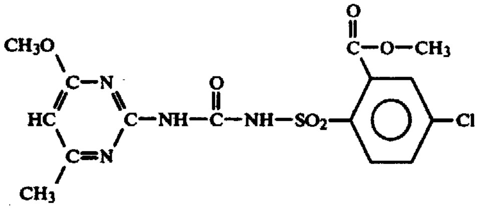 | 1/16 | 10G, 7C | 10C | 10G, 7C | 10G, 7C | 10G, 6C | 10C | 10G, 9C | 10G, 8C | 10C | 10G, 5H | 0 | 8G, 2C | 7G, 2C | 8G, 3C | 4G | 2G | 10G | 10G |
| | 1/4 | 10G, 7C | 10C | 10G, 9C | 10G, 7C | 10G, 9C | 10C | 10G, 9C | 10G, 8C | 10G, 9C | 8G | 5G | 10G, 6C | 7G, 3C | 10G, 6C | 8G | 6G | 8G, 3C | 10G |

TEST D

The high herbicidal activity of one of the compounds from within the scope of the invention is evident from the results obtained in this test. The experiment concerned pre-emergence applications on soil. The containers used were 25 cm diameter plastic pots filled with Fallsington silt loam. One set of pots was planted to weeds the seeds of which were uniformly mixed with the top 1.2 cm layer of soil. The species selected were: johnsongrass (*Sorghum halepense*), barnyardgrass (*Echinochloa crusgalli*), crabgrass (*Digitaria sanguinalis*), giant foxtail (*Setaria faberii*), velvetleaf (*Abutilon theophrasti*), jimsonweed (*Datura stramonium*), mustard (*Brassica arvensis*) and pigweed (*Amaranthus retroflexus*). Another set of pots was planted to the following crops with from one to four species per pot: corn (planting depth 3.7 cm), cotton, soybeans, sunflower, Clinton oats, wheat, Black Valentine beans, rice, sorghum, peas, flax and peanuts (all at 2.5 cm depth), cucumbers, cabbage, alfalfa, safflower, sugarbeets, tomato, spinach, barley and Kentucky bluegrass (all at 1.2 cm depth). Immediately after planting, the test chemical was applied to the soil surfaces dissolved in a non-phytotoxic solvent. One pot from the weed phase and one of each of the crop species were left untreated for the purpose of comparison. The treated and untreated pots were promptyly watered with approximately 4 mm of simulated rainfall and then held in a greenhouse for several weeds. Visual weed and crop response ratings were made 28 days after treatment utilizing the rating system as described above for test procedure A. The data are given in Table XV.

TABLE XV

PRE-EMERGENCE ON SOIL

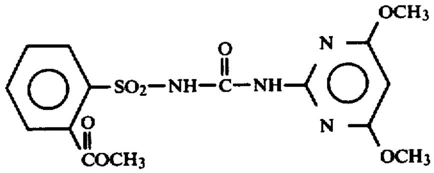

| Rate kg/ha | 1/64 | 1/32 | 1/16 | 1/2 |
|---|---|---|---|---|
| Corn | — | — | — | 10C |
| Cotton | — | — | — | 9G,9C |
| Soybean | — | — | — | 9G,9H |
| Peanut | — | — | — | 10E |
| Sunflower | — | — | — | 8G,7C |
| Oats | — | — | — | 8G,9C |
| Wheat | — | — | — | 10C |
| Sorghum | — | — | — | 10C |
| Sugarbeet | — | — | — | 10C |
| Pea | — | — | — | 10C |
| Flax | — | — | — | 10E |
| Alfalfa | — | — | — | 10C |

TABLE XV-continued

PRE-EMERGENCE ON SOIL

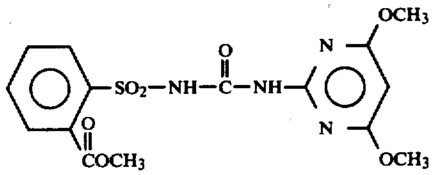

| Rate kg/ha | 1/64 | 1/32 | 1/16 | 1/2 |
|---|---|---|---|---|
| Bean | — | — | — | 7G,8H |
| Spinach | — | — | — | 10C |
| Cabbage | — | — | — | 10C |
| Tomato | — | — | — | 8G,8C |
| Rice | — | — | — | 10E |
| Safflower | — | — | — | 9G,9C |
| Cucumber | — | — | — | 8G,7C |
| Ky. bluegrass | — | — | — | 10C |
| Barley | — | — | — | 9G,8C |
| Tobacco | — | — | — | 5G,2C |
| Broadleaves | 7G,5C | 8G,8C | 9G,8C | — |
| Grasses | 6G | 8G,6C | 8G,8C | — |

TEST E

This greenhouse test demonstrates the utility of certain compounds from within the scope of the invention for the pre- and post-emergence control of broadleaved weeds and nutsedge in young wheat and barley plantings. The containers used were 25 cm diameter plastic pots filled with fertilized and limed Fallsington silt loam. Plantings of the following weed species were made twice, at a 10-day interval: mustard (*Brassica arvensis*), cocklebur (*Xanthium spp.*), morningglory (*Ipomoea hederacea*), cassia (*Cassia tora*), velvetleaf (*Abutilon theophrasti*), alfalfa (used as an indicator species), kochia (*Kochia scoparia*), sesbania (*Sesbania exaltata*), Russian thistle (*Salsola kali*), jimsonweed (*Datura stramonium*), and nutsedge (*Cyperus rotundus*). In addition, wheat and barley were planted in separate 15 cm diameter plastic pots filled with the same soil at the time of the early planting only. All plantings were treated with the test chemicals dissolved in a non-phytotoxic solvent immediately following completion of the second planting operation. At this time, the wheat was around 15-17.5 cm tall and the barley 12.5 to 15 cm tall, both in the 2-leaf stage of growth. The weed species of the earliest planting date were from 2.5 to 12.5 cm tall. The rates of application selected were 0.004, 0.007, 0.015 and 0.030 kg/ha for the weed phase and 0.12, 0.25 and 0.50 kg/ha for wheat and barley. The post-emergence part of this test was visually rated for plant response 21 days after treatment, and the pre-emergence part 28 days after treatment. The rating system used was as described for test procedure A. The data are summarized in Table XVI.

TABLE XVI

| | 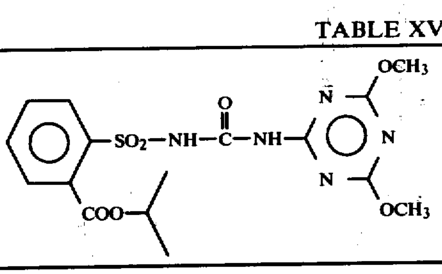 | | | | 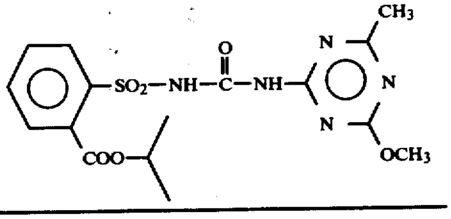 | | |
|---|---|---|---|---|---|---|---|
| Rate kg/ha | 1/256 | 1/128 | 1/64 | 1/32 | 1/256 | 1/128 | 1/64 | 1/32 |

TABLE XVI-continued

| | 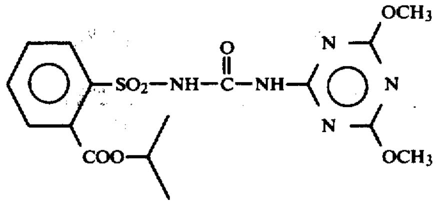 | | | | 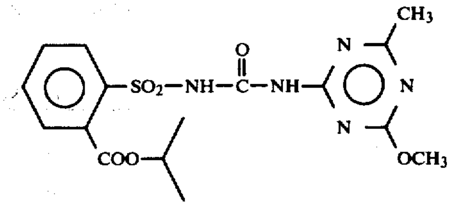 | | | |
|---|---|---|---|---|---|---|---|---|
| | PRE-EMERGENCE ON FALLSINGTON SILT LOAM | | | | | | | |
| Mustard | 9G,9C | 10C | 10C | 10C | 10C | 10C | 10C | 10C |
| Cocklebur | 7G,7H | 8G,8H | 8G,8H | 8G,9H | 8G,8C | 8G,8H | 8G,8H | 8G,9H |
| Morningglory | 8G,7C | 8G,7C | 8G,7C | 8G,9C | 8G,6C | 9G,9C | 10C | 10C |
| Cassia | 8G,5C | 8G,5C | 8G,5C | 8G,8C | 8G,5C | 8G,5C | 8G,9C | 8G,8C |
| Velvetleaf | 8G,3H | 8G,3H | 8G,5H | 9G,5H | 9G,8C | 9G,9C | 10C | 10C |
| Alfalfa | 5G | 5G,2C | 5G | 8G,7C | 7G | 7G,2C | 9G,8C | 9G,7C |
| Sesbania | 7G,3C | 8G,9C | 8G,9C | 9G,9C | 7G,3C | 7G,5C | 8G,8C | 10C |
| Kochia | 9G,9C | 10C | 10C | 10C | 9G,9C | 10C | 10C | 10C |
| R. Thistle | 5C | 7C | 7C | 9C | 7C | 8C | 10C | 10C |
| Jimsonweed | 7G,2C | 8G,7C | 8G,9C | 8G,9C | 7G,6C | 7G,5C | 8G,9C | 8G,7C |
| Nutsedge | 7G | 8G | 9G | 10E | 6G,3C | 7G,2C | 8G | 8G |
| | POST-EMERGENCE | | | | | | | |
| Mustard | | | | | | | | |
| Cocklebur | 10C | 10C | 10C | 10C | 10C | 10C | 10C | 10C |
| Morningglory | 10C | 10C | 10C | 10C | 10C | 10C | 10C | 10C |
| Cassia | 9C | 10C | 10C | 10C | 10C | 9C | 10C | 10C |
| Velvetleaf | — | 10C | 10C | — | — | 10C | — | — |
| Alfalfa | 5G | 10C | 10C | 10C | 10C | 10C | 10C | 10C |
| Sesbania | 10C | 10C | 10C | 10C | 10C | 10C | 10C | 10C |
| Kochia | — | — | 10C | — | 10C | — | 10C | — |
| R. Thistle | 8C | 10C | 10C | 10C | 10C | 10C | 10C | 10C |
| Jimsonweed | 7G,5C | 10G,5C | 10G,7C | 10G,6C | 10G,4C | 10G,8C | 10G,8C | 10G,9C |
| Nutsedge | 7G,3C | 10G,8C | 10G,5C | 10G | 3G | 5G,3C | 10G,7C | 10C |

| Rate kg/ha | 1/8 | 1/4 | 1/2 | 1/8 | 1/4 | 1/2 |
|---|---|---|---|---|---|---|
| Wheat | 2G | 2G,2C | 6G,3C | 0 | 0 | 5G,3C |
| Barley | 0 | 6G,2C | 8G,3C | 5G | 5G,2C | 7G,3C |

TEST F

Several compounds from within the scope of the invention are highly active against nutsedge, as evident from the following test.

Purple nutsedge tubers (*Cyperus rotundus*) were planted about 2 cm deep in Fallsington silt loam contained in plastic pots 10 cm in diameter. Five tubers were put in each pot. Compounds of this invention were sprayed dissolved in a non-phytotoxic solvent at a volume rate of 560 l/ha. in four different methods of treatment, i.e., soil surface spray, tuber/soil spray, soil incorporated and post-emergence. For the soil surface spray, the compounds were sprayed on the firmed soil surface immediately after planting. For the tuber/soil spray, the compounds were sprayed on the exposed tubers and subtending soil before the untreated covering soil was added. Soil incorporation treatments were mixed in the covering soil. Post-emergence treatments were sprayed on the nutsedge foliage and surrounding soil surface after the nutsedge had emerged and had reached the height of about 12 cm.

Immediately after spraying the surface spray, tuber/-soil spray and soil incorporated treatments were misted with about 0.3 cm of water over a 90 minute period and then placed in the greenhouse. Post-emergence treatments were placed directly into the greenhouse and watered carefully so that treatments would not be washed from the foliage.

The following Table XVII gives results 4 weeks after treating nutsedge with compounds of this invention.

TABLE XVII

NUTSEDGE TEST

| | | RESPONSE RATING AFTER 4 WEEKS | | | |
|---|---|---|---|---|---|
| | Rate kg/ha | Soil Surface | Tuber Spray | Soil Incorp. | Post-emergence |
| 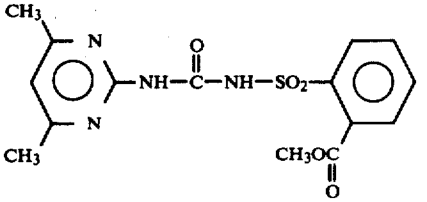 | .004 | 8E,9G | 10E | 10E | 4C,7G |
| | .008 | 10E | 10E | 10E | 9C |
| | .016 | 10E | 10E | 10E | 9C |
| | .032 | 10E | 10E | 10E | 10C |
| | .064 | 10E | 10E | 10E | 10C |

TABLE XVII-continued
NUTSEDGE TEST
| | | RESPONSE RATING AFTER 4 WEEKS | | | |
|---|---|---|---|---|---|
| | Rate kg/ha | Soil Surface | Tuber Spray | Soil Incorp. | Post-emergence |
| 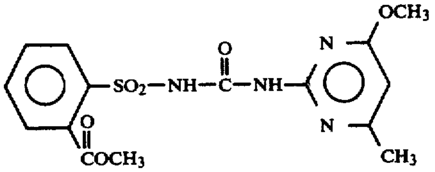 | .004 | 8E,9G | 10E | 10E | 5C,7G |
| | .008 | 10E | 10E | 10E | 9C |
| | .016 | 10E | 10E | 10E | 9C |
| | .032 | 10E | 10E | 10E | 10C |
| | .064 | 10E | 10E | 10E | 10C |
| 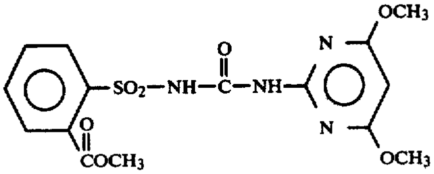 | .004 | 9E,9G | 8E,9G | 8E,9G | 8C |
| | .008 | 10E | 10E | 10E | 10C |
| | .016 | 10E | 10E | 10E | 10C |
| | .032 | 10E | 10E | 10E | 9C |
| | .064 | 10E | 10E | 10E | 10C |
| 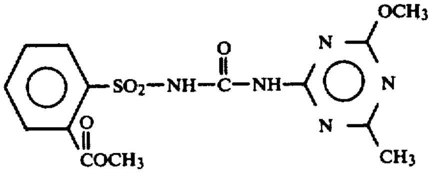 | .004 | 4C,7G | 5C,8G | 5C,8G | 0 |
| | .008 | 4C,7G | 5C,8G | 5C,8G | 2G |
| | .016 | 4C,7G | 5C,9G | 5C,8G | 2G |
| | .032 | 5C,8G | 5C,9G | 5C,9G | 2C,5G |
| | .064 | 5C,8G | 5C,9G | 6C,9G | 5C,7G |
| 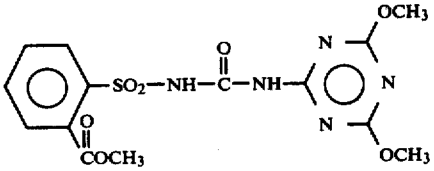 | .004 | 3C,6G | 3C,7G | 3C,7G | 0 |
| | .008 | 4C,8G | 4C,8G | 4C,8G | 0 |
| | .016 | — | 4C,8G | 4C,8G | 2C,3G |
| | .032 | 4C,8G | 4C,8G | 4C,8G | 3G |
| | .064 | 5C,8G | — | 4C,8G | 3C,4G |
| 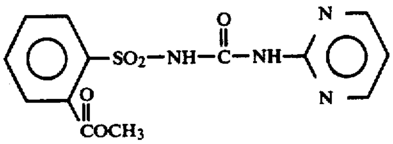 | .032 | 0 | 2G | 0 | 0 |
| | .125 | 2E,7G | 4E,8G | 8E,9G | 9C |
| | .5 | 10E | 10E | 10E | 10E |
| 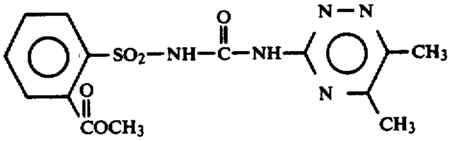 | .032 | 2G | 2G | 3G | 0 |
| | .125 | 10E | 4E,8G | 8E,8G | 9C |
| | .5 | 10E | 10E | 10E | 10C |
| 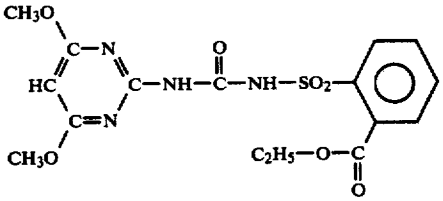 | .008 | 10E | 10E | 10E | 10C |
| | .032 | 10E | 10E | 10E | 10C |
| | .125 | 10E | 10E | 10E | 10C |
| | .25 | 10E | 10E | 10E | 10C |
| 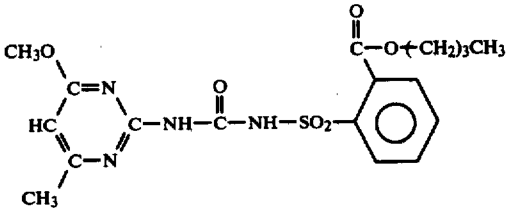 | .008 | 2C,4G | 3C,7G | 3C,8G | 5C,7G |
| | .032 | 3C,6G | 3C,7G | 3C,7G | 3C,6G |
| | .125 | 2C,8G | 3C,8G | 5E,9G | 8C |
| | .5 | 2C,8G | 5E,9G | 5E,9G | 5C,6G |

TABLE XVII-continued

NUTSEDGE TEST

| | | RESPONSE RATING AFTER 4 WEEKS | | | |
|---|---|---|---|---|---|
| | Rate kg/ha | Soil Surface | Tuber Spray | Soil Incorp. | Post-emergence |
| 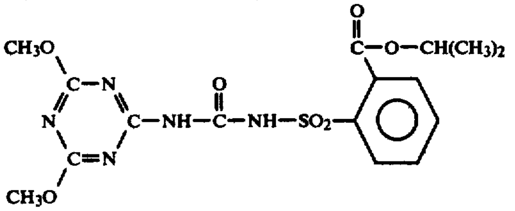 | .004 | 8G | 7G | 8G | 8C |
| | .008 | 8G | 8G | 8G | 9C |
| | .016 | 8E,9G | 6E,9G | 8E,9G | 9C |
| | .032 | 5E,9G | 8E,9G | 10E | 10C |
| 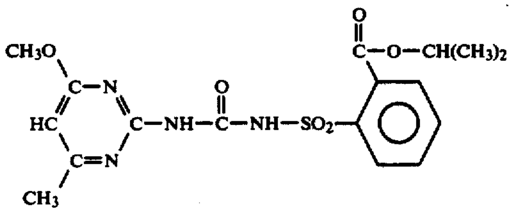 | .008 | 10E | 10E | 9E,9G | 10C |
| | .032 | 10E | 10E | 10E | 10C |
| | .125 | 10E | 10E | 10E | 10C |
| | .25 | 10E | 10E | 10E | 10C |
| 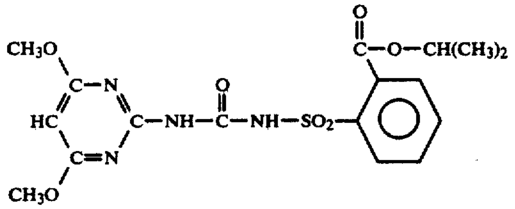 | .008 | 10E | 10E | 10E | 10C |
| | .032 | 10E | 10E | 10E | 10C |
| | .125 | 10E | 10E | 10E | 10C |
| | .25 | 10E | 10E | 10E | 10C |
| 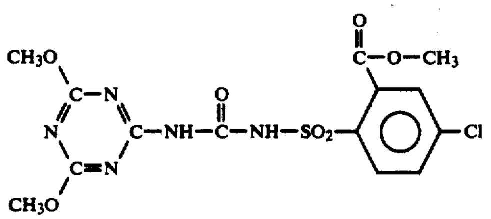 | .008 | 3G | 4G | 5G | 3G |
| | .032 | 7G | 7G | 7G | 5C,6G |
| | .125 | 9G | 9G | 9G | 10C |
| 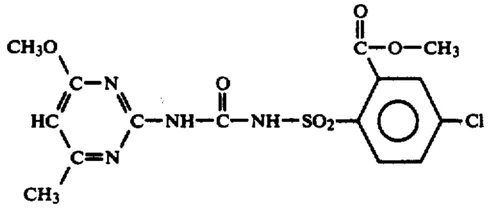 | .008 | 2C,5G | 7G | 7G | 2C,5G |
| | .032 | 9G | 10E | 8E,9G | 9C |
| | .125 | 10E | 10E | 10E | 9C |
| 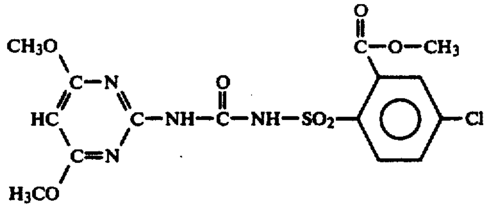 | .008 | 8E,9C | 10E | 10E | 10C |
| | .032 | 10E | 10E | 10E | 10C |
| | .125 | 10E | 10E | 10E | 10C |

TEST G

Purple nutsedge tubers (*Cyperus rotundus*, L.) were planted about 2 cm deep in Fallsington silt loam (about 1% organic matter from Delaware) and in Flanagen loam (about 4% organic matter) from Illinois. Five tubers were planted in each 10 cm diameter plastic pot. Treatments recorded in Table XVII were applied in three different ways, i.e., soil surface spray, tuber/soil spray and soil incorporated. In surface sprays, the material was sprayed on the firmed soil surface after planting, but before nutsedge emergence. In tuber/soil sprays, the material was sprayed on exposed tubers and subtending soil before the tubers were covered with untreated soil. Soil incorporated treatments were mixed in the covering soil.

Immediately after treating, the treated pots were misted with about 0.3 cm of water over a 90 minute period and placed in the greenhouse. The high degree of activity of these compounds on nutsedge is demonstrated by the ratings after 4 weeks as recorded in Table XVIII.

TABLE XVIII

| | Nutsedge Response Rating - After 4 Weeks | | | | | |
|---|---|---|---|---|---|---|
| | Surface Spray | | Tuber/Soil Spray | | Soil Incorp. | |
| Rate, kg/ha | Low OM | High OM | Low OM | High OM | Low OM | High OM |
| 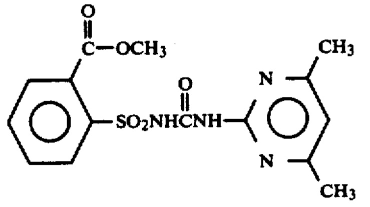 | | | | | | |
| .008 | 10E | 4C,7G | 10E | 7E,9G | 10E | 9E,9G |
| .016 | 10E | 8E,8G | 10E | 10E | 10E | 8E,9G |
| .032 | 10E | 9E,9G | 10E | 10E | 10E | 10E |
| 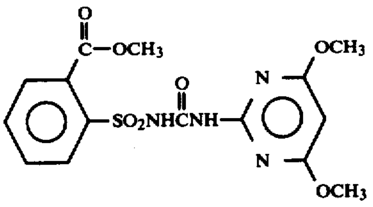 | | | | | | |
| .008 | 5C,8G | 0 | 9E,9G | 5E,7G | 8E,9C | 2C,3G |
| .016 | 9E,9G | 2C,4G | 10E | 10E | 9E,9C | 3C,3G |

TABLE XVIII-continued

| | Nutsedge Response Rating - After 4 Weeks | | | | | |
|---|---|---|---|---|---|---|
| | Surface Spray | | Tuber/Soil Spray | | Soil Incorp. | |
| Rate, kg/ha | Low OM | High OM | Low OM | High OM | Low OM | High OM |
| .032 | 10E | 10C | 10E | 9E,10C | 10C | 7E,3C,8G |

TEST H

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of wild buckwheat (*Polygonum convolvulus*), *Kochia scoparia*, smartweed (*Polygonum pennsylvanicum*), false chamomile (*Matricaria inodora*), jimhill mustard (*Sisymbrium altissium*), wild mustard (*Brassica kaber*), tansy mustard (*Descurainia pinnata*), pigweed (*Amaranthus retroflexus*) and Russian thistle (*Salsola kali*). The above two pans were treated pre-emergence. At the same time two pans in which the above plant species were growing were treated post-emergence. Plant height at the time of treatment ranges from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table XIX. Here again, the potential utility of certain test compounds for weed control in wheat and barley is evident.

TABLE XIX

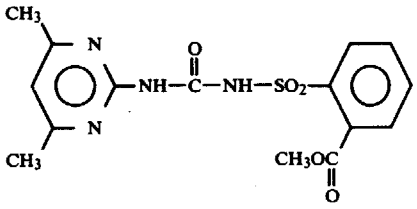

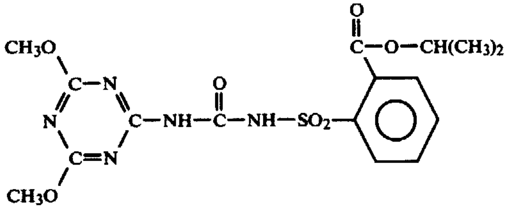

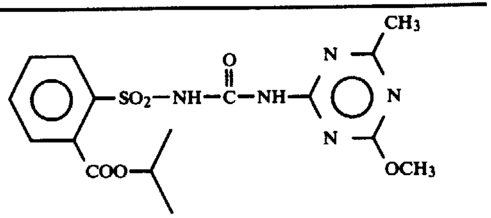

| Rate kg/ha | 1/16 | ¼ | 1/64 | 1/32 | 1/16 | 1/64 | 1/32 | 1/16 |
|---|---|---|---|---|---|---|---|---|
| | | | PRE-EMERGENCE | | | | | |
| wheat | 9E,9G | 9E,9G | 0 | 0 | 0 | 0 | 0 | 0 |
| barley | 7H,8G | 8H,8G | 0 | 0 | 0 | 0 | 1G | 1G |
| wild oats | 4H,7G | 7H,8G | 0 | 0 | 0 | 0 | 2G | 3G |
| downy brome | 9E,9G | 10E | 0 | 0 | 1G | 1G | 3G | 5G |
| cheatgrass | 7G,8G | 9E,9G | 0 | 0 | 1G | 1C,2G | 1C,3G | 2C,4G |
| blackgrass | 5H,8G | 8H,9G | 0 | 0 | 2G | 2G | 3G | 4G |
| annual bluegrass | 5C,7G | 7C,8G | 0 | 0 | 1G | 2G | 3G | 5G |
| green foxtail | 8C,8G | 8C,9G | 0 | 0 | 1G | 0 | 0 | 1G |
| quackgrass | 5H,7G | 7H,8G | 0 | 0 | 0 | 0 | 0 | 2G |
| Italian ryegrass | 6H,7G | 8H,8G | 0 | 0 | 0 | 0 | 2G | 3G |
| ripgut brome | 8C,9G | 10C | 0 | 0 | 0 | 0 | 0 | 0 |
| wild buckwheat | 4C,7G | 5C,8G | 3C,5G | 7C,8G | 7C,8G | 9C | 9C | 10C |
| Kochia | 9C,9G | 9C,9G | 5C,7G | 7C,8G | 9C | 9C | 10C | 10C |
| smartweed | 7C,8G | 9C,9G | 4C,7G | 10C | 10C | 9C | 10C | 10C |
| false chamomile | 9C,9G | 9C,9G | 9G | 9G | 9G | 9G | 9G | 10C |
| jimhill mustard | 10C | 10C | 10C | 10C | 10C | 10C | 10C | 10C |
| wild mustard | 8C,8G | 9C,9G | 10C | 10C | 10C | 10C | 10C | 10C |
| tansy mustard | 10C | 10C | 7C,9G | 10C | 10C | 10C | 10C | 10C |
| pigweed | 8C,9G | 10C | 7G | 5C,8G | 10C | 8C | 9C | 10C |
| Russian thistle | 7C,7G | 8C,8G | 3G | 4G | 7C,5G | 3C,5G | 7C,7G | 8C,8G |
| | | | POST-EMERGENCE | | | | | |
| wheat | 9C | 10C | 0 | 0 | 1C | 0 | 0 | 1C |
| barley | 9C | 10C | 0 | 0 | 0 | 0 | 0 | 0 |
| wild oats | 9C | 10C | 0 | 0 | 1C | 0 | 0 | 2C |
| downy brome | 10C | 10C | 0 | 0 | 0 | 0 | 0 | 2G |
| cheatgrass | 10C | 10C | 0 | 0 | 0 | 0 | 0 | 1C,2G |
| blackgrass | 10C | 10C | 0 | 0 | 0 | 0 | 0 | 2G |
| annual bluegrass | 10C | 10C | 0 | 0 | 2G | 0 | 0 | 3G |
| green foxtail | 10C | 10C | 1C | 1C | 2C,3G | 0 | 1C | 3C |
| quackgrass | 10C | 10C | 0 | 0 | 0 | 0 | 0 | 1G |
| Italian ryegrass | 10C | 10C | 0 | 0 | 0 | 0 | 0 | 2G |
| ripgut brome | 10C | 10C | 0 | 0 | 0 | 0 | 0 | 0 |
| wild buckwheat | 10C | 10C | 9C | 10C | 10C | 10C | 10C | 10C |
| Kochia | 10C | 10C | 10C | 10C | 10C | 10C | 10C | 10C |
| smartweed | 10C | 10C | 9C | 9C | 10C | 10C | 10C | 10C |
| false chamomile | 10C | 10C | 10C | 10C | 10C | 10C | 10C | 10C |
| jimhill mustard | 10C | 10C | 10C | 10C | 10C | 10C | 10C | 10C |
| wild mustard | 10C | 10C | 10C | 10C | 10C | 10C | 10C | 10C |
| tansy mustard | 10C | 10C | 10C | 10C | 10C | 10C | 10C | 10C |
| pigweed | 10C | 10C | 9C | 10C | 10C | 10C | 10C | 10C |
| Russian thistle | 10C | 10C | 9C | 10C | 10C | 10C | 10C | 10C |

TEST I

Five-inch in diameter plastic pots were filled with a 50-50 mixture of Fallsington silt loam soil and sand and seeds of the following planted (one plant species per pot): milkweed vine (*Morrenia odorata*), plantain (*Plantago* spp.), burdock (*Arctium minus*), field bindweed (*Convolvulus arvensis*), dandelion (*Taraxacum officinale*), horsenettle (*Solanum carolinense*), bermudagrass (*Cynodon dactylon*), quackgrass (*Agropyron repens*), dallisgrass (*Paspalum dilatatum*) and johnsongrass (*Sorghum halepense*). The pots were placed in the greenhouse and the plants grown for several weeks.

The compound evaluated was diluted with a non-phytotoxic solvent and sprayed on the plant foliage. Untreated and solvent controls were included for comparison. One and eight weeks after treatment, a visual rating of the compound's effects on plant growth were made. These ratings are presented in Table XX. The data indicate the high activity of the test compound for the control of established broadleaved and grass perennial weeds.

TABLE XX

PERENNIAL BROADLEAF AND GRASS TEST

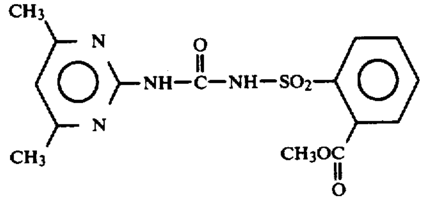

| | Plant Response Ratings | | | |
|---|---|---|---|---|
| | 1 Week | | 8 Weeks | |
| Plant Species | ⅛ kg/ha | ¼ kg/ha | ⅛ kg/ha | ¼ kg/ha |
| Milkweed vine | 0 | 0 | 10C | 10C |
| Plantain | 0 | 0 | 10C | 10C |
| Burdock | 0 | 0 | 4C | 10C |
| Field bindweed | 0 | 2C | 7C | 8C |
| Dandelion | 0 | 0 | 10C | 10C |
| Horsenettle | 0 | 1C | 5C | 10C |
| Bermudagrass | 5C | 6C | 5C,7G | 6C,8G |
| Quackgrass | 6C | 7C | 10C | 10C |
| Dallisgrass | 6C | 6C | 8C,8G | 10C |
| Johnsongrass | 8C | 9C | 10C | 10C |

TEST J

The high herbicidal activity of one of the compounds from within the scope of the invention was confirmed in a field test. The material was applied pre-emergence to a silt loam. Three days after treatment the area was irrigated with 2.5 cm of water. Four weeks later, the percentage of control was estimated for each species, as shown in Table XXI.

TABLE XXI

PRE-EMERGENCE TREATMENTS ON CROPS AND WEEDS - % CONTROL

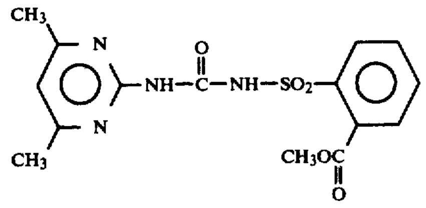

| | | kg ai/ha | | | |
|---|---|---|---|---|---|
| | Untreated | .031 | .063 | .125 | .25 |
| Crabgrass | 0 | 100 | 100 | 100 | 100 |
| Foxtail | 0 | 100 | 100 | 100 | 100 |
| Nutsedge | 0 | 98 | 100 | 100 | 100 |
| Pigweed | 0 | 100 | 100 | 100 | 100 |
| Ragweed | 0 | 100 | 100 | 100 | 100 |
| Velvetleaf | 0 | 98 | 98 | 100 | 100 |
| Lambsquarter | 0 | 100 | 100 | 100 | 100 |
| Purslane | 0 | 100 | 100 | 100 | 100 |
| Smartweed | 0 | 100 | 100 | 100 | 100 |
| Barnyardgrass | 0 | 100 | 100 | 100 | 100 |
| Ryegrass | 0 | 100 | 100 | 100 | 100 |
| Wild Oats | 0 | 98 | 100 | 100 | 100 |
| Spinach | 0 | 100 | 100 | 100 | 100 |
| Flax | 0 | 90 | 100 | 100 | 100 |
| Endive | 0 | 100 | 100 | 100 | 100 |
| Cabbage | 0 | 100 | 100 | 100 | 100 |
| Red Beets | 0 | 100 | 100 | 100 | 100 |
| Carrots | 0 | 100 | 100 | 100 | 100 |
| Lima Beans | 0 | 50 | 60 | 70 | 90 |
| Snap Beans | 0 | 80 | 90 | 95 | 100 |
| Tomatoes | 0 | 100 | 100 | 100 | 100 |
| Peanuts | 0 | 70 | 80 | 90 | 90 |
| Potatoes | 0 | 90 | 90 | 100 | 100 |
| Cucumber | 0 | 100 | 100 | 100 | 100 |
| Squash | 0 | 100 | 100 | 100 | 100 |
| Sugarbeets | 0 | 100 | 100 | 100 | 100 |
| Soybeans | 0 | 90 | 95 | 98 | 98 |
| Alfalfa | 0 | 100 | 100 | 100 | 100 |
| Clover | 0 | 100 | 100 | 100 | 100 |
| Lespedeza | 0 | 100 | 100 | 100 | 100 |
| Cotton | 0 | 80 | 90 | 90 | 95 |
| Oats | 0 | 100 | 100 | 100 | 100 |
| Okra | 0 | 90 | 90 | 100 | 100 |
| Rice | 0 | 100 | 100 | 100 | 100 |
| Wheat | 0 | 90 | 100 | 100 | 100 |
| Sorghum | 0 | 100 | 100 | 100 | 100 |
| Corn | 0 | 100 | 100 | 100 | 100 |
| Sunflower | 0 | 70 | 90 | 95 | 100 |
| Safflower | 0 | 100 | 100 | 100 | 100 |

TEST K

The response of a number of noxious weed species to post-emergence applications of the same compound as used in Test J was studied in another field test. At the time of treatment, one month after mowing, the mixed vegetation was approximately 15 cm tall. The chemical was applied in water containing 0.2% of Surfactant WK® at an overall volume of 500 l/ha. Each treatment was replicated three times. Approximately 5 cm of rainfall was recorded 4 days after treatment and an additional 37 cm fell before weed control ratings were made 16 weeks after treatment. The figures are presented in Table XXII.

TABLE XXII

BROAD-SPECTRUM WEED CONTROL TEST

MEAN % WEED CONTROL

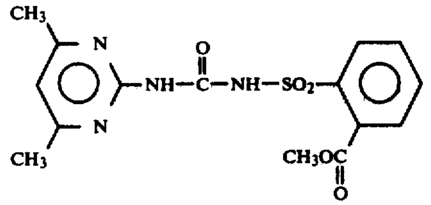

| Rate kg/ha | Untreated Check | .5 | 1.0 | 2.0 |
|---|---|---|---|---|
| Overall | 0 | 81 | 90 | 94 |
| Grasses | 0 | 81 | 84 | 93 |
| Broadleaves | 0 | 91 | 96 | 98 |
| Purpletop | 0 | 73 | 80 | 92 |
| Broomsedge | 0 | 71 | 73 | 86 |
| Golden Rod | 0 | 100 | 100 | 100 |
| Dewberry | 0 | 97 | 100 | 100 |
| Poison Ivy | 0 | 67 | 85 | 95 |

Weeds Per Sq. Ft. in untreated check:

| | |
|---|---|
| Purpletop | .7 |
| Broomsedge | .7 |
| Golden Rod | 1.0 |
| Dewberry | .5 |
| Poison Ivy | 1.0 |

I claim:

1. A compound of the formula

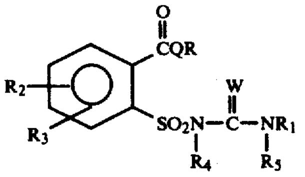

wherein
Q is O;
W is O;
R is $C_1$–$C_4$ alkyl;
$R_2$ is H;
$R_3$ is H;
$R_4$ is H;
$R_5$ is H or $CH_3$;

$R_1$ is 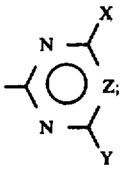

X is H, $CH_3$, $OCH_3$ or $OC_2H_5$;
Y is H, Cl, $CH_3$, $OCH_3$ or $OC_2H_5$; and
Z is CH.

2. A compound of claim 1 wherein $R_5$ is H.

3. A compound of claim 2 wherein X is $CH_3$ or $OCH_3$ and Y is $CH_3$, or $OCH_3$.

4. The compound of claim 1 which is N-[(4,6-dimethylpyrimidin-2-yl)aminocarbonyl]-2-methoxycarbonylbenzenesulfonamide.

5. The compound of claim 1 which is N-[(4-methoxy-6-methylpyrimidin-2-yl)aminocarbonyl]-2-methoxycarbonylbenzenesulfonamide.

6. The compound of claim 1 which is N-[(4,6-dimethoxypyrimidin-2-yl)aminocarbonyl]-2-methoxycarbonylbenzenesulfonamide.

7. The compound of claim 1, N-[(4,6-dimethoxypyrimidin-2-yl)-N-methylaminocarbonyl]-2-methoxycarbonylbenzenesulfonamide.

8. The compound of claim 1, N-[(4,6-dimethoxypyrimidin-2-yl)-N-methylaminocarbonyl]-2-ethoxycarbonylbenzenesulfonamide.

* * * * *